US008961560B2

(12) United States Patent
Avelar et al.

(10) Patent No.: US 8,961,560 B2
(45) Date of Patent: Feb. 24, 2015

(54) BIDIRECTIONAL SELF-RETAINING SUTURES WITH LASER-MARKED AND/OR NON-LASER MARKED INDICIA AND METHODS

(75) Inventors: Rui Avelar, Vancouver (CA); Alexei Goraltchouk, Santa Barbara, CA (US); Robert A. Herrmann, Vancouver (CA); Brian H. Luscombe, Basking Ridge, NJ (US); William L. D'Agostino, Hamden, CT (US)

(73) Assignee: Ethicon, Inc., Somerville, NJ (US)

( * ) Notice: Subject to any disclaimer, the term of this patent is extended or adjusted under 35 U.S.C. 154(b) by 155 days.

(21) Appl. No.: 12/970,872

(22) Filed: Dec. 16, 2010

(65) Prior Publication Data
US 2011/0319932 A1 Dec. 29, 2011

Related U.S. Application Data

(63) Continuation-in-part of application No. 12/992,453, filed as application No. PCT/US2009/044274 on May 16, 2009.

(60) Provisional application No. 61/053,912, filed on May 16, 2008, provisional application No. 61/290,750, filed on Dec. 29, 2009, provisional application No. 61/296,721, filed on Jan. 20, 2010.

(51) Int. Cl.
*A61B 17/04* (2006.01)
*A61B 17/06* (2006.01)
(Continued)

(52) U.S. Cl.
CPC ....... *A61B 17/06166* (2013.01); *A61B 17/0469* (2013.01); *A61B 19/44* (2013.01); *A61B 19/2203* (2013.01); *A61B 2017/00115* (2013.01); *A61B 2017/00526* (2013.01);
(Continued)

(58) Field of Classification Search
USPC ........................ 606/228–231, 139, 144, 148
See application file for complete search history.

(56) References Cited

U.S. PATENT DOCUMENTS

| 709,392 A | 9/1902 | Brown |
| 733,723 A | 7/1903 | Lukens |

(Continued)

FOREIGN PATENT DOCUMENTS

| BE | 1014364 | 9/2003 |
| CA | 2309844 | 12/1996 |

(Continued)

OTHER PUBLICATIONS

Communication from EPO re: 10000486 dated Apr. 4, 2011, 4 pages.
(Continued)

*Primary Examiner* — Gregory Anderson

(57) ABSTRACT

A marked heterofunctional suture thread has two or more sections having different features. One or more sections of the suture thread are provided with laser-marked and non-laser marked indicia in order that they may be identified and differentiated from other sections. The suture thread may have retainers on the surface of one or more sections such that the suture thread can engage and retain tissue without knots. The markers may be used to indicate fixed features of a section of suture thread such as the presence and/orientation of retainers. In particular embodiments, laser-marked and non-laser marked indicia are used to identify the transition section of a bidirectional self-retaining suture.

7 Claims, 20 Drawing Sheets

(51) Int. Cl.
 *A61B 19/00* (2006.01)
 *A61B 17/00* (2006.01)
(52) U.S. Cl.
 CPC ............... *A61B 2017/06009* (2013.01); *A61B 2017/06014* (2013.01); *A61B 2017/06057* (2013.01); *A61B 2017/06176* (2013.01); *A61B 2019/444* (2013.01); *A61B 2019/446* (2013.01); *A61B 2019/448* (2013.01); *A61B 2019/464* (2013.01); *A61B 2019/4847* (2013.01); *A61B 2019/5291* (2013.01)
 USPC ........................................................ 606/228

(56) References Cited

U.S. PATENT DOCUMENTS

| | | |
|---|---|---|
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,684,070 A | 7/1954 | Kelsey |
| 2,736,964 A | 3/1956 | Lieberman |
| 2,779,083 A | 1/1957 | Enton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,963,031 A | 6/1976 | Hunter |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,990,144 A | 11/1976 | Schwartz |
| 4,006,747 A | 2/1977 | Kronenthal |
| 4,008,303 A | 2/1977 | Glick et al. |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows |
| 4,741,330 A | 5/1988 | Hayhurst |
| 4,750,910 A | 6/1988 | Takayanagi et al. |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |

(56) References Cited

U.S. PATENT DOCUMENTS

| | | |
|---|---|---|
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schutz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |

(56) References Cited

U.S. PATENT DOCUMENTS

| | | | |
|---|---|---|---|
| 5,716,376 A | 2/1998 | Roby et al. | |
| 5,722,991 A | 3/1998 | Colligan | |
| 5,723,008 A | 3/1998 | Gordon | |
| 5,725,557 A | 3/1998 | Gatturna et al. | |
| 5,728,114 A | 3/1998 | Evans et al. | |
| 5,731,855 A | 3/1998 | Koyama et al. | |
| 5,741,277 A | 4/1998 | Gordon et al. | |
| 5,744,151 A | 4/1998 | Capelli | |
| 5,763,411 A | 6/1998 | Edwardson et al. | |
| 5,765,560 A | 6/1998 | Verkerke et al. | |
| 5,766,246 A | 6/1998 | Mulhauser et al. | |
| 5,779,719 A | 7/1998 | Klein et al. | |
| 5,782,864 A | 7/1998 | Lizardi | |
| 5,807,403 A | 9/1998 | Beyar et al. | |
| 5,807,406 A | 9/1998 | Brauker et al. | |
| 5,810,853 A | 9/1998 | Yoon | |
| 5,814,051 A | 9/1998 | Wenstrom, Jr. | |
| 5,843,087 A | 12/1998 | Jensen et al. | |
| 5,843,178 A | 12/1998 | Vanney et al. | |
| 5,855,619 A | 1/1999 | Caplan et al. | |
| 5,863,360 A | 1/1999 | Wood et al. | |
| 5,887,594 A | 3/1999 | LoCicero, III | |
| 5,891,166 A | 4/1999 | Schervinsky | |
| 5,893,856 A | 4/1999 | Jacob et al. | |
| 5,895,395 A | 4/1999 | Yeung | |
| 5,895,413 A | 4/1999 | Nordstrom | |
| 5,897,572 A | 4/1999 | Schulsinger et al. | |
| 5,899,911 A | 5/1999 | Carter | |
| 5,916,224 A | 6/1999 | Esplin | |
| 5,919,234 A | 7/1999 | Lemperle et al. | |
| 5,921,982 A | 7/1999 | Lesh et al. | |
| 5,925,078 A | 7/1999 | Anderson | |
| 5,931,855 A | 8/1999 | Buncke | |
| 5,935,138 A | 8/1999 | McJames, II et al. | |
| 5,938,668 A | 8/1999 | Scirica et al. | |
| 5,941,899 A | 8/1999 | Granger et al. | |
| 5,950,633 A | 9/1999 | Lynch et al. | |
| 5,954,747 A | 9/1999 | Clark | |
| 5,964,765 A | 10/1999 | Fenton, Jr. et al. | |
| 5,964,783 A | 10/1999 | Grafton et al. | |
| 5,968,097 A | 10/1999 | Frechet et al. | |
| 5,972,024 A | 10/1999 | Northrup, III et al. | |
| 5,984,933 A | 11/1999 | Yoon | |
| 5,993,459 A | 11/1999 | Larsen et al. | |
| 6,001,111 A | 12/1999 | Sepetka et al. | |
| 6,012,216 A | 1/2000 | Esteves et al. | |
| 6,015,410 A | 1/2000 | Tormala et al. | |
| 6,024,757 A | 2/2000 | Haase et al. | |
| 6,027,523 A | 2/2000 | Schmieding | |
| 6,039,741 A | 3/2000 | Meislin | |
| 6,056,778 A | 5/2000 | Grafton et al. | |
| 6,063,105 A | 5/2000 | Totakura | |
| 6,071,292 A | 6/2000 | Makower et al. | |
| 6,074,419 A | 6/2000 | Healy et al. | |
| 6,076,255 A | 6/2000 | Shikakubo et al. | |
| 6,083,244 A | 7/2000 | Lubbers et al. | |
| 6,102,947 A | 8/2000 | Gordon | |
| 6,106,544 A | 8/2000 | Brazeau | |
| 6,106,545 A | 8/2000 | Egan | |
| 6,110,484 A | 8/2000 | Sierra | |
| 6,129,741 A | 10/2000 | Wurster et al. | |
| D433,753 S | 11/2000 | Weiss | |
| 6,146,406 A | 11/2000 | Shluzas et al. | |
| 6,146,407 A | 11/2000 | Krebs | |
| 6,149,660 A | 11/2000 | Laufer et al. | |
| 6,159,234 A | 12/2000 | Bonutti et al. | |
| 6,160,084 A | 12/2000 | Langer et al. | |
| 6,163,948 A | 12/2000 | Esteves et al. | |
| 6,165,203 A | 12/2000 | Krebs | |
| 6,168,633 B1 | 1/2001 | Shoher et al. | |
| 6,174,324 B1 | 1/2001 | Egan et al. | |
| 6,183,499 B1 | 2/2001 | Fischer et al. | |
| 6,187,095 B1 | 2/2001 | Labrecque et al. | |
| 6,203,565 B1 | 3/2001 | Bonutti et al. | |
| 6,206,908 B1 | 3/2001 | Roby | |
| 6,214,030 B1 | 4/2001 | Matsutani et al. | |
| 6,231,911 B1 | 5/2001 | Steinback et al. | |
| 6,235,869 B1 | 5/2001 | Roby et al. | |
| 6,241,747 B1 | 6/2001 | Ruff | |
| 6,251,143 B1 | 6/2001 | Schwartz et al. | |
| 6,264,675 B1 | 7/2001 | Brotz | |
| 6,267,772 B1 | 7/2001 | Mulhauser et al. | |
| 6,270,517 B1 | 8/2001 | Brotz | |
| 6,315,788 B1 | 11/2001 | Roby | |
| 6,319,231 B1 | 11/2001 | Andrulitis | |
| 6,322,581 B1 | 11/2001 | Fukuda et al. | |
| 6,334,865 B1 | 1/2002 | Redmond et al. | |
| 6,383,201 B1 | 5/2002 | Dong | |
| 6,387,363 B1 | 5/2002 | Gruskin | |
| 6,388,043 B1 | 5/2002 | Langer et al. | |
| 6,395,029 B1 | 5/2002 | Levy | |
| D462,766 S | 9/2002 | Jacobs et al. | |
| 6,443,962 B1 | 9/2002 | Gaber | |
| 6,471,715 B1 | 10/2002 | Weiss | |
| 6,478,809 B1 | 11/2002 | Brotz | |
| 6,485,503 B2 | 11/2002 | Jacobs et al. | |
| 6,491,701 B2 | 12/2002 | Tierney et al. | |
| 6,491,714 B1 | 12/2002 | Bennett | |
| 6,494,898 B1 | 12/2002 | Roby et al. | |
| 6,495,127 B1 | 12/2002 | Wallace et al. | |
| RE37,963 E | 1/2003 | Thal | |
| 6,506,190 B1 | 1/2003 | Walshe | |
| 6,506,197 B1 | 1/2003 | Rollero et al. | |
| 6,511,488 B1 | 1/2003 | Marshall et al. | |
| 6,514,265 B2 | 2/2003 | Ho et al. | |
| 6,527,795 B1 | 3/2003 | Lizardi | |
| 6,548,002 B2 | 4/2003 | Gresser et al. | |
| 6,548,569 B1 | 4/2003 | Williams et al. | |
| 6,551,343 B1 | 4/2003 | Tormala et al. | |
| 6,554,802 B1 | 4/2003 | Pearson et al. | |
| 6,565,597 B1 | 5/2003 | Fearnot et al. | |
| 6,592,609 B1 | 7/2003 | Bonutti | |
| 6,596,296 B1 | 7/2003 | Nelson et al. | |
| 6,599,310 B2 * | 7/2003 | Leung et al. | 606/228 |
| 6,607,541 B1 | 8/2003 | Gardiner et al. | |
| 6,610,078 B1 | 8/2003 | Bru-Magniez et al. | |
| 6,613,059 B2 | 9/2003 | Schaller et al. | |
| 6,613,254 B1 | 9/2003 | Shiffer | |
| 6,616,982 B2 | 9/2003 | Merrill et al. | |
| 6,623,492 B1 | 9/2003 | Berube et al. | |
| 6,626,930 B1 | 9/2003 | Allen et al. | |
| 6,632,245 B2 | 10/2003 | Kim | |
| 6,641,592 B1 | 11/2003 | Sauer et al. | |
| 6,641,593 B1 | 11/2003 | Schaller et al. | |
| 6,645,226 B1 | 11/2003 | Jacobs et al. | |
| 6,645,227 B2 | 11/2003 | Fallin et al. | |
| 6,648,921 B2 | 11/2003 | Anderson et al. | |
| 6,656,182 B1 | 12/2003 | Hayhurst | |
| 6,689,153 B1 | 2/2004 | Skiba | |
| 6,689,166 B2 | 2/2004 | Laurencin et al. | |
| 6,692,761 B2 | 2/2004 | Mahmood et al. | |
| 6,702,844 B1 | 3/2004 | Lazarus | |
| 6,712,830 B2 | 3/2004 | Esplin | |
| 6,712,859 B2 | 3/2004 | Rousseau et al. | |
| 6,716,234 B2 | 4/2004 | Grafton et al. | |
| 6,720,402 B2 | 4/2004 | Langer et al. | |
| 6,726,705 B2 | 4/2004 | Peterson et al. | |
| 6,746,443 B1 | 6/2004 | Morley et al. | |
| 6,746,458 B1 | 6/2004 | Cloud | |
| 6,749,616 B1 | 6/2004 | Nath | |
| 6,773,450 B2 | 8/2004 | Leung et al. | |
| 6,783,554 B2 | 8/2004 | Amara et al. | |
| 6,814,748 B1 | 11/2004 | Baker et al. | |
| 6,818,010 B2 | 11/2004 | Eichhorn et al. | |
| 6,836,284 B2 * | 12/2004 | Murokh et al. | 347/255 |
| 6,838,493 B2 | 1/2005 | Williams et al. | |
| 6,848,152 B2 | 2/2005 | Genova et al. | |
| 6,852,825 B2 | 2/2005 | Lendlein et al. | |
| 6,860,891 B2 | 3/2005 | Schulze | |
| 6,860,901 B1 | 3/2005 | Baker et al. | |
| 6,867,248 B1 | 3/2005 | Martin et al. | |
| 6,877,934 B2 | 4/2005 | Gainer | |
| 6,881,766 B2 | 4/2005 | Hain | |
| 6,893,452 B2 | 5/2005 | Jacobs | |

(56) References Cited

U.S. PATENT DOCUMENTS

| | | |
|---|---|---|
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,037,984 B2 | 5/2006 | Lendlein et al. |
| 7,041,121 B1 | 5/2006 | Williams et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,371,253 B2 | 5/2008 | Leung et al. |
| 7,468,242 B2 | 12/2008 | Bellomo et al. |
| 7,513,904 B2 | 4/2009 | Sulamanidze et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 7,919,112 B2 | 4/2011 | Pathak et al. |
| 8,092,856 B2 * | 1/2012 | Hadba .................. 427/2.23 |
| 8,118,834 B1 | 2/2012 | Goraltchouk et al. |
| 8,216,273 B1 | 7/2012 | Goraltchouk et al. |
| 8,226,684 B2 | 7/2012 | Nawrocki et al. |
| 8,308,761 B2 | 11/2012 | Brailovski et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency et al. |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |

(56) References Cited

U.S. PATENT DOCUMENTS

| | | |
|---|---|---|
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamandize et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Lendlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0213770 A1 | 9/2007 | Drefyss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1* | 4/2008 | Bishop et al. ............... 606/151 |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Naworocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250588 A1 | 10/2009 | Robeson et al. |
| 2009/0259233 A1 | 10/2009 | Bogart et al. |
| 2009/0259251 A1 | 10/2009 | Cohen |

(56) References Cited

U.S. PATENT DOCUMENTS

| | | |
|---|---|---|
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0160961 A1 | 6/2010 | Nawrocki et al. |
| 2010/0163056 A1 | 7/2010 | Tschopp et al. |
| 2010/0211097 A1 | 8/2010 | Hadba et al. |
| 2010/0211098 A1 | 8/2010 | Hadba et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0046669 A1 | 2/2011 | Goraltchouk et al. |
| 2011/0106152 A1 | 5/2011 | Kozlowski |
| 2011/0130774 A1 | 6/2011 | Criscuolo et al. |
| 2011/0166597 A1 | 7/2011 | Herrmann et al. |
| 2012/0109188 A1 | 5/2012 | Viola |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 A1 | 3/1997 |
| EP | 0576337 B1 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 2036502 | 3/2009 |
| EP | 1948261 | 11/2010 |
| EP | 1726317 | 7/2012 |
| FR | 2619129 | 2/1989 |
| FR | 2693108 | 1/1994 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 54-116419 | 9/1979 |
| JP | 63-288146 | 11/1988 |
| JP | 001113091 | 5/1989 |
| JP | 3-165751 | 7/1991 |
| JP | 4-096758 | 3/1992 |
| JP | 4-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-059235 | 2/2002 |
| JP | 2003-275217 | 9/2003 |
| JP | 2009-118967 | 6/2009 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 96/06565 | 3/1966 |
| WO | WO 86/00020 | 1/1986 |
| WO | WO 87/01270 | 3/1987 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 98/52473 | 11/1998 |
| WO | WO 88/09157 | 12/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/056626 | 8/2001 |
| WO | WO 03/001979 | 1/2003 |
| WO | WO 03/003925 | 1/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |

(56) References Cited

FOREIGN PATENT DOCUMENTS

| WO | WO 2005/096956 | 10/2005 |
|----|----------------|---------|
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2008/150773 | 12/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |
| WO | WO 2011/053375 | 5/2011 |
| WO | WO 2011/139916 | 11/2011 |
| WO | WO 2011/140283 | 11/2011 |

OTHER PUBLICATIONS

European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2011/035431 dated Nov. 6, 2012.
International Preliminary Report re: PCT/US2011 /059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/20449 dated May 20, 2003.
International Search Report for PCT/US2002/027525 dated Dec. 9, 2002, 3 pages.
International Search Report for PCT/US2003/030424 dated Nov. 1, 2004.
International Search Report for PCT/US2003/030664 dated May 25, 2004.
International Search Report for PCT/2003/030666 dated Dec. 15, 2004.
International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/063081 dated Aug. 2, 2010.
International Search Report for PCT/US2009/041685 dated Dec. 22, 2009.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report for PCT/US2011/059238 dated May 21, 2012.
International Search Report for PCT/US2012/030441 dated Sep. 27, 2012.
International Search Report for PCT/US2012/041001 dated Sep. 26, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.

(56) References Cited

OTHER PUBLICATIONS

Singapore Search Report for Singapore Patent Application No. 201103117-6 dated Mar. 8, 2013.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 05750101 dated Apr. 7, 2010.
Supplementary European Search Report re: 07017663 dated Nov. 7, 2007.
Written Opinion of the International Searching Authority re: PCT/US2010/056898 dated Aug. 2, 2011.
Written Opinion of the International Searching Authority re: PCT/US2012/041001 dated Sep. 26, 2012.
International Preliminary Report on Patentability for PCT/US2009/044274, dated Nov. 17, 2010.
International Search Report for PCT/US2009/044274 dated Jan. 15, 2010.
US 6,447,535, (withdrawn).
US 6,503,260, (withdrawn).
Bacci, Pier Antonio, "Chirurgia Estetica Mini Invasiva Con Fili Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. 1999 vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
Bunnell, S. 'Gig pull-out suture for tendons' J Bone Joint Surg. Am (1954) vol. 36A, No. 4 pp. 850-851.
CCPR Centro De Cirurgia Plastica e Reabilitacao 'Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar. 2006 26(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 2006 27(2): 2 pages.
Gross, R.A. et al 'Biodegradable Polymers for the Environment' Science (2002) vol. 297, Issue 5582 pp. 803.
Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.
Ingle, N.P. et al 'Barbed Suture Anchoring Strength: Applicability to Dissimilar Polymeric Materials' College of Textiles, North Carolina State University, 7th World Biomaterials Congress 2004, 1 page.
Ingle, N.P. et al 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.
Jennings et al 'A New Technique in primary tendon repair' Surg. Gynecol. Obstet. (1952) vol. 95, No. 5 pp. 597-600.
Jeong, H.E. et al 'A nontransferring dry adhesive with hierarchial polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[∈-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al 'Biodegradable, Elastic Shape-Memory Polymers for Potential Biomedical Applications' (2002) Science vol. 296 pp. 1673-1676.
Lendlein, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.
Li, Y.Y. et al 'Polymer Replicas of Photonic Porous Silicon for Sensing and Drug Delivery Applications' (2003) Science vol. 299 p. 2045-2047.

(56) References Cited

OTHER PUBLICATIONS

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Madhave et al 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics 2007 May/Jun.;12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.
Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and Biomaterials Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http://www.physorg.com/news117214996.html>.
Murtha et al., "Evaluation of a Novel Technique for Wound Closure Using a Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures A Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, Aug. 2007-2009: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, Aug. 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-inClass Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.
Sulamanidze, M.A. et al 'Facial lifting with APTOS threads' International Journal of Cosmetic Surgery and Aesthetic Dermatology (2001) No. 4 pp. 1-8.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach-internal stitching technique (APTOS NEEDLE)", Plastic and Aesthetic Surgery Clinic TOTAL SHARM, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Tan E.L. et al., "A wireless, passive strain sensor based on the harmonic response of magnetically soft materials", Smart Materials and Structures 17 (2008): pp. 1-6.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.

* cited by examiner

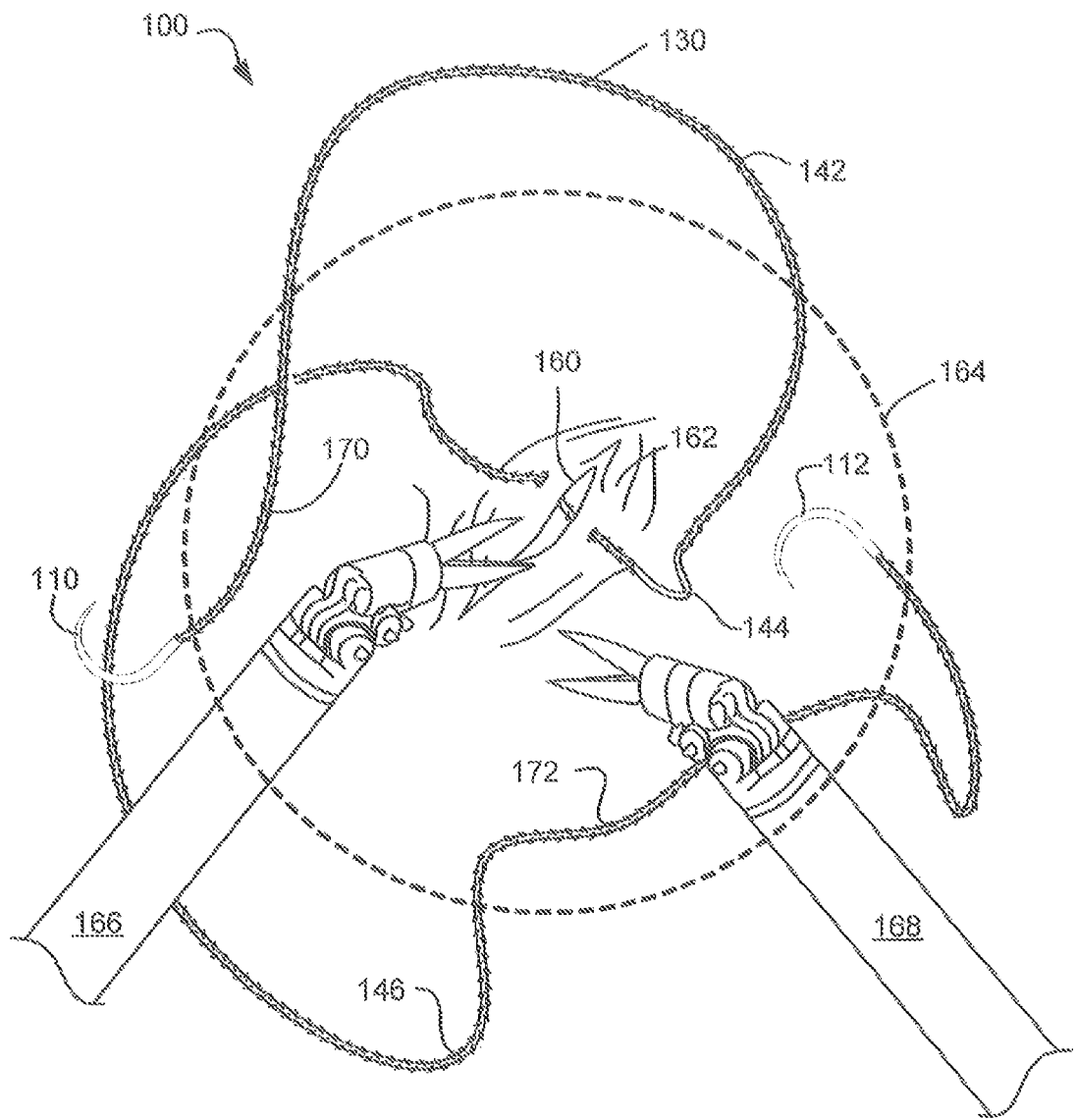

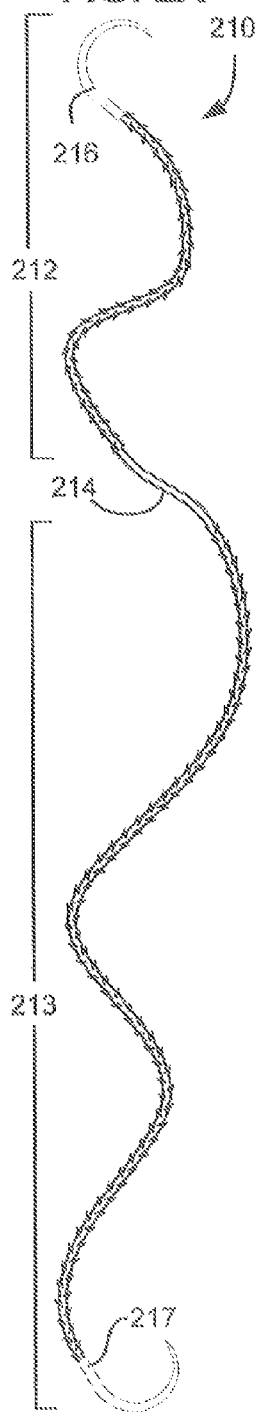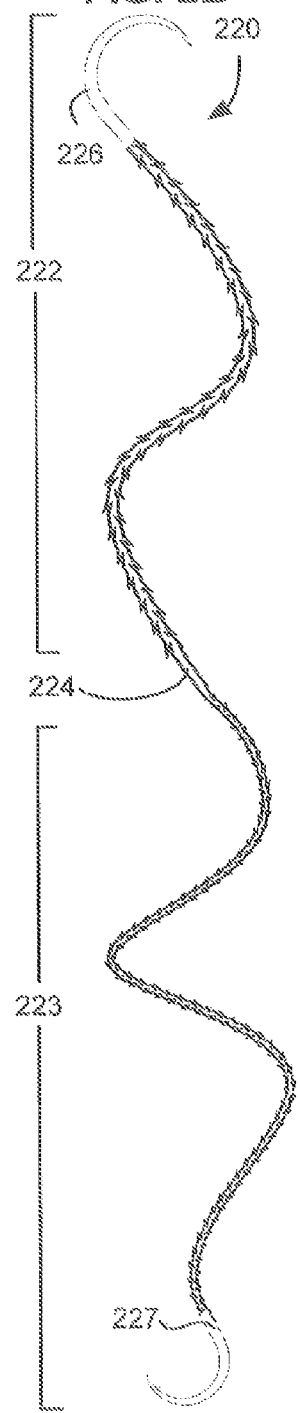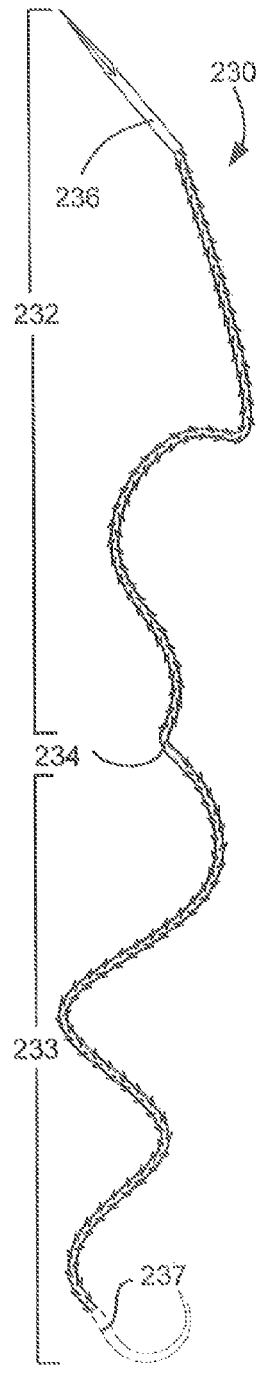

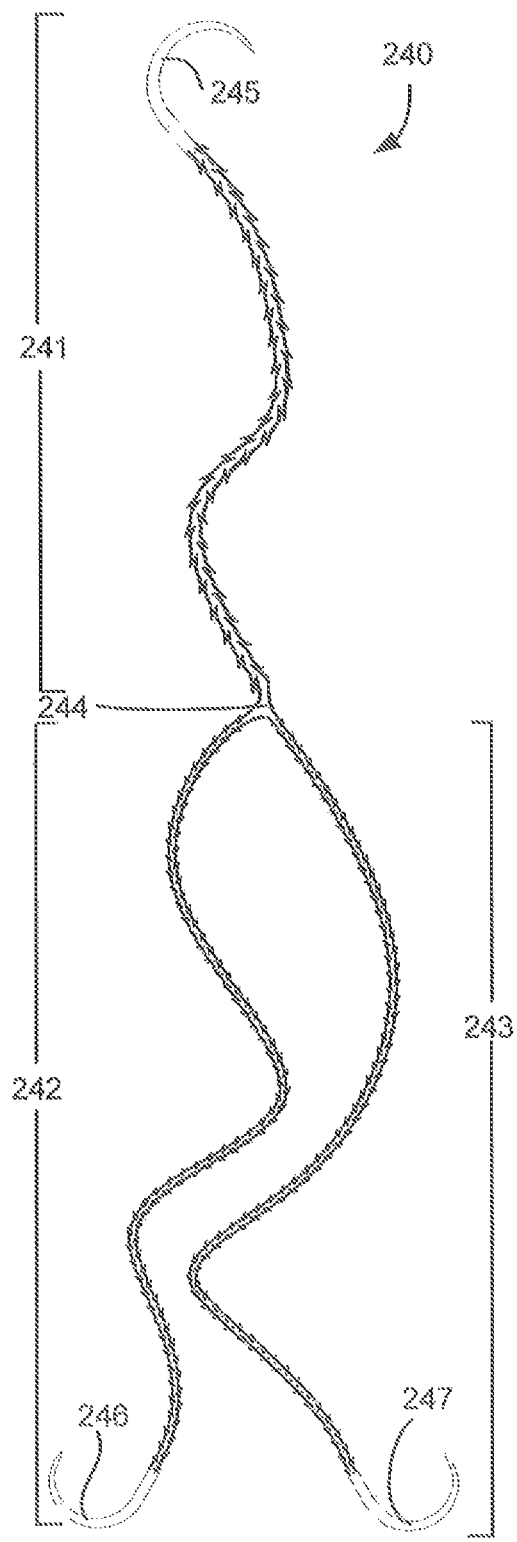

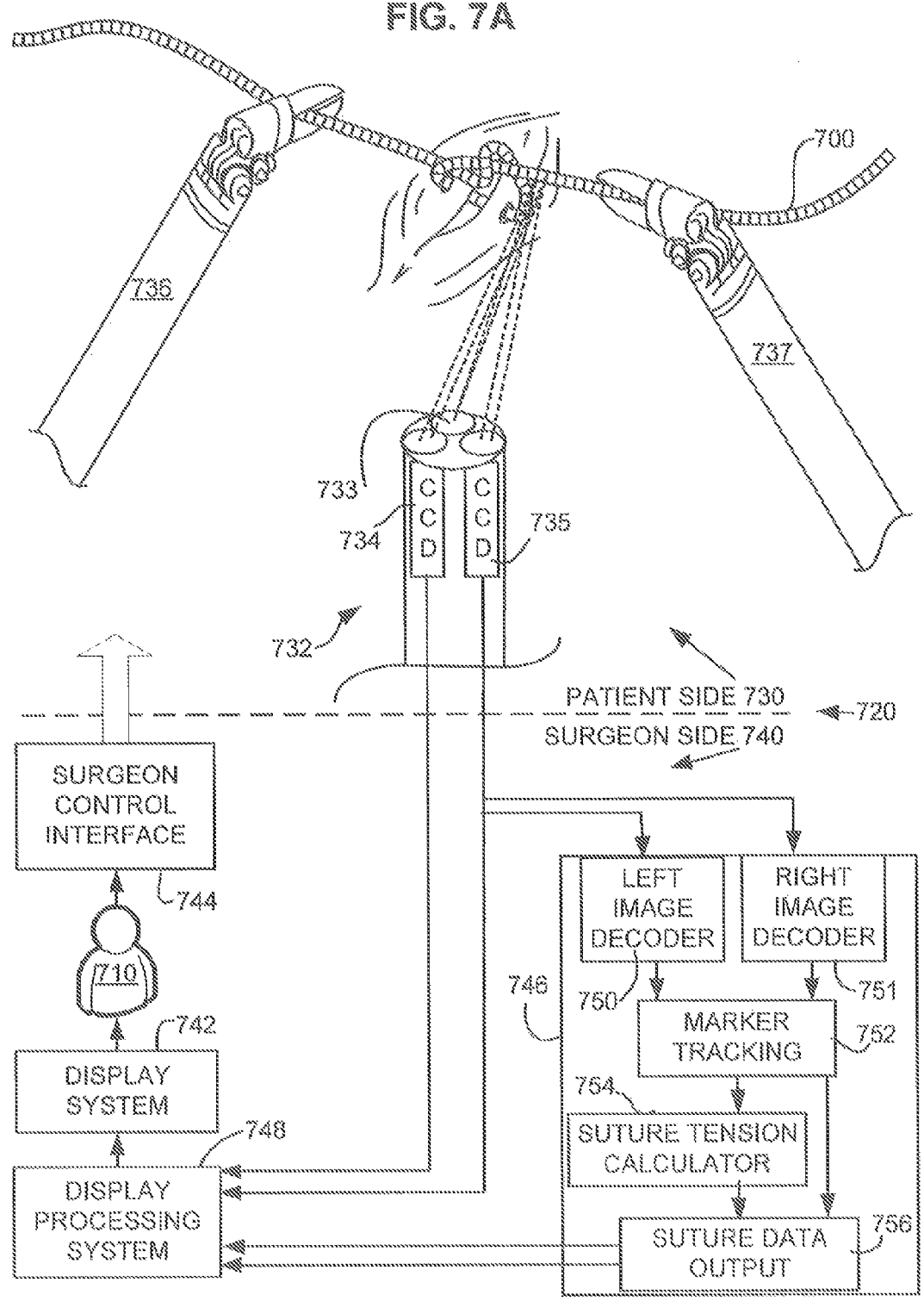

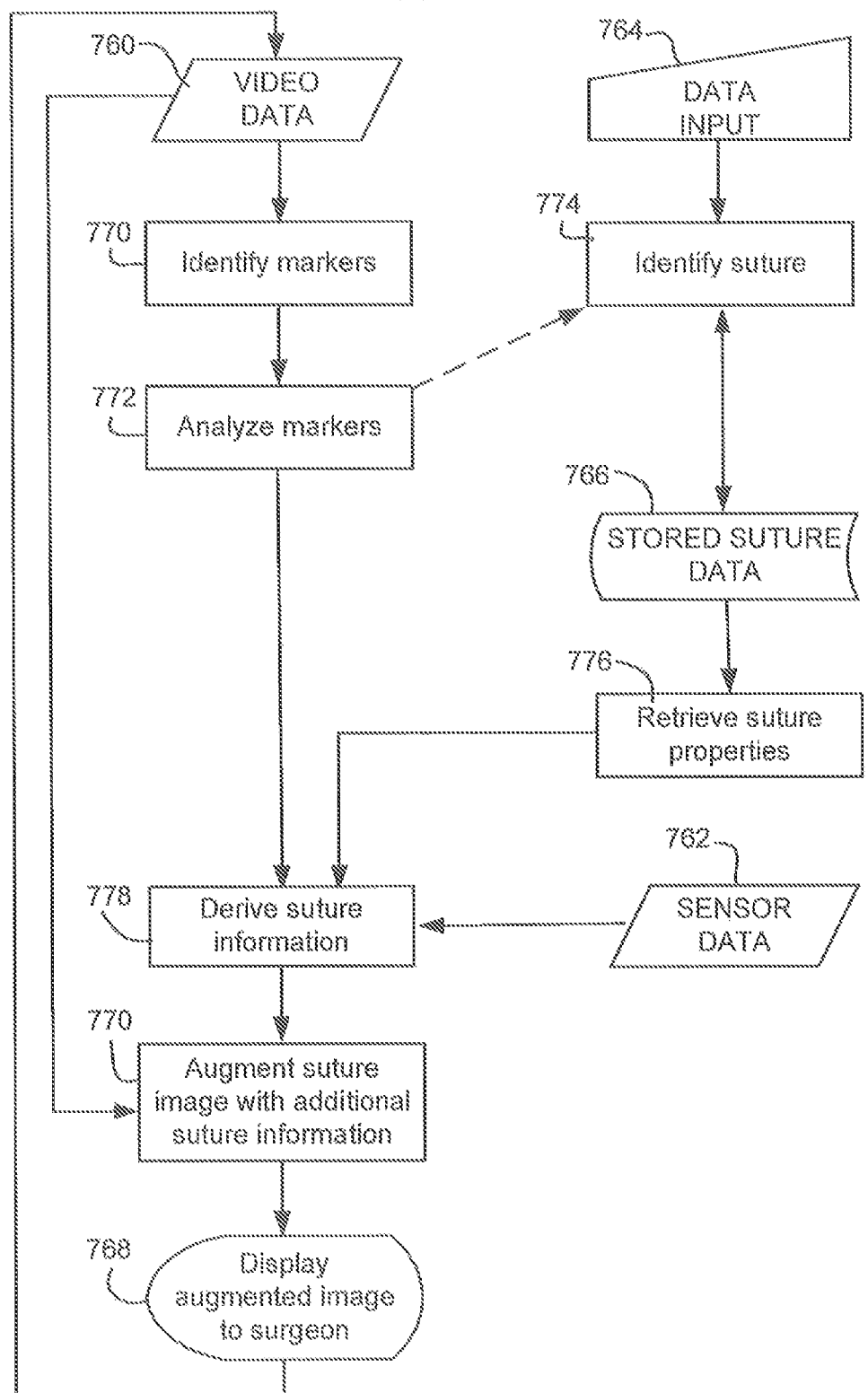

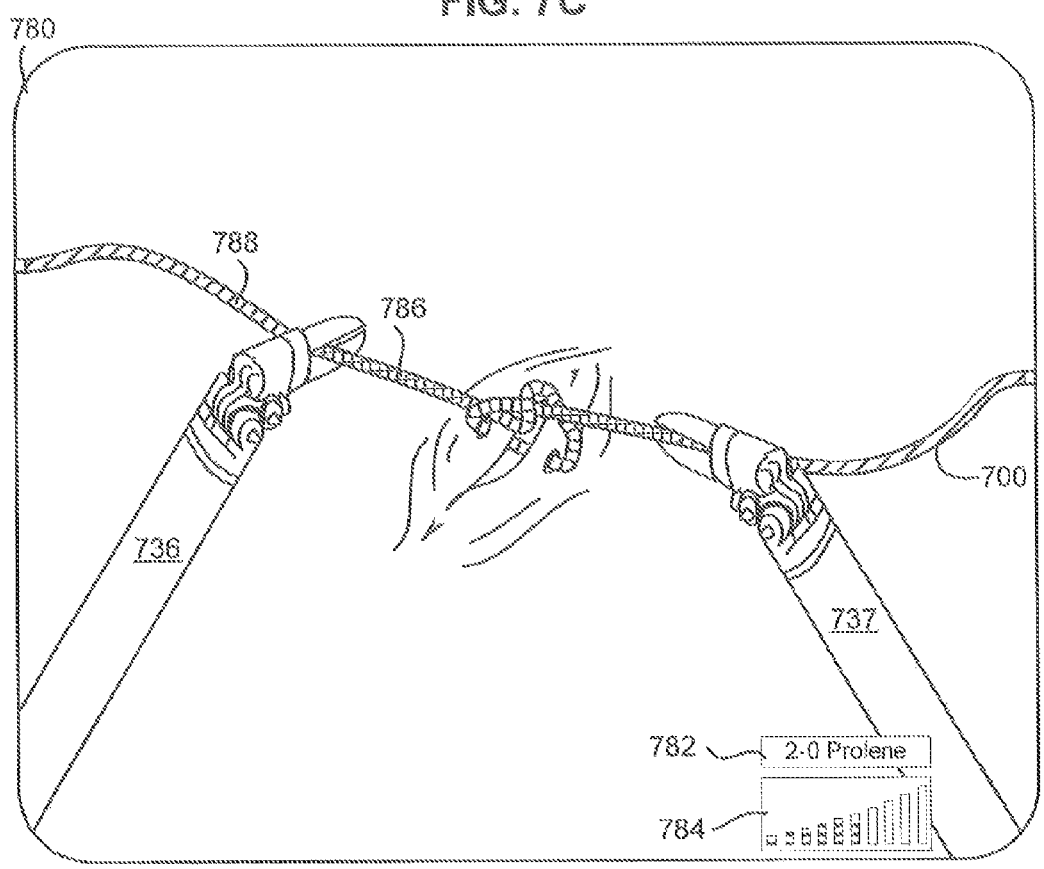

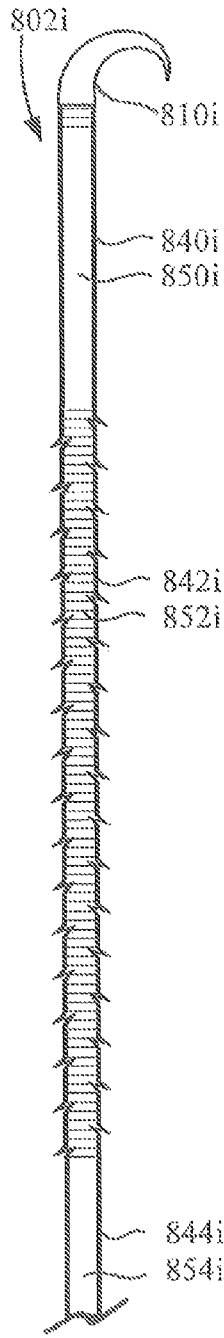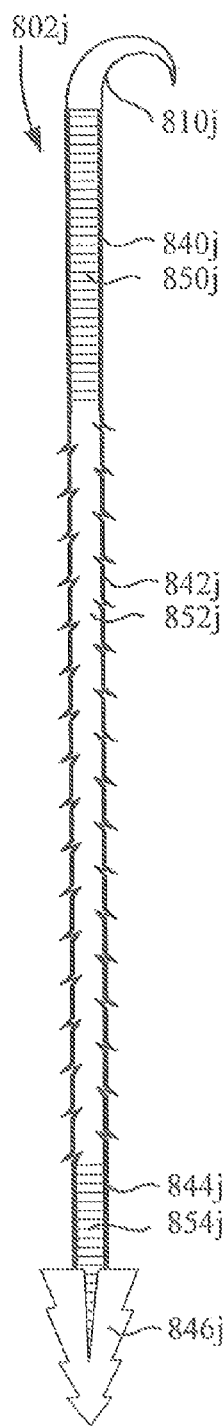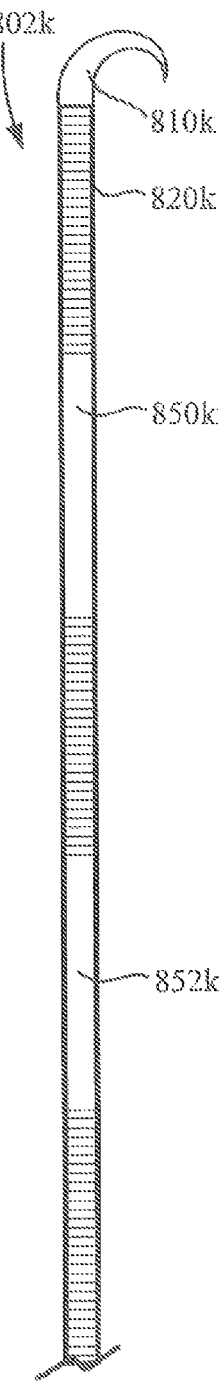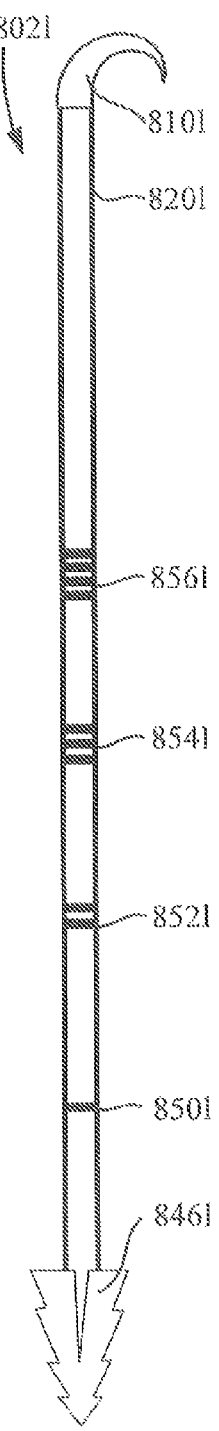

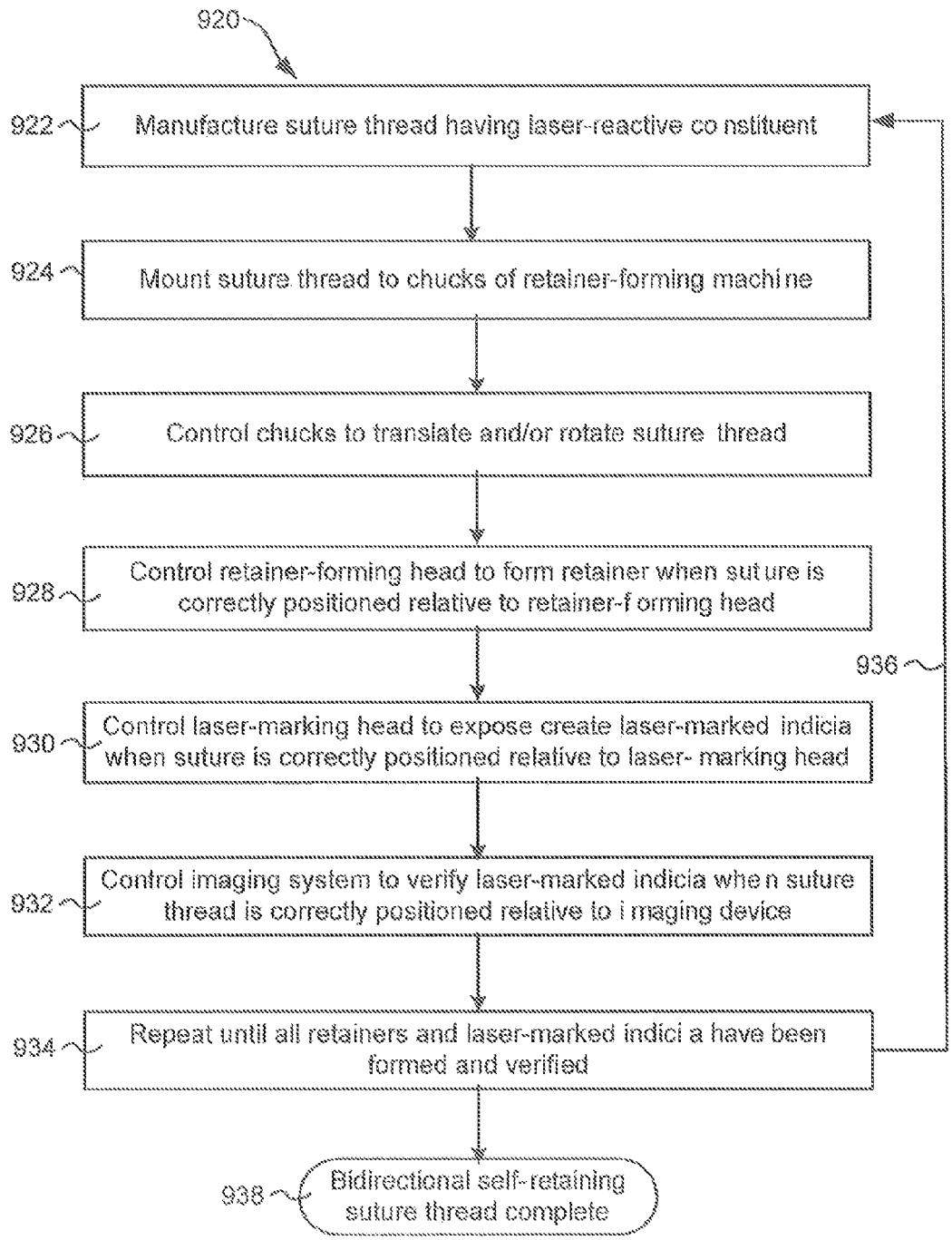

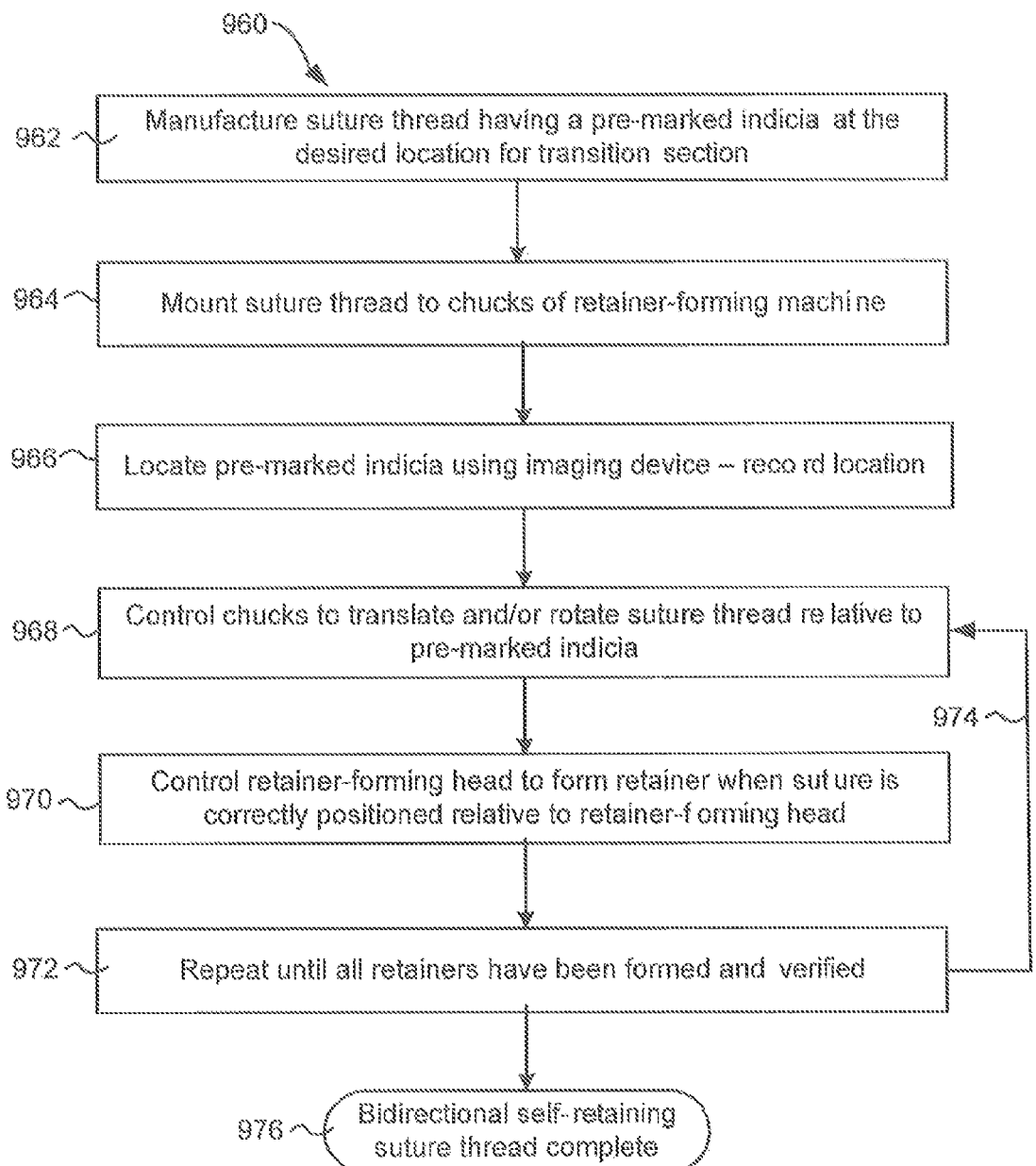

BIDIRECTIONAL SELF-RETAINING SUTURES WITH LASER-MARKED AND/OR NON-LASER MARKED INDICIA AND METHODS

CROSS REFERENCE TO RELATED APPLICATIONS

This application is a continuation-in-part of U.S. application Ser. No. 12/992,453, filed Nov. 12, 2010, which is the National Stage of International Application No. PCT/US2009/044274, filed May 16, 2009, and which claims the benefit of U.S. Provisional Application No. 61/053,912, filed May 16, 2008. This application also claims the benefit of U.S. Provisional Application No. 61/290,750, filed Dec. 29, 2009, and U.S. Provisional Application No. 61/296,721, filed Jan. 20, 2010. All of the above patent applications are incorporated herein by reference in their entirety.

FIELD OF INVENTION

The present invention relates generally to self-retaining systems for surgical procedures, methods of manufacturing self-retaining systems for surgical procedures, and uses thereof.

BACKGROUND OF INVENTION

Wound closure devices such as sutures, staples and tacks have been widely used in superficial and deep surgical procedures in humans and animals for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures are often used as wound closure devices. Sutures typically consist of a filamentous suture thread attached to a needle with a sharp point. Suture threads can be made from a wide variety of materials including bioabsorbable (i.e., that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available; the shape and size of the needle body and the configuration of the needle tip is typically selected based upon the needs of the particular application.

To use an ordinary suture, the suture needle is advanced through the desired tissue on one side of the wound and then through the adjacent side of the wound. The suture is then formed into a "loop" which is completed by tying a knot in the suture to hold the wound closed. Knot tying takes time and causes a range of complications, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (knots can create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time).

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. No. 6,848,152. Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin All of these features are thought to reduce scarring, improve cosmesis, and increase wound strength relative to wound closures using plain sutures or staples. Thus, self-retaining sutures, because such sutures avoid knot tying, allow patients to experience an improved clinical outcome, and also save time and costs associated with extended surgeries and follow-up treatments. It is noted that all patents, patent applications and patent publications identified throughout are incorporated herein by reference in their entirety.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot tying (to prevent "slippage" when tension is momentarily released during tying); (iv) self-retaining sutures are superior in procedures where knot tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and 6,241,747). Although any number of sequential or intermittent configurations of retainers are possible, a common form of bidirectional self-retaining suture involves a needle at one end of a suture thread which has barbs having tips projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also have tips projecting "away" from the nearest needle). Projecting "away" from the needle means that the tip of the barb is further away from the needle and the portion of suture comprising the barb may be pulled more easily through tissue in the direction of the needle than in the opposite direction. Put another way, the barbs on both "halves" of a typical bidirectional self-retaining suture have tips that point towards the middle, with a transition segment (lacking barbs) interspersed between them, and with a needle attached to either end.

Given the variety and characteristics of sutures, there is a need for a physician to be able to identify such variety and characteristics during a procedure.

SUMMARY OF INVENTION

Despite the multitude of advantages of unidirectional and bidirectional self-retaining sutures, there remains a need to improve upon the design of the suture such that a variety of limitations can be eliminated and enhanced and/or additional functionality is provided.

In accordance with one aspect, the present invention provides heterofunctional sutures and self-retaining sutures having sections of suture filament with different features.

In accordance with another aspect, the present invention provides self-retaining sutures having visible/recognizable indicia associated therewith to facilitate the identification and differentiation of sections of suture filament having different features.

In accordance with another aspect, the present invention provides methods and devices for providing one or more visible/recognizable indicia on a section of a self-retaining suture.

In accordance with particular embodiments the self-retaining sutures are bidirectional self-retaining sutures.

In accordance with particular embodiments, the present invention provides methods and devices for providing one or more visible/recognizable indicia on a section of a self-retaining suture.

In accordance with particular embodiments, the present invention provides for systems and methods that can use sutures with indicia during the performance of surgical procedures.

In accordance with particular embodiments, the present invention provides for systems and methods that can use sutures with indicia during the performance of endoscopic and robotically assisted surgical procedures.

The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

Features of the invention, its nature and various advantages will be apparent from the accompanying drawings and the following detailed description of various embodiments.

FIG. 1E illustrates an endoscopic view of a bidirectional self-retaining suture to demonstrate problems solved by the present invention.

FIGS. 2A-2D show examples of heterofunctional sutures having two or more sections having different features according to embodiments of the present invention.

FIG. 7A shows an endoscopic system capable of utilizing machine-readable suture markers and needle markers associated with one or more sections of a suture to indicate a fixed feature or condition of a suture according to an embodiment of the present invention.

FIG. 7B shows a flowchart showing steps in the operation of a videoscopic system capable of utilizing machine-readable suture markers and needle markers associated with a suture to indicate a fixed feature or condition of a suture according to an embodiment of the present invention.

FIG. 7C shows an example of a video display augmented with suture information derived from suture markers according to an embodiment of the present invention.

FIGS. 8I-8J show alternative configurations of laser-marked indicia used to identify sections of a self-retaining suture thread in accordance with embodiments of the present invention.

FIGS. 8K-8L show alternative configurations of laser-marked indicia used to identify features of an ordinary suture thread in accordance with embodiments of the present invention.

FIG. 9B shows a flow chart of a process for operating the retainer-forming machine and integrated laser-marking head of FIG. 9A according to an embodiment of the invention.

FIG. 9C shows a flow chart of a process for operating a modified version of the retainer-forming machine of FIG. 9A having no integrated laser-marking head according to an embodiment of the invention.

DETAILED DESCRIPTION

Definitions

Figure 1A:
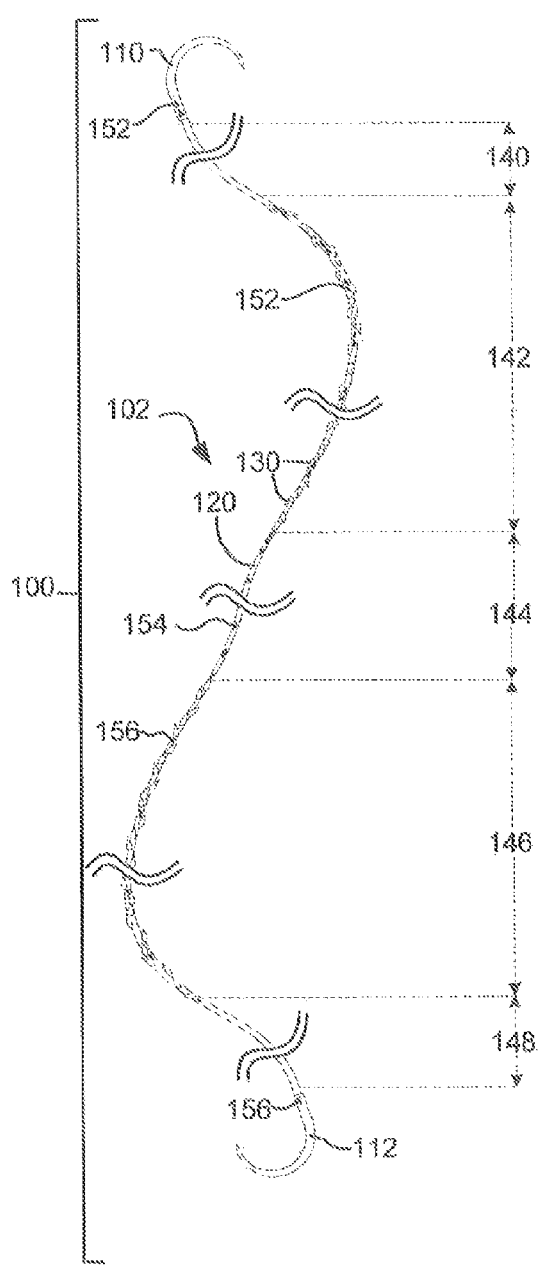
FIG. 1A is a perspective view of a bidirectional self-retaining suture in accordance with an embodiment of the present invention.

Definitions of certain terms that may be used hereinafter include the following.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Self-retaining suture" refers to a suture that comprises features on the suture filament for engaging tissue without the need for a knot or suture anchor.

"Tissue retainer" (or simply "retainer") or "barb" refers to a physical feature of a suture filament which is adapted to mechanically engage tissue and resist movement of the suture in at least one axial directions. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the physician, by being oriented to substantially face the deployment direction. In some embodiments the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In certain other embodiments, the tissue retainers may be configured to permit motion of the suture in one direction and resist movement of the suture in another direction without fanning out or deploying. In certain other configurations, the tissue retainer may be configured or combined with other tissue retainers to resist motion of the suture filament in both directions. Typically a suture having such retainers is deployed through a device such as a cannula which prevents contact between the retainers and the tissue until the suture is in the desired location.

"Retainer configurations" refers to configurations of tissue retainers and can include features such as size, shape, flexibility, surface characteristics, and so forth. These are sometimes also referred to as "barb configurations".

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transition segment located between the two barb orientations.

"Transition segment" refers to a retainer-free (barb-free) portion of a bidirectional suture located between a first set of retainers (barbs) oriented in one direction and a second set of retainers (barbs) oriented in another direction. The transition segment can be at about the midpoint of the self-retaining suture, or closer to one end of the self-retaining suture to form an asymmetrical self-retaining suture system.

"Suture thread" refers to the filamentary body component of the suture. The suture thread may be a monofilament, or comprise multiple filaments as in a braided suture. The suture thread may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable suture" (also referred to as "biodegradable suture" or "absorbable suture") refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these)

or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Covidien), terpolymer composed of glycolide, trimethylene carbonate, and dioxanone (e.g., BIOSYN™ [glycolide (60%), trimethylene carbonate (26%), and dioxanone (14%)], Covidien), copolymers of glycolide, caprolactone, trimethylene carbonate, and lactide (e.g., CAPROSYN™, Covidien). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S. Patent Application Publication Nos. 20020161168, 20040024169, and 20040116620. Sutures made from degradable suture material lose tensile strength as the material degrades. Degradable sutures can be in either a braided multifilament form or a monofilament form.

"Non-degradable suture" (also referred to as "non-absorbable suture") refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003). The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles are preferred.

Suture needles may also be classified according to the geometry of the tip or point of the needle. For example, needles may be (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030; and 5,464,422; and 5,941,899; 5,425,746; 5,306,288 and 5,156,615; and 5,312,422; and 7,063,716. Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Armed suture" refers to a suture having a suture needle on at least one suture deployment end. "Suture deployment end"

refers to an end of the suture to be deployed into tissue; one or both ends of the suture may be suture deployment ends. The suture deployment end may be attached to a deployment device such as a suture needle, or may be sufficiently sharp and rigid to penetrate tissue on its own.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects and loss of tissue volume effect downward migration of tissue, and fat descends into the plane between the superficial and deep facial fascia, thus causing facial tissue to sag. Face-lift procedures are designed to lift these sagging tissues, and are one example of a more general class of medical procedure known as a tissue elevation procedure. More generally, a tissue elevation procedure reverses the appearance change that results from effects of aging and gravity over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing and/or replacing damaged or diseased organs and tissues. While normally composed of biologically compatible synthetic materials (e.g., medical-grade stainless steel, titanium and other metals or polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

Marked Heterofunctional Sutures

As discussed above, the present invention provides compositions, configurations, methods of manufacturing and methods of using sutures, heterofunctional sutures and self-retaining sutures in surgical procedures which eliminate a variety of limitations and provide enhanced and/or additional functionality. As used herein, a heterofunctional suture is a suture having two or more functionally distinct sections of suture filament where the sections of filament have different features. A heterofunctional suture may also encompass sutures having two or more sections of filament where devices associated with the sections of filament, such as a needle by way of example only, have different features. As used herein the term "feature" is used to refer to a fixed property of a suture, such as material, retainer orientation, nominal diameter, needle configuration etc. The term "condition" is used to refer to variable properties of a suture filament such as tension, temperature etc. The term property is used to encompass both features (fixed properties) and conditions (variable properties) of sutures. The two or more sections of suture filament in a heterofunctional suture need not be of any particular length, but a section should be long enough for its difference in property to have an effect on the functionality of the section. This typically requires a length of suture long enough for at least one pass or bite through tissue under the conditions of use. Typically "a section of suture" will be a portion of suture having a length at least two orders of magnitude larger than the diameter and more typically, three or four orders of magnitude larger than the diameter of the suture.

In accordance with particular embodiments, the present invention provides sutures and self-retaining sutures which are dual-armed sutures; triple-armed sutures; multiple-armed sutures; heterofunctional sutures having two or more sections of suture having different features; dual-arm sutures having different types (or sizes) of needles on each end; single or dual-armed sutures for use with different layers/depth and types of tissue; single or dual armed sutures with sections of filament having different diameters for use with different layers/depth and types of tissue; dual-armed sutures having asymmetrically placed transition sections; and sutures having a combination of two or more of these features. According to particular embodiments of the present invention, these sutures, self-retaining sutures and/or sections thereof may be unmarked, marked or differentially-marked by one or more types of markers or combination of markers. Marked sutures include by way of example, dual-armed sutures having different markers on each end of the suture; heterofunctional sutures having different markers on different sections of suture; self-retaining sutures having markers indicative of the presence, absence and/or orientation of retainers in a section of suture; dual-armed sutures having different markers on each needle; dual-armed sutures having markers to identify orientation or direction of an end of a dual armed suture; sutures having markers utilized in robotically assisted surgical tools and with endoscopic surgical tools; sutures having markers that identify types and characteristics of sutures and call up such data from tables in computer devices (computer-assisted surgery devices) which display that information for the doctor or limit what the doctor can do as far as tensioning the suture as deployed; and sutures having markers in combination with sound or variable sound generators or light or variable light generators or haptic devices that vary a stimulus provided to a physician depending on the stress, strain and/or tension on the sutures.

The markers may be provided on the suture or on a needle or on another device associated with a suture or section of suture for example a pledget or the like. The markers include, but are not limited to: markers which identify features of the suture such as materials and/or other fixed properties; markers which identify conditions of the suture such as tension and/or other variable properties; markers visible in the visible light frequency range; markers invisible to the naked eye but which are visualized under the conditions of surgical use; markers recognizable in the non-visible radiation frequency range; markers detectable with ultrasound; markers which are machine readable; markers which may be read remotely; markers which are active markers; markers which are passive markers (passive RFID); markers which include an LED and an accelerometer or strain sensor; markers which include a light source and a sensor responsive to conditions of the suture; markers which identify the presence, absence and/or orientation of retainers; markers which identify different sections of a suture having different features; markers which change color due to suture stress, strain and/or tension; markers with alternating colors where the colors blend and produce a different color in response to suture stress, strain and/or tension; strain and/or tension; markers with different colors placed at different depths or side by side where the colors blend and produce a different color in response to suture stress, strain and/or tension; markers having one or more patterns where the patterns interfere with each to produce a visible or recognizable change in pattern in response to suture stress, strain and/or tension; markers which span a stretchable suture body and a relatively not stretchable retainer (somewhat isolated from the body) such that there is a noticeable misalignment when the suture body is under stress and stretched; and markers which deform or change configuration when the suture is under stress; markers which extend from housings or sleeves or cavities in the needle or suture when the suture is under stress; markers useful with stereo/3D imaging devices.

Marked Heterofunctional Self-Retaining Suture Systems

FIG. 1A illustrates a heterofunctional self-retaining suture system 100. Self-retaining suture system 100 comprises needles 110, 112 attached to self-retaining suture thread 102. Self-retaining suture thread 102 includes a plurality of retainers 130 distributed on the surface of a filament 120. In lead-in section 140 of filament 120 there are no retainers 130. In section 142 of filament 120 there are a plurality of retainers 130 arranged such that the suture can be deployed in the direction of needle 110, but resists movement in the direction of needle 112. In transition section 144, there are no retainers 130. In section 146, there are a plurality of retainers 130 arranged such that the suture can be deployed in the direction of needle 112, but resists movement in the direction of needle 110. The retainers 130 in section 146 are larger than the retainers 130 in section 142. The larger retainers are better suited for gripping tissue that is softer and/or less dense than the smaller retainers. In lead-in section 148 of filament 120 there are no retainers 130.

A break is shown in each of sections 140, 142, 144, 146 and 148 to indicate that the length of each section may be varied and selected depending upon the application for which the suture is intended to be used. For example, transition section 144 can be asymmetrically located closer to needle 110 or needle 112, if desired. A self-retaining suture having an asymmetrically located transition section 144 may be favored by a physician that prefers to use his dominant hand in techniques that require suturing in opposite directions along a wound. The physician may start further from one end of the wound than the other and stitch the longer portion of the wound with the needle that is located further from the transition section 144. This allows a physician to use his dominant hand to stitch the majority of the wound with the longer arm of the suture. The longer arm of the suture is that section of suture between the transition section and the needle which is located further from the transition section.

Heterofunctional self-retaining suture system 100 is composed of two arms having different functions. Each arm may be considered to be a section of self-retaining suture system 100. The first arm comprising sections 142 and section 140 of self-retaining suture thread 102 and a curved needle 110 has relatively small retainer suitable for engaging harder/denser tissue. The second arm comprising sections 146 and 148 and needle 112 of self-retaining suture thread 102 has relatively larger retainers suitable for engaging softer/less dense tissue. Self-retaining suture thread 102 of FIG. 1A is a heterofunctional suture thread because each arm of the suture has different features. For example, as previously stated, the first arm has relatively small retainer suitable for engaging harder/denser tissue and the second arm has relatively larger retainers suitable for engaging softer/less dense tissue. During surgery, it may however, be difficult for the physician to differentiate one arm or needle of self-retaining suture system 100 from the other arm or to identify and differentiate one arm or needle of self-retaining suture thread 102 the other arm. Thus, in accordance with certain embodiments of the present invention, self-retaining suture system 100 can be provided with visible markers associated with one or other of the arms or needle of the self-retaining suture system or sections of the heterofunctional suture thread 102. The visible markers enable a physician to recognize and differentiate the arms of the heterofunctional self-retaining suture system 100 and/or the sections of the heterofunctional suture thread 102.

Figure 1B:
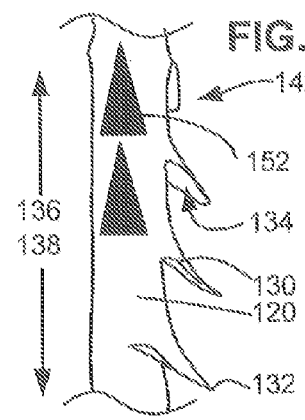
FIGS. 1B-1D are enlarged views of portions of the suture of FIG. 1A.

FIG. 1B illustrates a magnified view of self-retaining suture thread 102 in section 142. As shown in FIG. 1B, a plurality of retainers 130 is distributed on the surface of filament 120. The affixation of self-retaining sutures after deployment in tissue entails the penetration of retainer ends 132 into the surrounding tissue resulting in tissue being caught between the retainer 130 and the body of suture filament 120. The inner surface 134 of the retainer 130 that is in contact with the tissue that is caught between the retainer 130 and the body of filament 120, is referred to herein as the "tissue engagement surface" or "inner retainer surface." As illustrated in FIG. 1B, each retainer 130 has a tip 132 and tissue retainer surface 134. When self-retaining suture thread 102 is moved in the direction of arrow 136, retainers 130 lies flat against the body of filament 120. However, when self-retaining suture thread 102 is moved in the direction of arrow 138, tip 132 of retainer 130 engages tissue surrounding filament 120 and causes retainer 130 to fan out from filament 120 and engage the tissue with tissue engagement surface 134 thereby preventing movement of the suture in that direction. As shown, in FIG. 1B, the filament 120 in section 142 carries a marker 152 composed of two triangles. The tip of the triangles point in one direction along the longitudinal axis of the filament 120. This direction shown by arrow 136 is the direction in which section 142 of self-retaining suture thread 102 can be deployed without retainers 130 engaging tissue. Thus marker 152 both identifies section 142 and indicates its orientation. As shown in FIG. 1A, needle 110 may also be marked with the same marker 152.

Figure 1C:
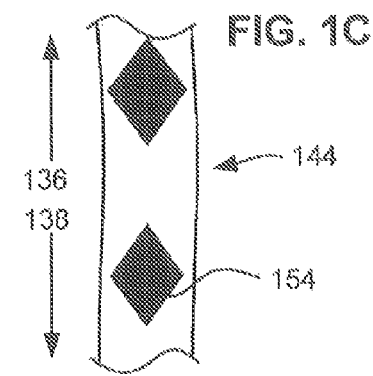

FIG. 1C illustrates a magnified view of self-retaining suture thread 102 in section 144. As shown in FIG. 1C, in section 144, there are no retainers 130. Section 144 may be referred to as the transition section of self-retaining suture system 100. Section 144 may be deployed in either both of the directions shown by arrows 136 and 138. In many procedures it is desirable to locate the transition region in order to properly situate the transition region at the beginning of suture deployment. As shown, in FIG. 1C, the filament 120 in section 144 carries a marker 154 composed of a diamond. The tips of the diamonds point in both directions, illustrating that section 144 of self-retaining suture thread 102 can be deployed in either direction and differentiating section 144 from section 142.

Figure 1D:
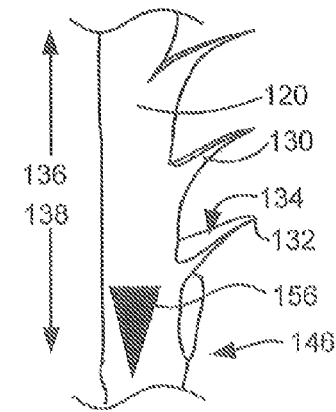

FIG. 1D illustrates a magnified view of self-retaining suture thread 102 in section 146. As shown in FIG. 1D, a plurality of retainers 130 is distributed on the surface of filament 120. As illustrated in FIG. 1D, each retainer 130 has a tip 132 and tissue retainer surface 134. When self-retaining suture thread 102 is moved in the direction of arrow 138, retainer 130 lies flat against the body of filament 120. However, when self-retaining suture thread 102 is moved in the direction of arrow 136, tip 132 or retainer 130 engages tissue surrounding filament 120 and causes retainer 130 to fan out from filament 120 and engage the tissue with face 134, thereby preventing movement of the suture in that direction. Thus, in section 146 retainers 130 are oriented in the opposite direction to the retainers 130 in section 142. As shown, in FIG. 1D, the filament 120 in section 146 carries a marker 156 composed of a single triangle. The tip of the triangle points in the direction of arrow 138 in which section 146 of self-retaining suture thread 102 can be deployed without retainers 130 engaging tissue. Note that marker 156 is different than marker 152 allowing the arms of self-retaining suture system 100 to be recognized and differentiated. Thus marker 156 identifies the orientation of the retainers in section 146 and differentiates section 146 from sections 144 and 142. As shown in FIG. 1A, needle 112 may also be marked with the same marker 156. Additionally, marker differences can include different shapes, different colors, different numbers, and different letters to name a few types of markers.

FIG. 1E illustrates the problem solved by the present invention. As shown in FIG. 1E, an unmarked self-retaining suture system 100 is used in a cavity of the human body to close an opening 160 in tissue 162. The procedure is being performed endoscopically and the visual field 164 of the physician is limited to the section inside the dashed circle. The physician has taken a bite through the tissue 162 on both sides of opening 160. Two endoscopic instruments 166 and 168 are controlled by the physician and are visible to the physician within the operative field 164. The physician has taken a bite through the tissue 162 on each side of opening 160 with needle 112 and drawn section 146 through the tissue to the position shown in FIG. 1E. The physician has temporarily released self-retaining suture system 100 with the endoscopic instruments. Needle 112 and a portion of self-retaining suture system 100 are outside of the visual field.

The physician wishes to move the transition section 144 so that it is approximately centered upon opening 160 and then pick up needle 112 and take another bite through the tissue on each side of opening 160 moving from right to left. However, the retainers 130 along are not sufficiently visible to the physician via the endoscope. Also, endoscopic instruments 166 and 168 do not provide enough tactile sensation to the physician for the physician to be able to feel where the retainers 130 are located.

The first task for the physician is how to identify section 144, differentiate it from sections 142 and 146 and then center section 144 upon opening 160. If section 144 is provided with markers 154, as shown in FIGS. 1A, 1C the physician can identify section 144, differentiate it from sections 142 and 146 and then pull the suture through until section 144 is centered upon opening 160.

The next task for the physician is finding and identifying the needle associated with the suture exiting on the right side of the opening 160. Note that section 142 of the suture which is located on the right of opening 160 leaves visual field 164. Everything outside the dashed circle is invisible to the physician without moving the endoscope. Unless needle 112 is marked in some way, the physician may assume, incorrectly that needle 112 is associated with section 142 of self-retaining suture system 100. However, if needle 112 is marked as shown in FIG. 1A, then the physician can identify needle 112 as the incorrect needle.

The next task for the physician is to find and grasp needle 110. One way for the physician to acquire needle 110 is to follow section 142 of the suture all the way from opening 160 to the end. This is time consuming and the physician maybe come confused if sections 142 and 146 cross or move at some point. A faster technique would be for the physician to start from the visible segment 170 of section 142 of the suture within the visual field 164. However, unless section 142 of the suture thread is marked in some way there is no way for the physician to be sure that visible segment 170 of the suture is part of section 142. Likewise the physician cannot tell whether visible segment 172 of the suture is part of section 142 or part of section 146. If section 142 is marked in some way, the physician may acquire section 142 at visible portion 170. If section 142 is marked in a way that indicates orientation of the suture the physician will be able also to know in what direction needle 110 lies from the visible portion 170 allowing the physician to acquire the needle 110 in the most expedient and accurate way. If needle 110 is also marked in some way, the physician may confirm that the physician has acquired the correct needle for the next step in the procedure. Thus, marking the suture, suture sections and/or needles reduces error and saves time.

Heterofunctional Self-Retaining Suture Systems

As discussed above, it is particularly desirable to mark and identify portions of a self-retaining system when there is a difference in the features/utility of different sections of the self-retaining suture. In the case of self-retaining sutures the difference in features between sections of the suture may be the presence, absence and orientation of retainers associated with the section. In FIG. 1A, the difference in function between the two arms of self-retaining suture system 100 is the length of retainers 130. However, the differences in features and/or utility between sections of a heterofunctional suture are not limited to the presence, absence and orientation of retainers and include such differences as needle length, needle diameter, needle configuration, needle tip configuration; needle attachment method, needle material, needle surface treatment, suture length, suture diameter, suture material, suture manufacturing process, suture coating, suture texture, suture surface treatment, associated pharmaceuticals, suture shape-memory features, suture strength, suture elasticity, suture hardness, suture absorbability, retainer configuration, retainer dimensions, retainer distribution, and retainer elevation. FIGS. 2A-2D show examples of heterofunctional sutures having two or more sections having different features according to embodiments of the present invention.

As shown in FIG. 2A, an example of a heterofunctional self-retaining suture system 210 includes two arms 212, 213 joined at a transition section 214. Each arm 212, 213, terminates in a needle 216, 217. The length of suture filament in arm 212 however is significantly shorter than the length of suture filament in arm 213. This heterofunctional self-retaining suture system is useful for example in a wound closure where a physician begins at the center point of the wound and the sutures towards one end of the wound with one arm of the suture and towards the other end of the wound with the other arm of the suture. Usually a physician is more comfortable suturing in one direction rather than the other. Thus with the heterofunctional self-retaining suture system 210 of FIG. 2A, the physician may commence closer to one end of the wound instead of in the center of the wound. Thus the physician can perform more suturing with arm 213 in the preferred direction and less suturing with arm 212 in the less preferred direction.

As shown in FIG. 2B, another example of a heterofunctional self-retaining suture system 220 includes two arms 222, 223 joined at a transition section 224. Each arm 222, 223, terminates in a needle 226, 227. The suture filament in arm 222 is, in this embodiment, significantly thicker than the thickness of the suture filament in arm 223. In addition needle 226 of arm 222 is correspondingly larger than needle 227 of arm 223. This heterofunctional self-retaining suture system is useful for example in a wound closure where a physician uses one arm of the suture to close deeper tissue and uses another arm of the suture to close superficial tissue. Typically, it is preferable to use a finer suture for the superficial closure to reduce tissue reactivity to the suture and provide enhanced cosmesis. With the heterofunctional self-retaining suture system of FIG. 2B, the physician may first utilize arm 222 for the deep wound closure, where the need for strength is a more significant factor, and may then use arm 223 for closing the surface of the wound, where the need for reduced tissue reactivity and enhanced cosmesis are more significant factors.

The difference in function between the arms in a bidirectional self-retaining suture system may be due to differences in the needles (or other devices attached to the filament) rather than the suture filament itself. For example, as shown in FIG. 2C, another exemplary heterofunctional self-retaining suture system 230 includes two arms 232, 233 joined at a transition section 234. Each arm 232, 233, terminates in a needle 236, 237. The suture filament in arm 232 is the same thickness and length as the suture filament 233 and has a similar retainer configuration (retainers in each arm oriented to allow deployment in direction of the needle of that arm and resist movement in the opposite direction). However, arm 232 includes a straight needle 236 whereas arm 233 includes a curved needle 237. Different surgical needles are used by physicians for different suturing, tissue approximation and tissue elevation techniques thus it is useful to have facility to use different techniques provided in one self-retaining suture. With the heterofunctional self-retaining suture system 230 of FIG. 2C, the physician may utilize straight needle 236 of arm 232 using one technique and utilize curved needle 237 of arm 233 using a different technique.

Heterofunctional self-retaining suture systems are not limited to two arms (dual-armed suture). A heterofunctional self-retaining suture system may have more than two arms. Other multiple-arm sutures may include two, three, four, five or more arms. As shown in FIG. 2D, another example of a heterofunctional self-retaining suture system 240 includes three arms 241, 242, 243 joined at a transition section 244. Each arm 241, 242, 243 terminates in a needle 245, 246, 247. Arms 242 and 243 have the same type of filament and needle. The suture filament in arm 241 is however significantly thicker than the thickness of the suture filament in arms, 242, 243. In addition needle 245 of arm 241 is correspondingly larger than needles 246, 247 of arms 242, 243. This heterofunctional self-retaining suture system is useful for example in a wound closure where a physician uses one arm of the suture to close deeper tissue and uses another arm of the suture to close superficial tissue. Typically, it is preferable to use a finer suture for the superficial closure to reduce tissue reactivity to the suture and provide enhanced cosmesis. With the heterofunctional self-retaining suture system of FIG. 2B, the physician may first utilize arm 241 for the deep wound closure, where the need for strength is more significant, and may then use arms 242, 243 for closing the surface of the wound, where tissue reactivity and cosmesis are more significant.

Figure 2E:
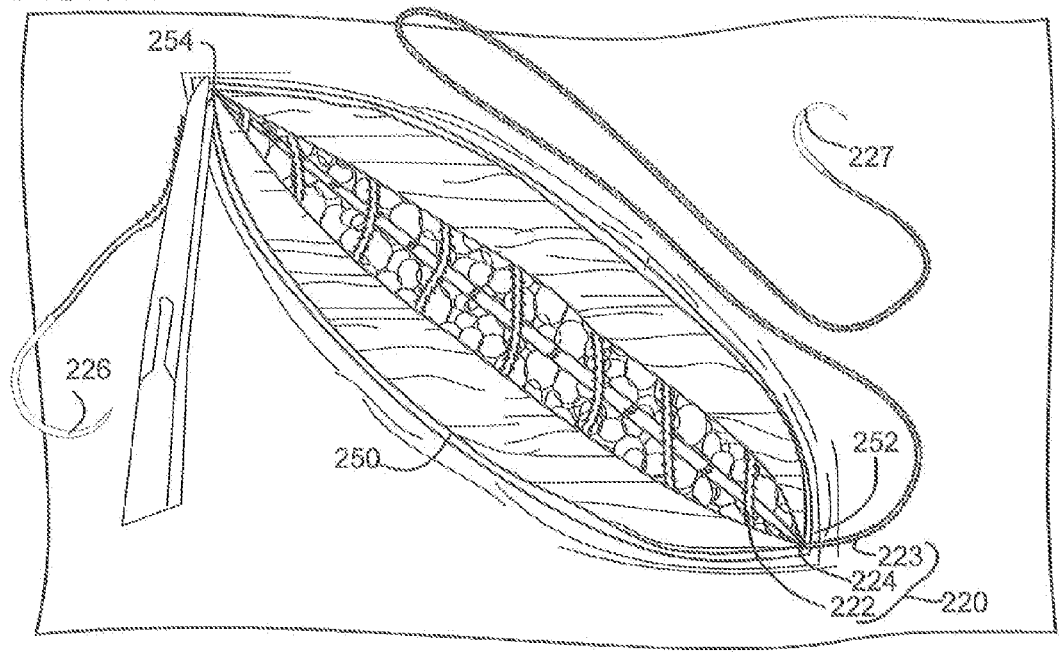
FIGS. 2E-2F show examples of an application of a heterofunctional suture such as the heterofunctional suture of FIG. 2B according to an embodiment of the present invention.
Figure 2F:
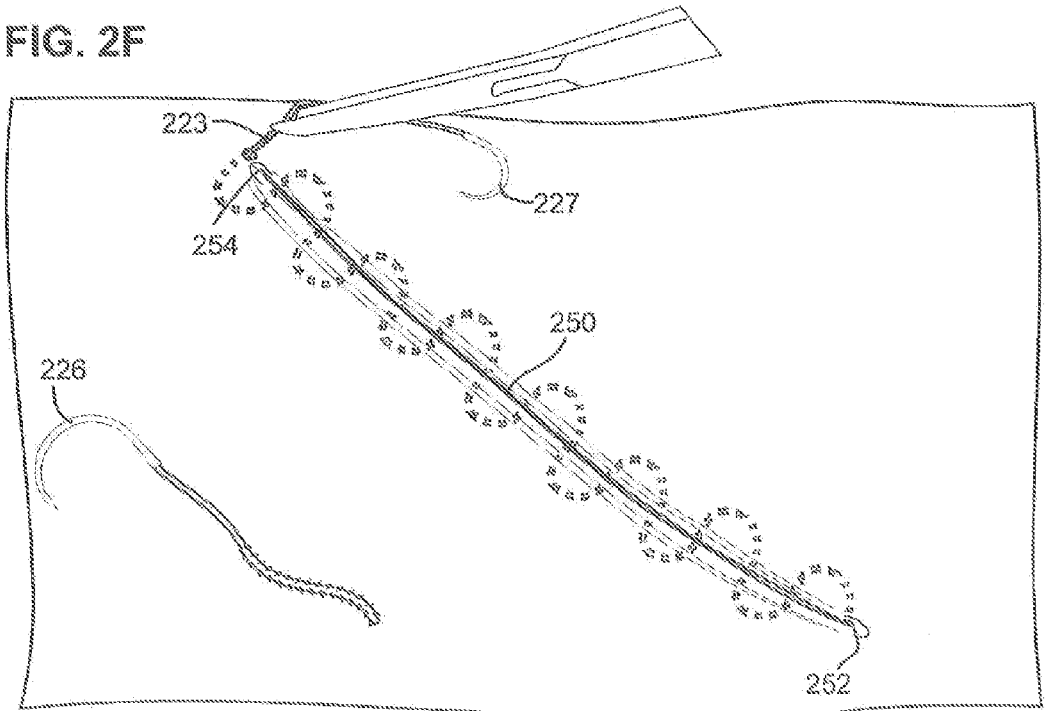

FIGS. 2E and 2F show an example of a multiple-layer wound closure using a heterofunctional suture such as shown in FIG. 2B. As shown in FIG. 2B, heterofunctional self-retaining suture system 220 includes two arms 222, 223 joined at a transition section 224. Each arm 222, 223, terminates in a needle 226, 227. The suture filament in arm 222 is significantly thicker than the thickness of the suture filament in arm 223. In addition needle 226 of arm 222 is correspondingly larger than needle 227 of arm 223. As shown in FIGS. 2E and 2F, the physician closes the wound 250 beginning at a first end 252 and suturing towards the second end 254. The physician closes wound 250 in two layers. The physician first utilizes arm 222 for the deep wound closure (shown in FIG. 2E) and then uses arm 223 for closing the surface of the wound (shown in FIG. 2F). One advantage of this closure technique is that the surgeon can select which end (252 or 254) of the wound 250 to commence the closure and can the close the wound suturing in one direction, thus the physician can suture exclusively with their dominant hand and avoid changing from one side of the patient to the other during suturing.

Referring now to FIG. 2E which shows closure of the deep tissue layer. The physician passes needle 226 through the edge of the subcuticular layer, deep dermis and the soft tissue and draws arm 222 through the wound until the retainers of arm 223 begin to engage the tissue. The physician closes the deep layers using a helical or sinusoidal stitch configuration. Because needle 226 is relatively larger, the physician can take large bites through the tissue in this deep layer closure which allows a greater tension force to be applied to the tissue to close the wound without tearing the tissue or causing ischemia. The surgeon may tension arm 222 as the suturing progresses from end 252 to end 254 thereby progressively closing the wound 250. If necessary, the physician may make a subcutaneous pass with needle 227 to set more retainers of arm 223 in tissue to prevent pull through while closing the deep layers of tissue with arm 222. The suture filament of arm 222 is relatively thicker and thus allows for application of greater tension to close the wound 250 than would otherwise have been possible.

Referring now to FIG. 2F which shows the superficial portion of the wound closure. As shown in FIG. 2F, the physician passes through the subcutaneous tissue taking bites on alternate sides of the wound. The depth of the needle as it enters the tissue and emerges should be the same for each bite and on the opposite side of the wound. The radius of the bite is determined by the radius of needle 227. The bites are thus smaller than the bites made with arm 222 and needle 226. Thus less tension can be applied to the wound 250 by arm 223. However, the majority of the tension required to close wound 250 has already been applied by arm 222. The smaller diameter filament and smaller bites of needle 227 are therefore sufficient to close the superficial wound as shown in FIG. 2F.

Additionally, because arm 223 is made of a relatively smaller diameter filament, there will be less tissue reactivity to the suture filament. This will enhance cosmesis and reduce adverse results such as splitting and the like. As the wound closure progresses the physician may wish to apply further tension to the deep layer suture arm 222. When suitable tension has been achieved the physician may make a J-loop pass with the suture and cut off the remaining suture and needle of arm 222. When the physician finished the superficial closure, the physician takes the last subcutaneous bite through tissue 2 cm beyond the second end 254 of the wound 250 exiting through the skin The physician pushes down on the tissue and cuts of the remaining needle and suture flush with the skin Visible Indicia for Self-Retaining Sutures As discussed above, it is particularly desirable to mark and identify portions of a heterofunctional suture system where different sections of the suture have different features such as in dual-arm self-retaining suture systems. In heterofunctional self-retaining suture systems the difference in function between sections of the suture may be the presence, absence and/or orientation of retainers. To serve the purpose of allowing a physician to identify and differentiate suture sections, the suture markers should be readily recognized and distinguished by the physician under the conditions in which the suture is to be used. For example, in microsurgery applications, markers may be used that are visible under the microscope, but not necessarily visible to the naked eye. Likewise in endoscopic applications, markers should be used that are visible through the endoscope and associated display system. If the suture will be used with fluoroscopic visualization then the markers may include radiopaque markers. If the suture will be used with ultrasound visualization then the markers may include echogenic markers. Thus, different markers and different types of markers may be appropriate under different circumstances depending upon the circumstances of the procedure and the scanning/imaging/visualization technology utilized in the procedure.

The markers can be provided in various forms that may be identified and distinguished from one another. The markers may comprise distinguishable, patterns, shapes, lengths, colors sizes, directions and arrangements. The markers can include different colors such as red, green, orange, yellow, green, blue etc. Such colors may be used in a uniform density or varying density in which case the graduation of color density may be used to designate e.g. an orientation. The markers may be included along the entire length of the self-retaining suture system, at a number of discrete points, or only at the ends or transition section of the self-retaining suture. In some cases it may be desirable to use a color for markers that is uncommon in the operative environment. For example, it may be desirable to use green markers because green is not common in the human body. In endoscopic applications using green is advantageous because the video system can be programmed to emphasize green and enhance marker visualization without interfering with the remainder of the image.

The markers can be formed by various conventional methods. For example, the markers can be coated, sprayed, glued, dyed, stained, or otherwise affixed to the self-retaining suture systems or components thereof. Alternatively, markers can be made by treating a surface of the suture system to make an observable change in surface characteristics such as by branding, texturing, embossing, stamping and the like. Alternatively, the markers may be an integral part of the material from which the self-retaining suture system is formed—such as by forming a self-retaining suture system by joining different sections of suture filament of different colors. The markers may be provided on one or more of the suture filament, the needles, or another item, such as a pledget, associated with the self-retaining suture system or section of the filament. In some case markers may be formed as an integral part of the retainers of a self-retaining suture, such as by creating retainers of a particular color of material or by exposing a particular color of material—different retainer patterns may be used to differentiate different sections of the self-retaining suture.

FIGS. 3A-3I illustrate some of the many ways in which markers on the suture filament may be used to identify one section of suture and distinguish it from other sections. The markers may be used alone or in combination with other of the markers. The markers may identify, differentiate and/or delineate sutures and/or sections of suture having different features.

Figure 3A:
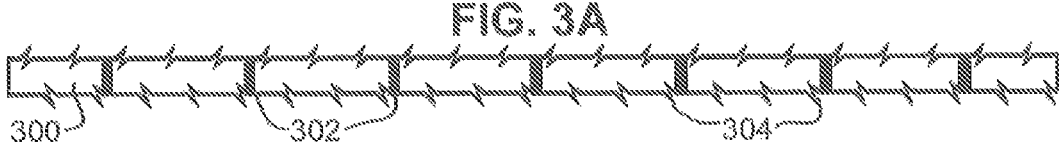
FIGS. 3A-3I show examples of suture markers which may be associated with one or more sections of a suture having different features according to embodiments of the present invention.

FIG. 3A shows a section 300 of a self-retaining suture filament. The section 300 is marked at regular intervals with bands 302 of a solid color distinguishable from the color of the filament. The bands serve to identify section 300 but, standing alone, do not indicate the orientation of the retainers 304 within the section 300.

Figure 3B:
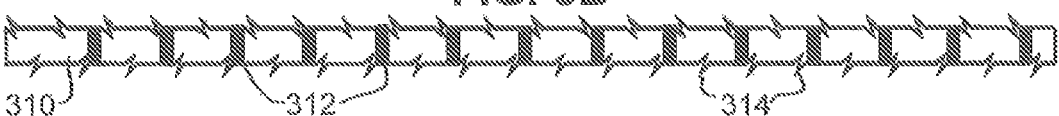

FIG. 3B shows a section 310 of a self-retaining suture filament. The section 310 is marked at regular intervals with bands 312 of a solid color distinguishable from the background color of the filament. The bands serve to identify section 310 but, standing alone, do not indicate the orientation of the retainers 314 within the section 300. The interval between bands 312 of section 310 is significantly less than the interval between the bands 302 of section 300. The different arrangement of bands 312 and bands 302 may be visually observed and thus allows the physician to distinguish section 310 from section 300.

Figure 3C:
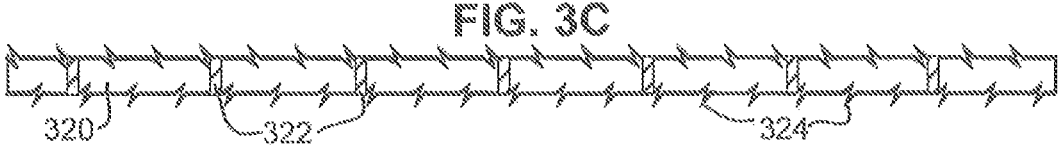

FIG. 3C shows a section 320 of a self-retaining suture filament. The section 320 is marked at regular intervals with bands 322 of a solid color distinguishable from the background color of the filament. The bands serve to identify section 320 but, standing alone, do not indicate the orientation of the retainers 324 within the section 320. The color or color density of bands 322 of section 320 is distinguishable from the color (or color density) of bands 302 of section 300 (represented by shading in FIG. 3C by the shading of bands 322). The different color and/or color density of bands 322 and bands 302 may be visually observed and thus allows the physician to distinguish section 320 from section 300.

Figure 3D:
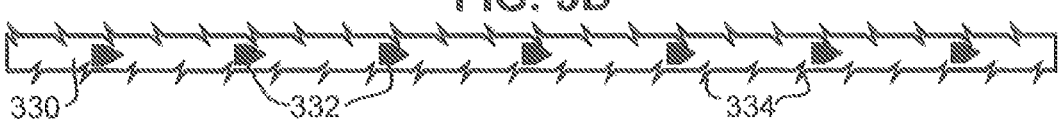

FIG. 3D shows a section 330 of a self-retaining suture filament. The section 330 is marked at regular intervals with shapes 332 of a solid color distinguishable from the background color of the filament. The shapes have a discernible orientation which is asymmetric relative to the longitudinal axis of section 330. For example shapes 332, can be regarded as pointing in the direction of the apex on the right side. Thus shapes 332 can be used to identify section 330 and also to indicate the orientation of the retainers 304 within the section 300. The direction in which the markers point can be assigned by convention, however, in the section 330, shapes 332 point in the direction in which the section 330 of self-retaining suture filament may be deployed through tissue without resistance by retainers 334. As part of a self-retaining suture system the shapes would thus point along the filament in the direction of the deployment needle associated with the arm including section 330. The different arrangement of bands 332 and bands 302 may be visually observed and thus also allows the physician also to distinguish section 330 from section 300.

Figure 3E:
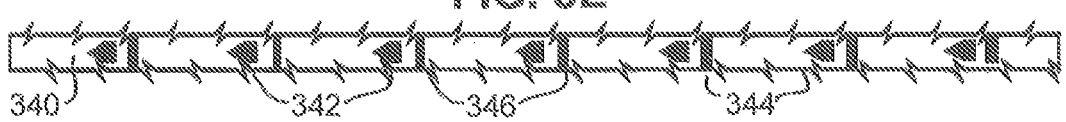

The shapes of FIG. 3D may be used to indicate the orientation of a self-retaining suture filament. FIG. 3E shows a section 340 of a self-retaining suture filament oriented in the opposite direction to section 300. The section 340 is also marked at regular intervals with shapes 342 of a solid color distinguishable from the background color of the filament. Shapes 342, can be regarded as pointing in the direction of the apex on the left side. However, without more section 340 could be confused with section 330. Thus an additional feature is used to differentiate section 340 from section 330. As shown in FIG. 3D, section 340 is marked at regular intervals with bands 346 of a solid color distinguishable from the color of the filament in addition to shapes 342. Thus section 340 can be identified and distinguished from section 330 and the orientation of the filament in each of sections 330, 340 may be determined from the markers.

Figure 3F:
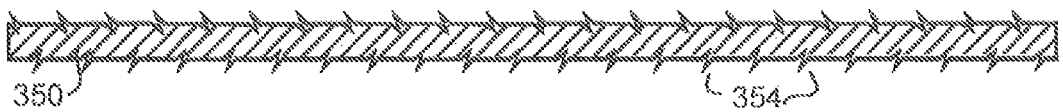

FIG. 3F shows a section 350 of a self-retaining suture filament. The section 350 is formed of a material having a solid color or marked with a solid color that is distinguishable from other sections of the suture. The color serves to identify section 350 but, standing alone, does not indicate the orientation of the retainers 354 within the section 350. The color may be visually observed and thus allows the physician to distinguish section 350 from a section of a different color. Different colors may be used to identify sections of a self-retaining suture system either by joining different colored sections of suture after they have been colored or by treating different sections of the same filament to have different colors such as dying a section of a filament to add color, or treating a section of a filament to remove color.

Figure 3G:
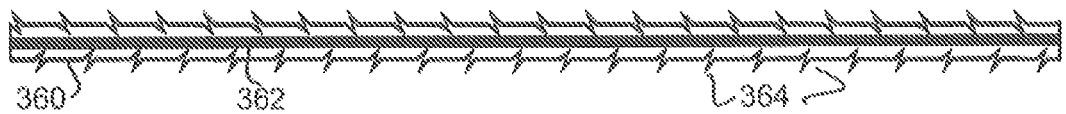

FIG. 3G shows a section 360 of a self-retaining suture filament. The section 360 is marked with a longitudinal line 362 of a solid color distinguishable from the background color of the filament. The longitudinal line 362 serves to identify section 360 but, standing alone, does not indicate the orientation of the retainers 364 within the section 360. The longitudinal orientation of line 362 is readily distinguishable from the bands 302 of section 300. The different orientation of line 362 and bands 302 may be visually observed and thus allows the physician to distinguish section 360 from section 300. Longitudinal lines, such as line 362, but having different thickness, patterns or colors, may also be used to distinguish one section of filament from another. of different thickness.

Figure 3H:
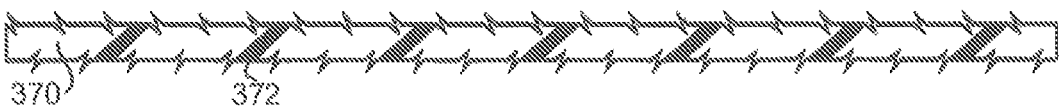

FIG. 3H shows a section 370 of a self-retaining suture filament. The section 370 is marked with a spiral 372 of a solid color distinguishable from the background color of the filament. A spiral may be used to indicate orientation of a filament because a spiral may be left-handed or right-handed. The different handedness of the spiral may be visually observed and thus allow the physician to determine the orientation of the retainers. The handedness of the spiral 372 may however be more difficult to discern and harder to associate with a particular orientation of retainer than for example a simple shape such as shown in FIGS. 3D and 3E.

Figure 3I:
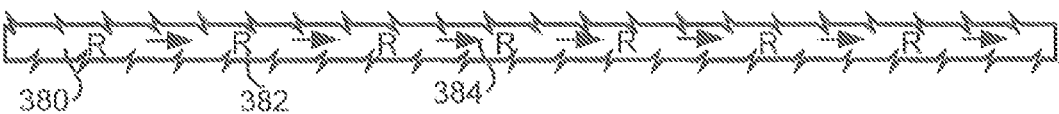

FIG. 3I shows a section 380 of a self-retaining suture filament. Section 380 is marked with typographical characters (such as "R" for right and "L" for left). Characters such as alphanumeric characters 382 and arrows 384 may be used to identify sections of suture and the orientation of the retainers in that section if they are observable by the physician. However, under many circumstances the suture will be too fine for such markers to be discernible by the physician with the level of magnification available utilized during the surgical procedure.

Visible/Recognizable Indicia for Needles and/or Pledgets

As described above, the needle or another object associated with a section of a heterofunctional suture filament may be marked to enable that section to be identified and distinguished from other sections instead of, or in addition to, marking the suture filament itself. FIGS. 4A-4E illustrate alternative markers that may be placed upon needles and/or pledgets of self-retaining suture systems. It is to be understood that such markers, and, in fact, some other markers described herein, if desired, can be present as an image in the visible light wavelength range or in the non-visible wavelength range. In the non-visible (but otherwise recognizable) wavelength range, a detector would be used to located and image the non-visible marker so that the doctor would have the use and benefit of this marker.

Figure 4A:
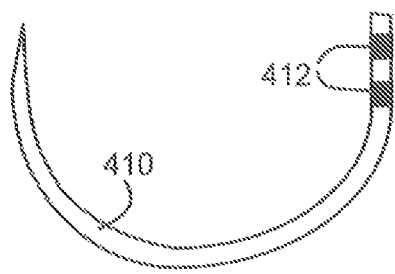
FIGS. 4A-4E show examples of needle and pledget markers which may be associated with one or more sections of a suture having different features according to embodiments of the present invention.

FIG. 4A shows a semicircular needle 410 having two bands 412 with different visual/recognizable characteristics than the remainder of the surface of needle 410. The bands 412 may be colored sections, or sections treated to reduce or change reflection of light. A different number, color or placement of bands may be used to differentiate one needle from another. The bands 412 may, for example be printed sections of the needle surface, or oxidized sections of the needle surface.

Figure 4B:
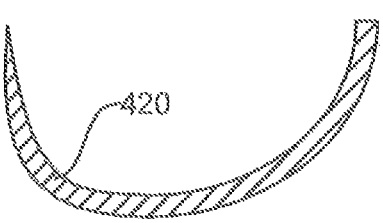

FIG. 4B shows a compound curve needle 420. The surface of needle 420 exhibits a different visual characteristic that the surface of e.g. needle 410. Needles typically have the reflective silver color characteristic of surgical steel. Different visual characteristics may be achieved by using a different metal, or by coloring, treating or changing the reflectivity of the steel needle in some way such as oxidation, heat treatment and the like. Then one needle can be silver in color and the other needle can be black in color.

Figure 4C:
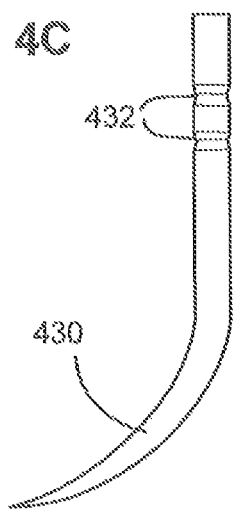

FIG. 4C shows a quarter-circle needle 430. Needle 430 has two circumferential grooves 432 which can be observed on the shank of the needle. A different number, size, or placement of grooves may be used to differentiate one needle from another. Other structural features may be cut into or added onto the surface of the needle by processes such as for example engraving or stamping so long as they features can be differentiated and do not interfere with the function of the needle.

Figure 4D:
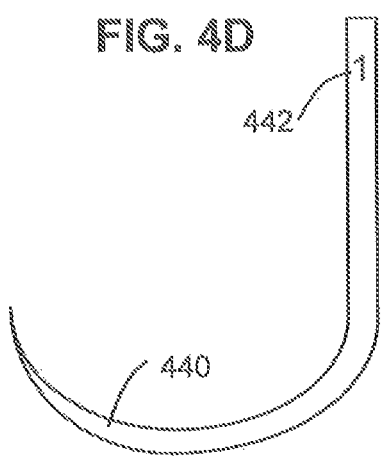

FIG. 4D shows a J-shaped needle 440. Needle 440 is marked with an alphanumeric character 442. Needles may be marked with such characters so long as the characters may be discerned and differentiated by the physician. The characters may be marked on the needle using any of the above techniques.

Figure 4E:
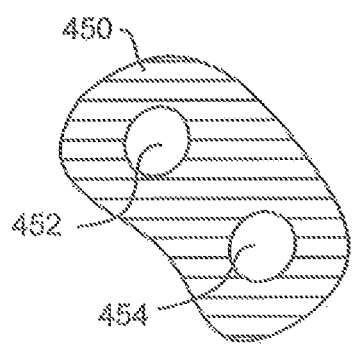

FIG. 4E shows a pledget 450 which may be associated with a section of suture by passing the filament through holes 452, 454. Pledgets may be marked using any of the means previously discussed to identify and differentiate sections of suture and indicate the orientation of retainers in the section. Pledgets and the like may be permanently attached or removably attached to a suture or section of the suture.

Variable Indicia of a Suture Condition

Visual/recognizable markers may be used for other functions instead of, or in addition to, identifying and differentiating sections of a heterofunctional suture and indicating the orientation of the suture. Markers may also be utilized to indicate other features or conditions of the suture. A marker indicative of a fixed feature such as the material from which the suture is made could be in the form of a color code or the like that provides a visual/recognizable clue to the physician regarding the suture he is using without having to check the packaging. Non-sterile portions of the suture packaging may be removed by a physician's assistant, for example, with the physician observing or not observing the labeling. Thus, a fixed marker associated with the suture may be useful for the physician to confirm that they are using the suture they requested. Again, the marker can provide an image in the visible and/or non-visible light range.

A marker that is indicative of a condition of the suture must undergo a discernible change in appearance or other recognizable characteristic in response to a change in the condition. For example, in endoscopic applications where long instruments are used through ports or even operated remotely, it can be difficult or impossible for the physician to feel the tension applied to the suture by the instruments or by the suture to tissue. To replace the reduced or missing haptic feedback, it is advantageous to provide a variable marker indicative of the tension in the suture. The variable marker provides a visual or recognizable cue that can be observed by the physician through the endoscope (or recognized by other means).

Figure 5A:
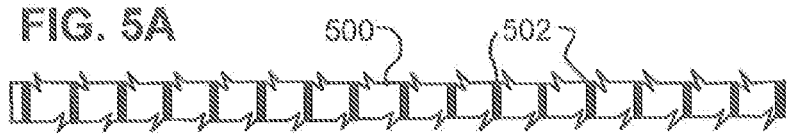
FIGS. 5A-5H show examples of suture markers and needle markers which may be associated with a suture to indicate a condition of a suture, such as tension, according to embodiments of the present invention.
Figure 5B:
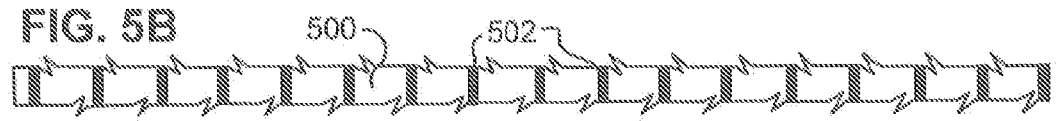

In a simple case, as shown in FIGS. 5A and 5B, a self-retaining suture filament 500 is provided with a plurality of bands 502 spaced at regular intervals along the suture filament. Self-retaining filament 500 is somewhat elastic and therefore stretches in response to tension applied to the suture. Thus, when tension is applied to the suture filament in FIG. 5A, it stretches to the configuration shown in FIG. 5B. However, without bands 502, it may be difficult or impossible for a physician to recognize and/or observe the extension of filament 500. The spacing of bands 502 increases as self-retaining suture filament 500 stretches thereby providing a visual cue to the physician regarding the extension of the filament. Because the stretching of the filament is related to the tension in the filament, the spacing of the bands provides the physician with a visual cue as to the tension in the filament. Note that in this case, the markers do not themselves change, and the change in spacing of the bands is dependent upon the elongation of the suture filament. Additionally, the band could partially cover a retainer and partially cover the suture filament. Upon stretching of the suture, the filament would stretch, and the retainer would not causing misalignment between the band portion on the retainer and the band portion on the filament. This misalignment would indicate that the filament was in tension.

Figure 5C:
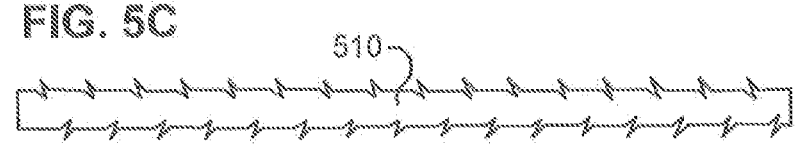
Figure 5D:
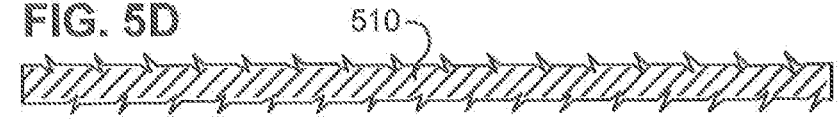

An alternative self-retaining suture filament 510 is shown in FIGS. 5C and 5D. Filament 510 is provided with a variable marker that changes to a visual state in response to tension in suture filament 510. The marker may be a surface marker or may be a feature of the material of which filament 510 is made. Moreover, the marker may cover the entirety of the filament or may be restricted to particular sections of the filament. As shown in FIGS. 5C and 5D, when tension is applied to filament 510 the marker changes from the visual appearance of FIG. 5C (illustrated as white) to the visual appearance of FIG. 5D (illustrated as shaded). The change in visual appearance may be a change in color, light transmission, light reflectivity etc. The change in visual appearance may be a change in appearance not observable by the naked eye, but that can be visualized using the endoscope or another visualization system in use. Such a change can include a change in light polarization, or optical properties at wavelengths invisible to the naked eye but observable using a suitably configured video camera.

For example, markers can be made of two colors that under stress blend and present a third color or various intensities of shades of a different color depending upon the degree of stress. The two different colors can be placed at different depths of a suture and when the suture is stressed the colors blend or overlap each other to present different colors. The different depths of the suture can be made of different materials that stretch to different degrees when the suture is stressed and thus the different colors at different depths would blend or overlap each other to present a different color. The different levels can be co-extruded to provide, as desired, each layer with different types of suture material and different colored markers. Further the different colored markers can be placed side by side on the surface of the suture and when the suture is under stress the colors blend or overlap or become differently oriented relative to each other such that they present a different color or shade and the color or shade may be dependent upon the degree of stress that the suture is under. Instead of different colors, different patterns can be used and then the patterns overlap or otherwise combine due to stress being placed on the suture, a different pattern such as an interference or interfering pattern can be presented.

Figure 5E:
Figure 5F:
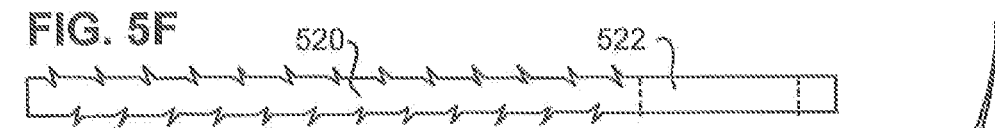

An alternative self-retaining suture filament 520 is shown in FIGS. 5E, 5F. Filament 520 is provided with a variable marker in the form of a mechanical feature 522 which undergoes a visible physical change in response to the application of tension on the suture. As shown in FIGS. 5E and 5F, when tension is applied to filament 520 the mechanical feature 522 changes from the configuration in FIG. 5E to the configuration of FIG. 5F. The change in structural appearance is selected such that it is observable by the physician under the conditions in which the suture is used. The change in structural appearance may be a change in appearance not observable by the naked eye but that can be visualized using the endoscope or other visualization system in use. Preferably the change in structural appearance does not interfere with the function of the suture.

Figure 5G:
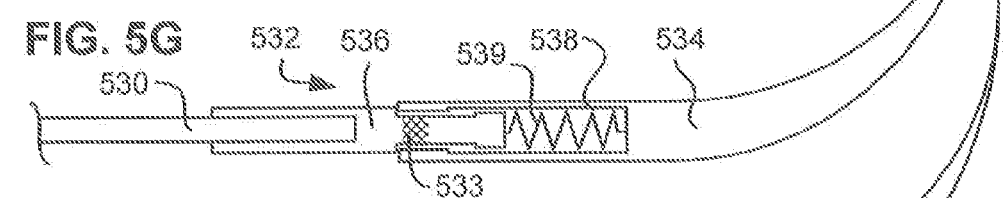
Figure 5H:
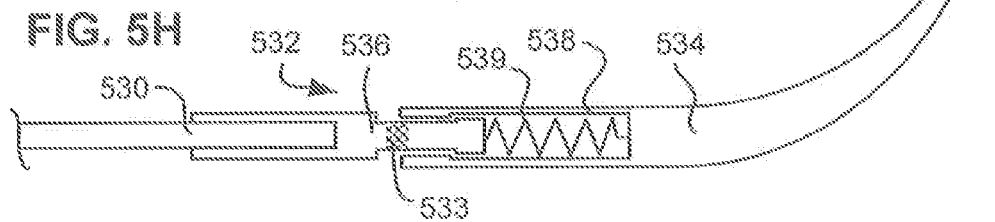

As shown in FIGS. 5G and 5H, a variable marker may form part of a needle or other device fixed to the suture filament rather than being part of the filament itself. As shown in FIGS. 5G and 5H, a mechanical sensor 532 is included in a needle 534 to indicate the tension applied to a filament 530. Mechanical sensor 532 includes a cap 536 swaged to filament 530, cap 536 is received in a cavity 538 of needle 534. A device, such as a spring 539, that elongates in response to tension is positioned between the cap 536 and the end of the cavity 538. When tension is applied to the filament 530, spring 539 extends, and cap 536 slides out of cavity 538 revealing a marker 533 that was previously concealed inside cavity 538. The spring constant of spring 539 is selected such that visual indicator becomes visible when a desired tension is reached. A different spring may be used for sutures, and/or applications requiring a different maximum tension. The mechanical sensor 532 is indicative the tension applied to the suture by the needle. Similar mechanical sensors may be attached in line with the suture filament at other locations where an indication of tension is desired. Instead of a spring, the filament 530 could be directly connected to the needle in cavity 538. As the filament stretches, the marker 533 would become extended from the cavity 538 as seen in FIG. 5H. Still further, the above embodiment could be located in the suture body where a marker extends from a cavity or from under a sleeve of a suture body when the suture is stressed.

Other passive mechanical sensors may indicate suture properties through means other than displaying a visible marker or optically detectable marker. For example, a wireless passive strain sensor may be incorporated into a suture or a needle or another device associated with the suture to allow remote sensing of the tension using a non-optical sensor. One such sensor is disclosed in Tan et al., "A wireless, passive strain sensor based on the harmonic response of magnetically soft materials" Smart Materials And Structures 17:1-6 (2008) which is incorporated herein by reference. Tan et al. disclose a sensor made of a ferromagnetic sensing element separated by a deformable elastic material from a permanent magnetic strip. Adjusting the strain applied to the sensor changed the distance between the sensor and the permanent magnet by deforming the elastic material. This change in distance created a detectable change in the harmonic response of the sensor to an alternating magnetic field. Thus a simple passive sensor provides a strain signal that can be detected remotely using an external magnetic field. Similarly passive strain sensors associated with the suture or needle can be read using other remote sensing technologies, such as ultrasound, fluoroscopy, and the like.

Active Indicia for Self-Retaining Sutures

Fixed or variable markers for suture filaments may also be provided by active systems instead of, or in addition to, other marking methods. Such active visible markers may be utilized to indicate features or conditions of the suture.

Figure 6A:
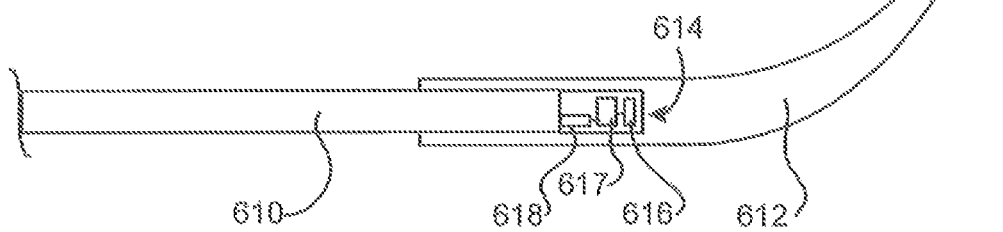
FIGS. 6A-6D show examples of active suture markers which may be associated with one or more sections of a suture to indicate features and/or conditions of the suture according to embodiments of the present invention.

FIG. 6A shows one simple example of an active visible suture marker. As shown in FIG. 6A, a suture filament 610 is swaged to a needle 612. An active marker system 614 is disposed inside the needle 612 adjacent suture filament 610. Active marker system 614 comprises a power source 616, a light controller 617 and a light source 618. Light source 618 is positioned adjacent suture filament 610 such that light from light source 618 may be directed into suture filament 610 and observed by the physician. The light signal will be visible within the suture filament along the length of the suture filament and will attenuate as it passes down the filament away from the light source depending upon the characteristics of the filament.

Light source 618 is controlled by light controller 617 which takes power from power source 616. Light controller 617 determines the characteristics of the light signal provided by light source 618. The light signal may be varied over time such as by turning it on, turning it off and/or flashing at different speeds. The light signal may also be varied in color if light source 618 is capable of producing light of different wavelengths. If power source 616 is a battery, the available power will limit the time that light source 618 may be operated. Thus, it will be desirable that light source 618 be activated by light controller 617 only at the beginning of the procedure utilizing suture filament 610. The activation may be achieved using a magnetic switch, mechanical switch, electromagnetic sensor or the like. In one embodiment, the light source can be an LED and the controller a sensor that measures stress, strain or tension. The LED and sensor can be made in a semiconductor chip. The power supply can be passive, such as in a passive RFID tag. Then a source of radiation may activate the RF power source to power the sensor and the LED light source. In some embodiments the sensor may comprise an accelerometer.

In a dual-armed suture system, another active marker system 614 may be provided in another needle swaged to the opposite end of suture filament 610. Where two active marker systems 614 are used, they may be differentiated based upon the characteristics of the light signals provided by the light source 618. For example, each light source may be controlled to provide light of a different wavelength than the other. Alternatively, one light source may provide a constant light signal whereas the other light source may provide a flashed light signal. If light signals from both light sources overlap in the suture filament, then the light signals may be attenuated by adjusting the power of the light signals, reducing the light transmission of the suture filament or placing a barrier such as an opaque section to block light transmission between one section of suture filament 610 and another section of suture filament 610.

An active marker indicative of a feature, such as the material of which a section of a heterofunctional suture is made, or the orientation of retainers in a particular section of a self-retaining suture, can be in the form of a color code or the like that provides a visual cue to the physician regarding the suture he is using without having to check the packaging. Non sterile portions of the suture packaging may be removed by a physician's assistant for example with the physician observing the labeling. Thus an active visible marker associated with the suture may be useful for the physician to confirm they are using the suture they requested.

Figure 6B:
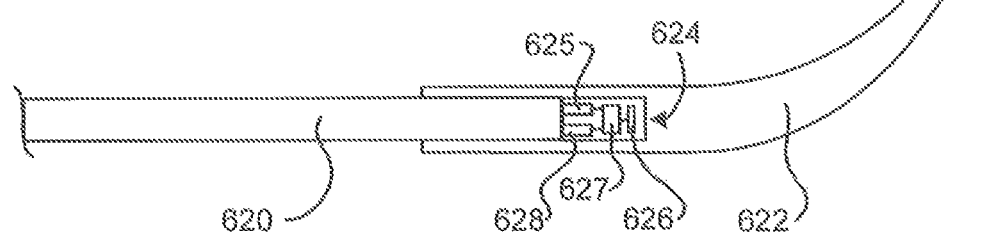

Active visual markers may also be utilized to indicate conditions of the suture. An active visual marker that is indicative of a condition of the suture undergoes an observable change in appearance in response to the condition. Thus, in one example a light signal may be modulated in response to tension in a suture providing a visual cue that can be observed by the physician. FIG. 6B shows one simple example of an active visible suture marker indicative of a variable condition. As shown in FIG. 6B, a suture filament 620 is swaged to a needle 622. An active marker system 624 is disposed inside the needle 622 adjacent suture filament 620. Active marker system 624 comprises a power source 626, a light controller 627 and a light source 628. Active marker system 624 also includes a sensor 625 for monitoring a condition of suture filament 620. Light source 628 is controlled by light controller 627 which takes power from power source 626. Light controller 627 controls the characteristics of the light signal provided by light source 628. The light signal may be varied over time such as by turning it on, turning it off and/or flashing at different speeds. The light signal may also be varied in color if light source 628 is capable of producing light of different wavelengths.

The light signal provided by light source 628 is modulated by controller 627 in response to the output of sensor 625. Thus the light signal provided by light source 628 is modulated in response to the condition monitored by sensor 625. For example, sensor 625 may be a force sensor, such as an accelerometer, and controller 627 (also part of the accelerometer, for example, in this embodiment) may control light source 628 so that no light signal is provided to suture filament 620 until the sensor indicates that a threshold tension in filament 620 has been achieved. When the tension passes the threshold then controller 627 turns on light source 628 providing a cue to the physician. Alternatively, the light source may be on initially and then flashed when the tension reaches the threshold.

Figure 6C:
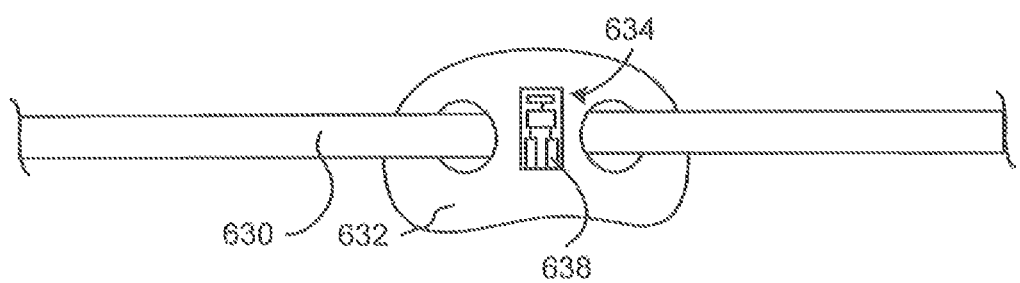
Figure 6D:
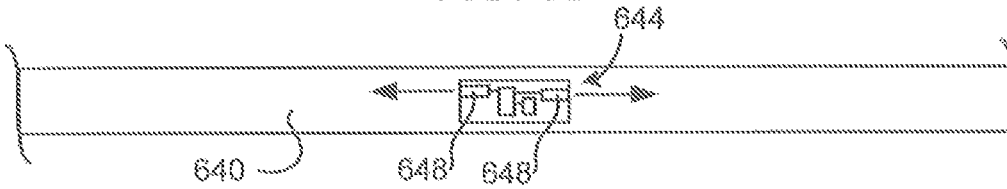

As shown in FIG. 6C, an active marker system need not be part of a needle. An active marker system 634 may, for example, be provided in a pledget 632 or another device attached to or associated with suture filament 632. The active marker system 634 may provide a light signal utilizing suture filament 630, pledget 632 or directly from light source 638 to the physician. Alternatively, as shown in FIG. 6D, some, or all of an active suture marker system 644 may be miniaturized and embedded within a suture filament 640.

Where an active marker system is provided other than at the end of a suture filament as shown in FIGS. 6C and 6D, the active marker system may advantageously provide two light signals—a first signal indicating the suture filament in a first direction from the active marker system and a second signal indicating the suture filament in a second direction. The two light signals may, for example, be provided by two light sources, one source pointing in each direction along the filament from the active marker system. Thus, as shown in FIG. 6D, an active marker system 644 embedded in a suture filament 640 may include two light sources 648 pointing in opposite directions along suture filament 640 as shown.

Machine-Readable Indicia for Self-Retaining Sutures

As described above, a suture filament may be provided with visible markers indicative of features or conditions of the suture filament and/or indicative of particular sections of a suture filament having different features. Such markers are observed by the physician under the operative conditions—which may include e.g. magnification in microsurgical procedures and video display—including wavelength translation/enhancement in endoscopic procedures. However, where machines are available to read, scan and decode suture markers, such markers need not be visible markers or markers that may be visually decoded. The markers may be designed to be machine-readable instead of, or in addition to, being directly visualizable by the physician. While visible markers may be identified and decoded utilizing a video tracking and analyzing system, different visible markers may be more suitable for machine recognition. Moreover, non-visible suture markers or coding may also be used by a computer system to identify sections and conditions of sutures. When the suture sections and/or conditions have been recognized and assessed by the system, information about the sections and conditions of the suture may be provided to the physician by the system. The information may be provided to the physician over any available display system, including a visual, aural or haptic display.

FIG. 7A show features of an endoscopic surgical system (generally) 720 which utilize machine-readable markers to identify sections and conditions of a suture filament 700. Endoscopic surgical system 720 comprises a patient-side system 730 which interfaces with the patient at the operative site and a physician-side system 740 which interfaces with the physician 710. The patient-side system 730 includes an imaging system such as an endoscope, fluoroscope, ultrasound or the like and one or more surgical effectors, such as surgical instruments, catheters, and the like. The physician-side system 740 includes a display system 742 such as video screen for providing information to the physician 710 and a control system 744 such as a joystick or the As shown in FIG. 7A, the patient-side system 730, comprises an endoscope 732 having a light output 733 and two imaging devices in the form of CCDs 734, 735 and associated optics for imaging the operative field. CCDs 734, 735 are separated by the width of endoscope 732 and thus provide a binocular image comprising two separate views of the operative filed. These two views may be utilized to generate a three-dimensional image of the operative field and also to generate three-dimensional tracking data for objects and markers which can be identified in each image. The patient-side system 730 also includes two surgical instruments 736, 737 for manipulating suture filaments, needles and tissue. Surgical instruments 736, 737 are shown as endoscopic instruments and may be manually-operated or servo-operated. Surgical instruments 736, 737 may be forceps, needle drivers, cautery, graspers and/or any of the wide range of surgical instruments available as suited to a particular procedure.

As shown in FIG. 7A, the physician-side system 740 comprises a display system 742 which provides information to physician 710. The display system 742 may include visual, audio and haptic display components. The physician-side system 740 also comprises a physician control interface 744 for allowing physician 710 to control the system including controlling movement of surgical instruments 736, 737. The physician control interface 744 may include a keyboard, mouse, joysticks or the like. The physician control interface 744 may include force feedback controllers which also serve to provide information to the physician as part of the physician display system. The physician-side system also includes a suture information system 746 which receives information from the endoscope and decodes it to generate information about the suture. The physician-side system also includes a display processing system 748 for receiving image information from endoscope and integrating it with other information for display to physician 710 by display system 742.

As shown in FIG. 7A, suture information system 746 receives image data from CCDs 734, 735 of patient side system 730. Suture information system 746 includes a left image decoder 750 which receives and decodes image data from CCD 734 and right image decoder 751 which receives and decodes image data from CCD 735. Image decoders 750, 751 identify suture markers in the video image data received from a CCD of 734, 735 of endoscope 732. Marker tracking system 752 receives marker identity and position data from image decoders 750 and 751. The position of a marker will differ slightly between the left image and the right image. From the difference in positions, marker tracking system 752 can identify the location of the markers in three dimensions. In one embodiment, suture information system 746 includes a suture tension calculator 754 which calculates the tension in the suture from the marker tracking information. The suture tension information and marker tracking information is provided to suture data output system 756. Suture data output system 756 provides the information to display processing system 748 which integrates the suture data with the other information received form the patient-side system.

In the embodiments of FIGS. 7A, 7B, and 7C the system and for example, the suture tension calculator, in addition to causing a visual, audio or haptic or other alarm signal to be generated and sent to the physician can place limits on the maximum amount of stress which can be placed on the suture. Further as each type of suture has different characters, the system can use a database to identify the amount of stress that any type of suture can be placed under and can cause the system to limit the amount of stress that the doctor can place on the suture depending upon the type of suture being deployed in the patient during that procedure. Further the system can cause various levels or intensities of sound, light, or haptic feedback to occur depending on the amount of stress on the suture and the type of suture being deployed at the time in the patient. Again the various characteristic of each suture can be stored in a database in the system and the system can recognize the type of suture being deployed and adjust the feedback and/or the maximum stress the suture can be placed under.

FIG. 7B is a flow chart illustrating general process steps for operating a system utilizing machine-readable suture markers or active suture markers. In the flow chart, various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the device. Those skilled in the art may readily write such a control program based on the flow charts and other descriptions presented herein.

As shown in FIG. 7B a system receives data input in the form of video data 760. The system may also receive additional sensor data 762 indicative of suture conditions. The sensor data 762 may be data transmitted to the system by sensor devices such as shown in FIGS. 6A-6C. Sensor data 762 includes all data received by the system from the suture or sensors associated with the suture. The system may also receive data input 764 such as data from a keyboard, mouse, barcode or the like. Data input 764 may include, for example, an identification of the suture filament by entering a product identifier, reading a barcode or the like. As different sutures will have different features, the system will also have access to stored suture data 766 which may be a database of suture information identifying different sutures, the features of the sutures, and the markers of the sutures. The stored suture data 766 may be stored within the system or accessed over a network.

Referring again to FIG. 7B, at step 770, the system receives video data 760 and identifies markers present in the video data. At step 772, the system analyzes the markers identified in step 770 to generate information about the suture such as identifying sections of the suture, orientation of sections of suture, location of the suture and condition of the suture, such as tension. At step 774 the system identifies the suture based upon the data input 764. Alternatively, the suture may be identified based upon analysis of the markers at step 772 if the markers are characteristic of the suture (such as e.g. a barcode). The identity of the suture is utilized to identify the stored suture data about the features of the suture. This may include the manufacturer, size and material of the suture, the strength of the suture, and also information regarding correlations between markers of the suture and particular features of the suture and/or sections of the suture. For example, the stored data may indicate that a particular suture in use has a maximum strength of 7 pounds and an elongation of 1% per pound. These features are retrieved at step 776 and then used at step 778 to derive further information about the suture. For example, the system may analyze the marker positions to determine the elongation of the suture from the video data 760. From the elongation of the suture or a section of suture, the system can determine the tension in the suture using the stored suture data. The system may also compare the calculated suture tension with the maximum suture tension using the stored suture data. In some case the system may then issue a warning if the calculated suture tension over a threshold (which may be a predetermined percentage of the maximum tension). At step 770 the system augments the suture image data with additional suture information. The augmented image including the suture information is displayed to the physician at step 768. The system then loops back to receive more video data 760 and update the augmented display at step 768.

Display processing system 748 of FIG. 7A may integrate the suture data output into other display data in many different ways. See step 770 of FIG. 7B. Suture tension data may be displayed to the physician as haptic, visual or audio feedback. For haptic feedback, the calculated tension may be displayed as force-feedback to a force-feedback controller. For audio feedback, a sound may be played to the physician indicative of the tension in the suture. The fixed sound may be played when a particular desirable suture tension is reached or exceeded. Alternatively, a variable sound may be used which, for example, increases in frequency of occurrence, pitch or volume as tension in the suture increases. For visual feedback, a value, symbol or color indicative of suture tension may be displayed to the physician as part of or adjacent to the video display of the operative field. In some cases the visual data may be added to the image of the operative field by, e.g., superimposing a value, symbol or color on the image of suture 700 or surgical instruments 736, 737. Thus, display system 742 provides physician 710 with an augmented display that includes a representation of the operative filed augmented with information derived from the suture markers using suture information 746.

FIG. 7C illustrates an augmented video display 780 of the patient-side system 730 of FIG. 7A. FIG. 7C illustrates a number of ways in which a visual display may be augmented to indicate features and/or conditions of the suture. The type and size of suture 782 may be overlayed on the display. A tension meter 784 may be used to show the maximum tension and the actual tension in relative terms. Alternatively, actual tension and maximum tension information may be provided in absolute terms. Tension or other conditions of the suture may also be registered with and overlayed on the image of the suture and/or tools. For example, the system can overlay the suture with a different color based upon a feature of the suture (such as e.g. retainer orientation or tension) derived from marker data or other data. Thus, as shown in FIG. 7C, the section of suture 700 between instruments 736, 737 is highlighted with color 786 representative of tension in suture 700. Whereas sections of suture 700 not tensioned by tools 736, 737 are highlighted with a different color 788 (or not highlighted).

Laser-Marked Indicia for Self-Retaining Sutures

As discussed above, it is particularly desirable to mark and identify portions of a heterofunctional suture system where different sections of the suture have different features such as in bidirectional self-retaining suture systems. In self-retaining suture systems the difference in function between sections of the suture may be the presence, absence and/or orientation of retainers. In one aspect it may be desirable to mark the transition section of a bidirectional suture. In one embodiment of the present invention electromagnetic radiation is used to create recognizable indicia on the transition section of a self-retaining suture in a manner that allows a physician to identify and differentiate the transition section. In one embodiment, a laser is used to create laser-marked indicia which are readily recognized and distinguished by the physician under the conditions in which the suture is to be used thereby allowing the surgeon to locate the transition region and/or other section of the self-retaining suture. The laser radiation can impart denaturation or discoloration to the suture dye or pigment, or bleach an area of the suture.

In preferred embodiments, the suture thread includes a colorant which changes color in response to laser exposure. Colorants include both dyes (water soluble) and pigments (not water soluble). Preferred colorants are non-reactive and biologically inert. Colorants are available in a variety of colors including black and white. In addition, colorants include dyes and pigments which can be visualized using alternate sources of energy such as using a "black light" which makes the colorant fluoresce or otherwise become visible. The colorant is, in preferred embodiments, a colorant approved for use in sutures in the relevant jurisdiction. The colorants that may be used in sutures are regulated in the United States by the Food and Drug Administration (FDA). Thus, in preferred embodiments, the colorant is a color additive identified in 21 C.F.R. 73(D) as exempt from certification for the specified suture application; and/or a color additives identified in 21 C.F.R. 74(D) as subject to certification for the specified suture application. Suitable colorants for sutures include, for example, titanium dioxide, D&C Violet No. 2; D&C Blue #6; D&C Blue #9; D&C Green #5; FD&C Blue #2; Logwood extract; [Phthalocyaninato(2-)]copper; and Chromium-cobalt-aluminum oxide.

The suture colorant selected for a particular internal suturing application is preferably selected to enhance the visibility of the suture. A light/bright colorant (including white) is preferred in embodiments where the suture will be used in dark tissue—for example the liver. A dark colorant (including black) is preferred in embodiment where the suture will be used in light tissue, for example fatty tissue. In some cases it may be desirable to use a color for the suture that is uncommon in the operative environment. For example, it may be desirable to use green suture because green is not common in the human body. In endoscopic applications using green is advantageous because the video system can be programmed to emphasize green and enhance marker visualization without interfering with the remainder of the image. However, if a superficial of cosmetic suture will not be removed the colorant is, in some embodiments selected so that the suture will not be visible through the skin of the patient. Moreover, for absorbable superficial sutures, the colorant should be selected so that coloration will not be visible through the skin of the patient after the suture degrades.

The suture colorant is also selected for its ability to change color in response to laser exposure that does not damage the suture. In preferred embodiments treatment of the suture with laser causes a color change in the treated region(s) which has high contrast with the untreated region(s). This enhances the visibility of the laser-marked indicia. The change in color is in particular embodiments from colored to uncolored, from uncolored to colored, from a first color to a second color different than the first color, and/or from a color at a first density to the same color at a different density.

In one embodiment, titanium dioxide ($TiO_2$) is incorporated into the material of the self-retaining suture prior to extrusion. The titanium dioxide is an inert pigment that colors the suture thread white. Titanium dioxide is in some embodiments 2%, 1% or less by weight of the suture/pigment blend. UV laser energy directed at the suture can be used to generate high contrast black marks against the white background. The UV laser radiation does not penetrate far into the suture—in preferred embodiments the penetration is less than 2 μm. The small penetration of the UV laser energy into the suture minimizes the extent and degree of disruption to the suture thread.

In an alternative embodiment, [Phthalocyaninato(2-)]copper is incorporated in the material of a polypropylene suture. [Phthalocyaninato(2-)]copper is a biocompatible colorant which colors the suture thread blue. Visible laser energy directed at the suture can be used to denature the [Phthalocyaninato(2-)]copper so that it is no longer blue. The laser energy changes the color of [Phthalocyaninato(2-)]copper by eliminating the blue color. Essentially, the color is bleached generating a high contrast between the area of laser exposure where the blue color is absent and the blue areas which were not treated with the laser. In preferred embodiments, the laser penetrates to the center of the suture to denature the [Phthalocyaninato(2-)]copper through the section of the suture targeted for creation of the indicia.

In a preferred embodiment, the colorant is dispersed into the bulk form of the thermoplastic resin prior to extrusion of the suture thread. For example, a dry colorant is in some embodiments blended and uniformly dispersed into the thermoplastic resin in pellet, granule or chip form and dry. The amount of colorant employed in the blend is selected to produce the desired coloration in the suture thread. For example, colorants are in some embodiments employed in amounts up to about 0.2% by weight, based on the total weight of colorant and resin, more preferably from about 0.01 to about 0.2% by weight, more preferably from about 0.05 to 0.1% by weight and, most preferably, at about 0.075% by weight. In alternative embodiments higher or lower amounts of colorant can be utilized. The dry blend of resin and colorant is then extruded using conventional techniques to create the suture thread. Laser-marked indicia may be usefully placed on suture threads including: monofilament suture thread, extruded multi-material suture thread, braided suture thread, coated/sheathed braided suture thread; natural suture thread and combinations thereof.

In general, a laser head is used to apply a laser beam to the surface of the suture thread. The laser energy is absorbed by the suture thread. In preferred embodiments the laser energy is preferentially absorbed by the colorant which changes in appearance. The laser energy changes the appearance of the laser-reactive constituent in the selected area by increasing, decreasing or changing a color, contrast, reflectivity, transparency or other visualizable property within the selected area relative to non-selected areas of the suture. The change in color of the colorant can be achieved by one or more of: breaking bonds in the colorant; changing bonds in the colorant; realigning bonds in the colorant; and/or changing the stereochemistry of the pigment. The laser reactive constituent is in embodiments of the invention a polymer incorporated or colorant into the suture thread before, during or after manufacture of the suture thread.

The laser light is provided at power, wavelength, and pulse duration selected to change the appearance of the laser reactive constituent of the self-retaining suture in the selected area without damaging the self-retaining suture. The wavelength of the laser is typically in the range of UV to visible to infrared light. Light as used herein is not limited to the visible spectrum. The ideal wavelength for causing color change in a colorant will often be different for each colorant. The exposure required to cause the desired color change may be accomplished in one continuous exposure or a plurality of pulses. Exposure to a plurality of laser pulses allows the energy of each laser pulse to dissipate and therefore induces a lower temperature rise in the suture thread than one continuous pulse of the same total length. The power of the laser beam and/or pulse duration are controlled to change the color of the suture thread while delivering insufficient total energy to adversely affect the bulk material properties of the suture thread. For example, in a preferred embodiment a femtosecond laser is used which provides high power for very short duration laser pulses. The wavelength, power, focus and/or pulse duration are also controlled to achieve the desired penetration of the laser into the suture thread.

A variety of different lasers and control system can be used to direct the laser to the selected locations of a suture and generate the selected laser marked-indicia. In some embodiments, a steered beam laser marking system is used to create the laser-marked indicia. In a steered beam system a pulsed laser is directed at a moving point on the suture thread. Mirrors mounted on computer-controlled galvanometers to draw lines, patterns and characters on the surface of the suture thread. In alternative embodiments, an imaged-mask laser system is used to create the laser-marked indicia. A metal stencil mask is created with an aperture in the shape of the desired laser-marked indicia. The metal stencil is illuminated by the laser which is imaged onto the suture thread using a lens. The image of the entire stencil is marked on the suture with a single pulse of laser light. In alternative embodiments, a dot-matrix laser system is used to create the laser marked indicia. Dots are produced on the suture thread by modulating a laser on or off and controlling the location using a rotating polygonal mirror in stepwise fashion.

In embodiments of the present invention, laser-marked indicia are provided on one or more of the suture thread, regions of the suture thread, the retainers, the needles, or another item, such as a pledget, associated with a bidirectional self-retaining suture system or section of the suture thread. The laser-marked indicia can, in some embodiments, be provided in various forms that are distinguishable from one another. The laser-marked indicia can, in some embodiments, comprise one or more distinguishable, patterns, shapes, lengths, colors sizes, directions and arrangements. The laser-marked indicia are used in a uniform density or varying density in which case the graduation of density may be used to designate e.g. an orientation. The markers may be included along the entire length of the self-retaining suture system, at a number of discrete points, or only at the ends or transition section of the self-retaining suture.

The shape and/or distribution of the laser-marked indicia are, in preferred embodiments, selected so as to enhance the visibility of the indicia during use. A variety of patterns including: concentric rings of uniform and/or variable thickness, dot patterns, dash patterns, random patterns, longitudinal striping, alphanumerics and/or combinations thereof may be applied to mark the suture for optimal visualization by the clinician. This also includes patterns made from a variety of different shades of pigment discoloration. For example, a suture could be manufactured with a mixture of two pigments where light energy is used to change the suture color by changing the color of the one pigment more than the second pigment thus causing a change in the suture color. The pattern of the marking can be varied, i.e. single/multiple rings, rings of equal or different width, longitudinal patterns and combinations of the foregoing. The intensity of the blanching can be varied individually or in a pattern to focus attention at the center. A wide variety of different shapes and distributions of laser-marked indicia can be used so long as they are distinguishable by the physician under the conditions of use. Laser-marked indicia can be formed in all of the shapes and distributions described herein. (See, e.g. FIGS. 1A-1D and FIGS. 3A-3I and accompanying text).

In a preferred embodiment, the laser-marked indicia are bands visible from all sides of the suture thread. Different sections of the suture are provided with different configurations or densities of bands (including no bands) in order that the different sections of the self-retaining suture may be recognized and identified by a surgeon. FIGS. 8A-8H show alternative configurations of laser-marked bands which are used to identify sections of bidirectional self-retaining suture thread in accordance with embodiments of the present invention.

Figure 8A:
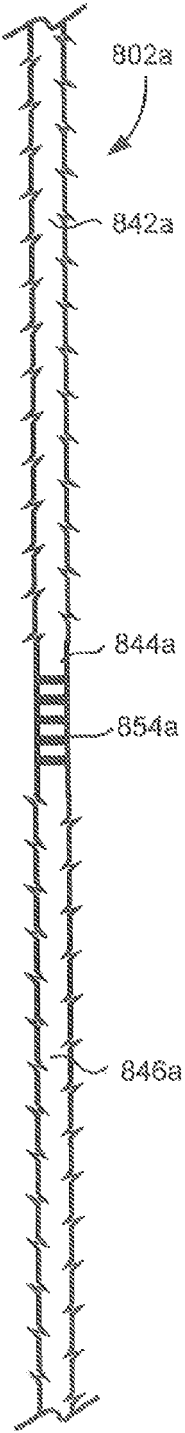
FIGS. 8A-8H show alternative configurations of laser-marked indicia used to identify sections of a bidirectional self-retaining suture in accordance with embodiments of the present invention.

As shown in FIG. 8A, a bidirectional self-retaining suture 802a has a first section 842a having a plurality of retainers oriented in a first direction; a second section 846a having a plurality of retainers oriented in a second direction; and a transition section 844a having no retainers and positioned between the first section 842a and the second section 846a. Self-retaining suture 802a has a plurality of laser-marked bands 854a on the transition section indicating the location of the transition section 854a. The term "transition section" refers to the middle non-barbed segment of a bidirectional self-retaining suture. The transition section is, in some embodiments, in the center of the self-retaining suture. However, if the self-retaining suture has an asymmetric design, then the transition zone is in some embodiments closer to one end of the self-retaining suture than the other. In this embodiment, first section 842a and second section 844a have no laser marked indicia. However, in a bidirectional self-retaining suture, if the transition section 844a is identified—it is known that the first section 842a and second section 846a are located on either side of the transition region 844a. Thus, the positions of first section 842a and second section 846a can be implied from the laser-marked indicia on transition section 844a.

Figure 8B:
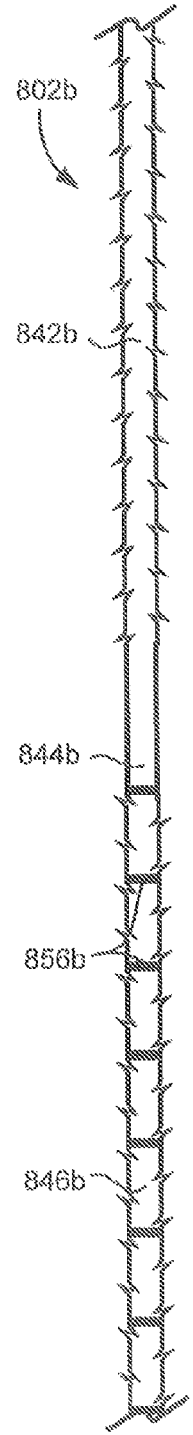

As shown in FIG. 8B, a bidirectional self-retaining suture 802b has a first section 842b having a plurality of retainers oriented in a first direction; a second section 846b having a plurality of retainers oriented in a second direction; and a transition section 844b having no retainers and positioned between the first section 842b and the second section 846b. Self-retaining suture 802b has a plurality of laser-marked bands 856b on the second section 846b indicating the location of the second section 846b. Although laser-marked bands 856b are illustrated as dark bands on a light background (as would be achieved by UV laser exposure of a suture thread containing titanium dioxide) bands 856b are, in some embodiments, bands where a colored suture has been bleached by laser exposure. In this embodiment, first section 842b and transition section 844b have no laser marked indicia. However, in a bidirectional self-retaining suture if the second section 846b is identified—it is known that the transition section 844b is located adjacent second section 846b. Thus, the position of transition section 844b can be implied observing where bands 856b terminate. The laser-marked indicia of FIG. 8B not only allows the physician to locate transition section 844b, but also allows the physician to discriminate first section 842b from second section 844b.

Figure 8C:
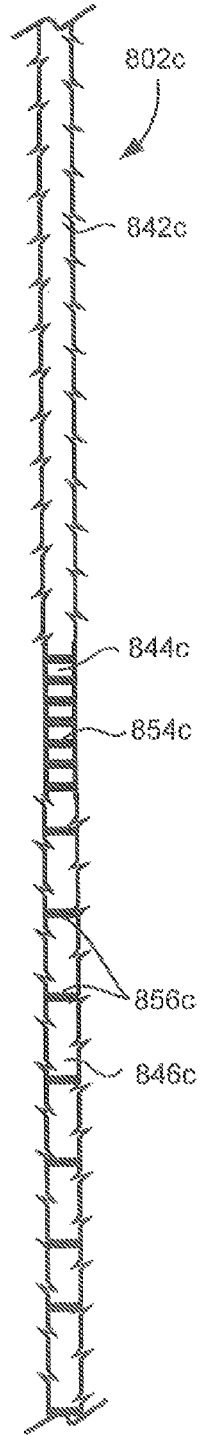

As shown in FIG. 8C, a bidirectional self-retaining suture 802c has a first section 842c having a plurality of retainers oriented in a first direction; a second section 846c having a plurality of retainers oriented in a second direction; and a transition section 844c having no retainers and positioned between the first section 842c and the second section 846c. Self-retaining suture 802c has a plurality of laser-marked bands 856c on the second section 846c indicating the location of the second section 846c. Self-retaining suture 802c also has a plurality of laser-marked bands 854c on the transition section 844c indicating the location of the transition section 844c. Although laser-marked bands 854c, 856c are illustrated as dark bands on a light background (as would be achieved by UV laser exposure of a suture thread containing titanium dioxide) bands 854c, 856c are in some embodiments bands where a colored suture has been bleached by laser exposure. The spacing between laser-marked bands 854c is significantly smaller than the spacing between bands 856c. Thus, the transition section 844c can be differentiated from first section 842c and second section 846c. The laser-marked indicia of FIG. 8C not only allows the physician to locate transition section 844c, but also allows the physician to discriminate first section 842c from second section 844c.

Figure 8D:
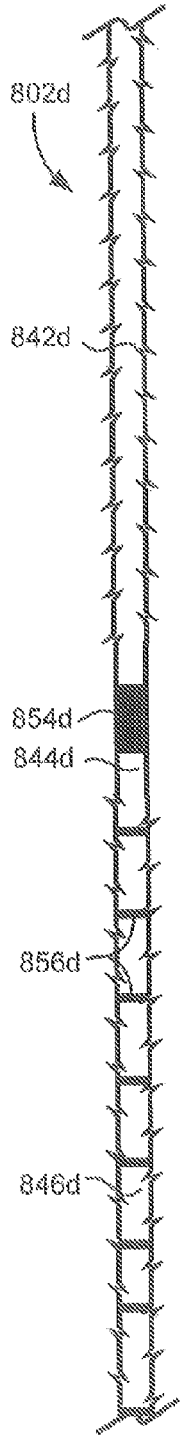

As shown in FIG. 8D, a bidirectional self-retaining suture 802d has a first section 842d having a plurality of retainers oriented in a first direction; a second section 846d having a plurality of retainers oriented in a second direction; and a transition section 844d having no retainers and positioned between the first section 842d and the second section 846d. Self-retaining suture 802d has a plurality of laser-marked bands 856d on the second section 846d indicating the location of the second section 846d. Self-retaining suture 802d also has a single large band 854d on the transition section 844d indicating the location of the transition section 844d. The laser-marked band 854d is significantly larger than the bands 856c. Thus, the transition section 844d can be differentiated from first section 842d and second section 846d. The laser-marked indicia of FIG. 8D not only allows the physician to locate transition section 844d, but also allows the physician to discriminate first section 842d from second section 844d.

Laser-marked bands 854a, 856b, 854c, 856c, 854d and 856d are illustrated in FIGS. 8A, 8B, 8C and 8D as dark bands on a light background (as would be achieved by UV laser exposure of a suture thread containing titanium dioxide). However bands 854a, 856b, 854c, 856c, 854d and 856d also represent, in some embodiments, bands where a colored suture has been bleached or changed in color by laser exposure (as would be achieved for example by bleaching [Phthalocyaninato(2-)]copper in a suture thread).

Figure 8E:
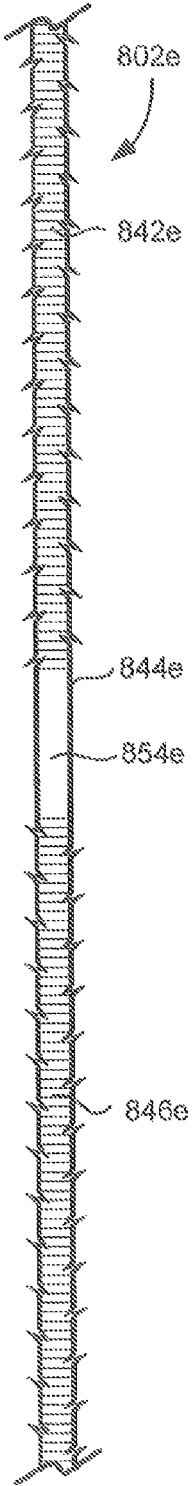

As shown in FIG. 8E, a bidirectional self-retaining suture 802e has a first section 842e having a plurality of retainers oriented in a first direction; a second section 846e having a plurality of retainers oriented in a second direction; and a transition section 844e having no retainers and positioned between the first section 842e and the second section 846e. Self-retaining suture 802e includes a colorant which colors the self-retaining suture uniformly during manufacture (for example blue—[Phthalocyaninato(2-)]copper). Self-retaining suture 802e has a laser-marked band 854e on the transition section 844e indicating the location of the transition section 844e. As shown in FIG. 8A, laser-marked band 854e is a region of self-retaining suture 802e where the colorant has been changed in color by exposure to laser light. The bleached band (non-shaded) can thus be distinguished from the colored suture (shaded). Thus, the transition section 844e can be differentiated from first section 842e and second section 846e.

Figure 8F:
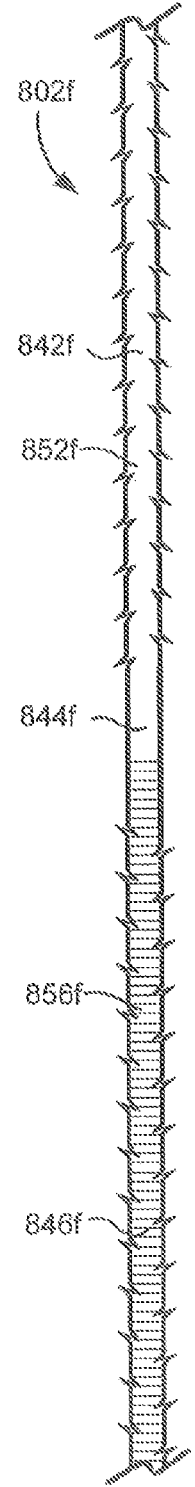

As shown in FIG. 8F, a bidirectional self-retaining suture 802f has a first section 842e having a plurality of retainers oriented in a first direction; a second section 846f having a plurality of retainers oriented in a second direction; and a transition section 844f having no retainers and positioned between the first section 842f and the second section 846f. Self-retaining suture 802f includes a colorant which colors the self-retaining suture uniformly during manufacture (for example blue—[Phthalocyaninato(2-)]copper). First section 842f and transition section 844f have been treated with a laser to bleach the colorant and generate a bleached suture portion 843f. The bleached suture portion 853f (non-shaded) can thus be distinguished from the colored suture portion 856f (shaded). The transition section 844f can be located by the boundary between the colored suture portion 856f and the bleached suture portion 843f. Moreover, first section 842f (bleached) can also be distinguished from second section 846f (colored).

Figure 8G:
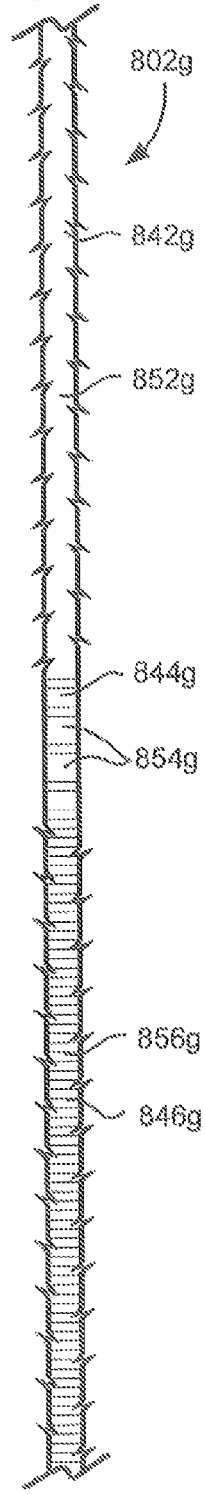

As shown in FIG. 8G, a bidirectional self-retaining suture 802g has a first section 842g having a plurality of retainers oriented in a first direction; a second section 846g having a plurality of retainers oriented in a second direction; and a transition section 844g having no retainers and positioned between the first section 842g and the second section 846g. Self-retaining suture 802g includes a colorant which colors the self-retaining suture uniformly during manufacture (for example blue—[Phthalocyaninato(2-)]copper). First section 842g has been treated with a laser to bleach the colorant and generate a bleached suture portion 842g. Transition section 844g has been treated with a laser to create a plurality of bleached band 854g. The bleached suture portion 852g (non-shaded) can thus be distinguished banded suture portion 854g (shaded in part) which can be distinguished from the colored suture portion 856g (shaded). The transition section 844g can be located by the banded suture portion 854g. Moreover, first section 842g (bleached) can also be distinguished from second section 846g (colored).

In some embodiments, treatment with a laser causes a suture to change color from a first color to a second color. For example, a suture including both a yellow and blue colorant is uniformly colored green during manufacture. A laser treatment is selected which preferentially denatures the blue colorant and not the yellow colorant. In areas treated with the laser, the suture thus changes to a yellow color from a green color when the blue colorant is denatured. Bleached portions 854e, 852f, 852g, and 854g are illustrated in FIGS. 8E, 8F and 8G as white/colorless portions against a colored/shaded background (as would be achieved, for example, by bleaching [Phthalocyaninato(2-)]copper in a suture thread). However, bands 854a, 854e, 852f, 852g, and 854g also represent, in some embodiments, bands where a colored suture has been changed in color by laser exposure (as would be achieved for example by bleaching [Phthalocyaninato(2-)]copper in a suture thread which also includes another different color colorant not affected by the laser exposure).

Figure 8H:
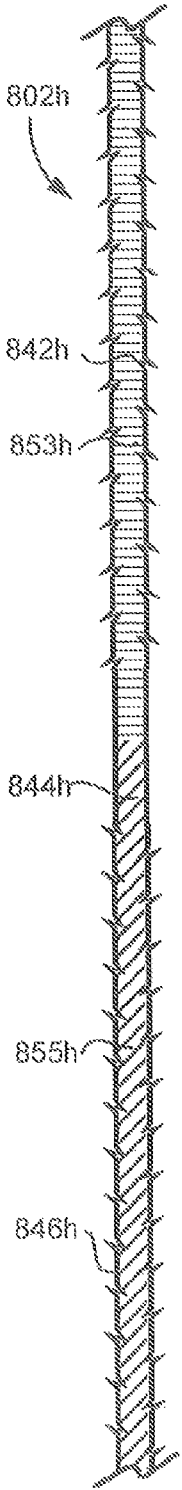

As shown in FIG. 8H, a bidirectional self-retaining suture 802h has a first section 842h having a plurality of retainers oriented in a first direction; a second section 846h having a plurality of retainers oriented in a second direction; and a transition section 844h having no retainers and positioned between the first section 842h and the second section 846h. Self-retaining suture 802h includes a colorant which colors the self-retaining a first color during manufacture. A first color portion of the suture 853h has not been treated with a laser and retains the first color. A second color portion of suture 855h has been treated with a laser to change the color to a second color. The first color portion 853h can thus be distinguished from the second color portion 855h. The transition section 844h can be located by the boundary between the first color portion 853h and the second color portion 855h. Moreover, first section 842h (first color) can also be distinguished from second section 846h (second color).

Laser-marked indicia may also be used on self-retaining sutures which are not bidirectional and also on non-self-retaining sutures. FIGS. 8I-8J show alternative configurations of laser-marked bands used to identify sections of singled armed self-retaining suture thread in accordance with embodiments of the present invention. FIGS. 8K-8L show alternative configurations of laser-marked bands used to identify features of an ordinary suture thread in accordance with embodiments of the present invention.

As shown in FIG. 8I, a self-retaining suture 802i has a needle 810i connected to a lead-in section 840i, connected to a first section 842i having a plurality of retainers oriented in a first direction connected to a second section 844i having no retainers. Self-retaining suture 802i includes a colorant which colors the self-retaining suture uniformly during manufacture (for example blue—[Phthalocyaninato(2-)]copper). Self-retaining suture 802i has a laser-marked band 850i on the lead-in section 840i. Self-retaining suture 802i also has a laser-marked band 854i on the second section 844i. As shown in FIG. 8I, laser-marked bands 850i and 854i are regions of self-retaining suture 802i where the colorant has been changed in color (for example bleached) by exposure to laser light. The bleached bands 850i, 854i of suture thread (non-shaded) can thus be distinguished from the colored suture (shaded). Thus, first section 842i can be thereby distinguished from the lead-in section 840i and second section 844i which have no retainers.

As shown in FIG. 8J, a self-retaining suture 802j has a needle 810j connected to a lead-in section 840j, connected to a first section 842j having a plurality of retainers oriented in a first direction connected to a second section 844j having no retainers. An optional suture anchor 846j is connected to the end of second section 844j. Self-retaining suture 802j includes a colorant which colors the self-retaining suture uniformly during manufacture (for example blue—[Phthalocyaninato(2-)]copper). Self-retaining suture 802j has a laser-marked band 852j on the first section 842j. As shown in FIG. 8J, laser-marked bands 852j is a region of self-retaining suture 802j where the colorant has been changed in color (for example bleached) by exposure to laser light. The bleached band 852j of suture thread (non-shaded) can thus be distinguished from the colored suture (shaded). Thus, first section 852j can be thereby distinguished from the lead-in section 840j and second section 844j which have no retainers.

As shown in FIG. 8K an ordinary (not self-retaining) suture thread 820k is swaged to a suture needle 810k. Suture thread 820k includes a colorant which colors the self-retaining suture thread 820*k* uniformly during manufacture (for example blue—[Phthalocyaninato(2-)]copper). A plurality of laser-marked bands, 850*k*, 852*k* has been formed on suture thread 820*k*. As shown in FIG. 8K, laser-marked bands 850*k*, 852*k* are regions of suture thread 820*k* where the colorant has been changed in color (for example bleached) by exposure to laser light. The bleached bands 850*k*, 852*k* of suture thread (non-shaded) can thus be distinguished from the colored suture (shaded). Bands 850*k* and 852*k* and other bands (not shown) can be positioned at regular intervals along suture thread 820*k* to provide an indication of distance and/or scale to the surgeon.

As shown in FIG. 8L an ordinary (not self-retaining) suture thread 8201 is swaged to a suture needle 810*k*. Suture thread 8201 has a plurality of laser-marked indicia 8501, 8521, 8541, 8561. Each of the indicia comprises a different number of laser-marked bands so that the indicia can be distinguished one from another. An optional suture anchor 8461 is connected to the end of suture thread 8201. As shown in FIG. 8L, the bands of laser-marked indicia 8501, 8521, 8541, 8561 are regions of suture thread 820*k* where the colorant has been changed in color by exposure to laser light for example, dark regions produced by laser exposure of a suture containing titanium dioxide. The bands can thus be distinguished from the suture and the indicia may be distinguished from one another based upon the number of bands. The indicia can be positioned at regular intervals along suture thread 8201 to provide an indication of distance from e.g. suture anchor 8461 and/or needle 8101. In the embodiment shown in FIG. 8L, the number of bands in the laser marked indicia 8501, 8521, 8541, 8561 is indicative of distance from the suture anchor 8461.

In other embodiments, laser-marked indicia are created on other self-retaining or non-self-retaining implantable polymer implants. For example, a surgical mesh can be formed from a polymer which includes a colorant. Exposure of regions of the mesh to a laser can be used to change the color of the colorant in the exposed regions thereby generating laser-marked indicia on the mesh. The laser-marked-indicia can be used to identify portions of the mesh having particular functionality. The laser-marked indicia can also be used to assist the surgeon in placement/or orientation of the mesh. A range of medical devices can be marked by techniques described herein including, for example, orthopedic implants (artificial joints, ligaments and tendons; and other implantable hardware), dental implants, intravascular implants (arterial and venous vascular bypass grafts, hemodialysis access grafts; both autologous and synthetic), skin grafts (autologous, synthetic), tubes, drains, pumps, shunts, sealants, surgical meshes (e.g., hernia repair meshes, tissue scaffolds), fistula treatments, spinal implants (e.g., artificial intervertebral discs, spinal fusion devices, etc.) and the like.

Laser System for Marking Sutures

The laser-marked indicia of a self-retaining or ordinary suture should be located appropriately to identify particular sections/features of the self-retaining suture as described above. Thus, it is important that the laser-marking system be configured to align the laser marking head with the appropriate locations of the suture. This can be achieved, for example, by incorporating the laser marking head into the retainer-forming machine which creates the retainers. After the suture thread is mounted in the machine, the retainer-forming machine indexes the suture longitudinally from position to position relative to a retainer-forming head to form retainers. The same machine, with information about the relative positions of the retainer-forming head and laser-marking head can also index the suture correctly relative to the laser-marking head and activate the laser marking-head to create the laser-marked indicia at the appropriate position or positions on the self-retaining suture.

Figure 9A:
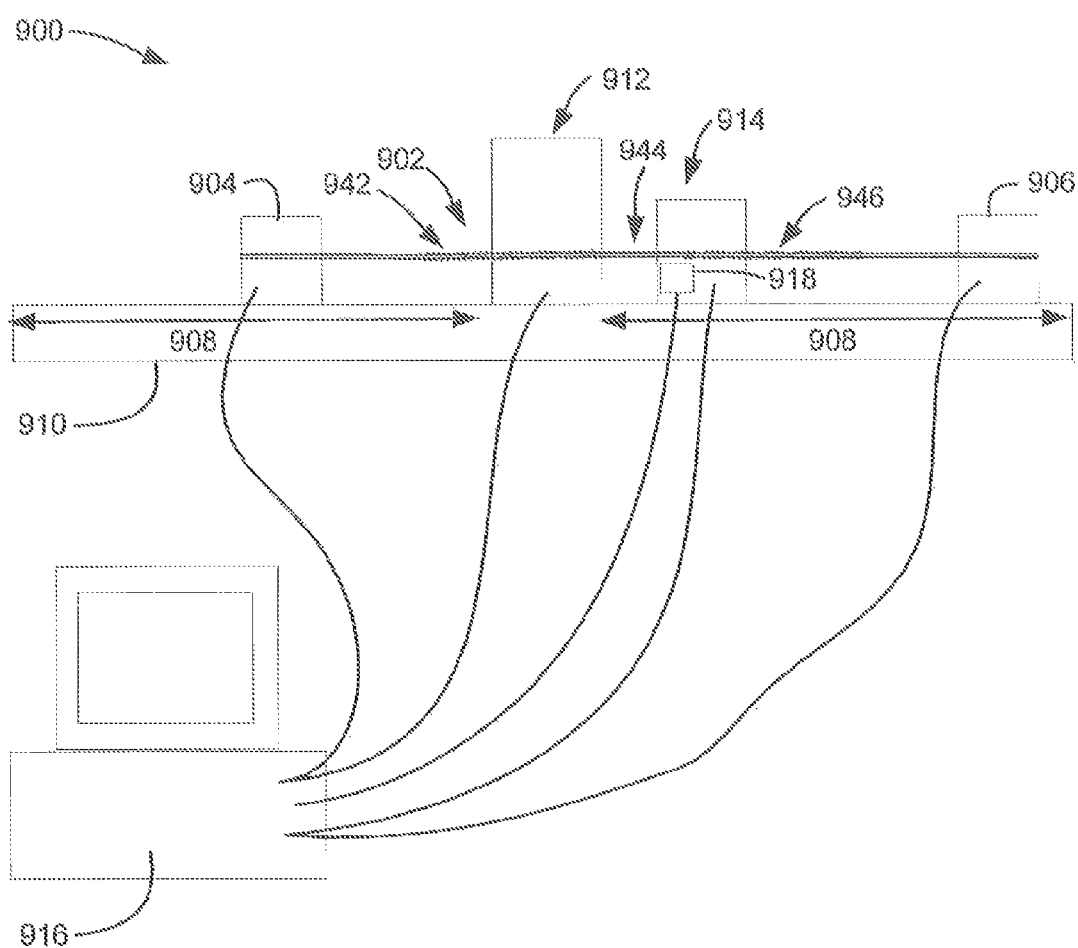
FIG. 9A shows a block drawing of a retainer-forming machine and integrated laser-marking head according to an embodiment of the invention.

FIG. 9A, shows a schematic diagram of a retainer-forming machine 900 with integrated laser marking head 914 for making self-retaining sutures and selectively creating laser-marked indicia on selected sections of the self-retaining sutures. As shown in FIG. 9A, retainer-forming machine 900 is configured to form retainers on suture thread 902 to create a self-retaining suture. Retainer-forming machine 900 comprises a pair of chucks 904, 906 which hold the ends of suture thread 902. Chucks 904, 906 are mounted on a base 910. Chucks 904, 906 are configured so as to translate together along base 910 as shown by arrows 908 and also to rotate suture thread 902. Chucks 904, 906 are thus adapted to move suture thread relative to a retainer-forming head 912 and laser-marking head 914 which are fixed relative to base 910. Chucks 902, 906, retainer-forming head 912 and laser-marking head 914 are under the control of a computer system 916.

Laser-marking head 914 may include an imaging device 918 for verifying the laser-marked indicia. Imaging device 918, if present, feeds verification information to computer system 916. The imaging device is in some embodiments a digital still or video camera with suitable magnification for imaging the suture and distinguishing the contrast of the laser-marked indicia. The imaging device in preferred embodiments has an adjustable light for illuminating the suture thread in a manner which is optimal for the retainer or laser-marked indicia being imaged. Laser marking head 914 includes standard laser optic components including: collimators, masks, lenses, galvanometers and mirrors. The laser optic components are arranged to direct the laser light to a particular region of the suture thread and not other regions of the suture thread in order to create the desired indicia. The laser marking head, in some embodiments, also includes component for correctly aiming the laser suture thread with the laser to ensure the marking is correctly positioned. The aiming device can incorporate an optical device such as imaging device 918. The use of a laser-marking head is advantageous in a retainer-forming machine because the laser marking head can operate without contacting the suture thread.

After suture thread 902 is mounted to chucks 904, 906, under control of computer system 916, the chucks 904, 906 translate and rotate suture thread 902 stepwise relative to retainer-forming head 912. At selected positions of suture thread 902, computer system 916, activates retainer-forming head 912 to form a retainer on suture thread 902. The process is repeated stepwise until, for example, suture thread 902 is a bidirectional self-retaining suture having a first section 942 having a plurality of retainers oriented in a first direction; a second section 946 having a plurality of retainers oriented in a second direction; and a transition section 944 having no retainers and positioned between the first section 942 and the second section 946.

Before, during, or after creation of the retainers, under control of computer system 916, the chucks 904, 906 translate and rotate suture thread 902 relative to laser-marking head 914. At selected positions of suture thread 902 relative to laser-marking head 914, computer system 916, activates laser marking head 914 to create a laser marked indicia on suture thread 902. The process is repeated stepwise until, for example suture thread 902 has laser marked indicia at all the desired positions. At selected positions of suture thread 902 relative to imaging device 918, computer system 916, may also activate imaging device 918 to validate correct creation and/or location of laser-marked indicia on suture thread 902.

FIG. 9B, shows a flow chart of an example of a process 920 for creating a bidirectional self-retaining suture thread with laser-marked indicia at selected locations on the suture thread—for example the transition section. In step 922, a suture thread having a laser reactive colorant of other constituent is obtained and/or manufactured. In step 924, the suture thread is mounted in the retainer-forming machine and mounted to the chucks.

In step 926, the chucks index the suture thread to a desired position by translating and/or rotating the suture thread relative to the retainer-forming head and/or laser-marking head. The retainer-forming machine has a linear transport mechanism which includes the chucks for moving the self-retaining suture through the retainer-forming head and laser-marking head.

In step 928, the retainer forming head is actuated if the suture is correctly positioned for forming a retainer. The controller of the retainer-forming head records the position of the retainers on the self-retaining suture.

In step 930, the laser-marking head is actuated to create a laser-marked indicia if the suture is correctly positioned for creating a laser-marked indicia. The retainer-forming machine indexes the targeted sections of the self-retaining suture to be aligned with the laser-marking head without requiring re-indexing and identification of the section of the self-retaining suture thread. The self-retaining suture thread is exposed to laser light from the laser-marking head to create the desired laser-marked indicia. The laser-marking head may expose all of the selected area at one time or may selected sub-portions of the selected area in a sequential process to create the desired laser-marked indicia.

In step 932, the imaging device is actuated to imaging device is actuated if the suture is correctly positioned for verification of e.g. a laser-marked indicia. In a preferred embodiment, the laser-marking head has an optical sensor for imaging the selected area of the suture thread and verifying that the visual property of the suture thread in the selected area has changed to the desired value after exposure to the laser light. If the laser-marked indicia are not verified the sensor indicates a fault to the operator who can check the machine and the self-retaining suture.

In step 934 the step-wise process repeats, returning to step 926 until all of the desired retainers have been formed and all the desired laser-marked indicia created. If all of the desired retainers have been formed and all the desired laser-marked indicia created, then, at step 938, the bidirectional self-retaining suture thread is complete. The suture thread may be unloaded from the chucks, have the retainer-less lead-in sections trimmed and have needles swaged on each end.

In alternative embodiments, a marking head other than a laser-marking head is incorporated in the retainer-forming machine. The retainer forming machine controls the retainer formation and marking as previously discussed, however, the marking head uses another technology to create the indicia. For example, embodiments of the marking head include a spray head, painting head, printing head, coating head and the like for applying a colorant to the suture or removing a colorant from the suture thread in a controllable manner to create indicia. The marking head can in some embodiments be contacting or contactless. The marking head can also be a head that coins a feature in the suture thread. The marking head can create a marking feature on the suture thread by one of creating a deformation, a discontinuity, an indentation, a loop, a protrusion, a ridge and a reduced diameter. Additionally, the marking head can be a head that dispenses one of a fluid, a supercritical fluid and a dye extraction agent to expose the suture thread to one of said fluid, said supercritical fluid and said dye extraction agent in order to change, reduce or extract the color of the suture or in order to change, reduce or extract the color of a colorant of the suture.

In alternative embodiments, the indicia, laser-marked or otherwise, are created on the suture thread in a process prior to loading the suture thread on the retainer-forming machine. In such case a retainer forming machine may be used similar to retainer-forming machine 900 of FIG. 9A but without laser-marking head 914 but still retaining an imaging device 918. After the suture thread is loaded, the imaging device 918 is used to identify the position of the indicia and provide the location of the information to the computer system. The computer system then controls retainer-forming machine to form retainer in the correct relationship to the detected position of the indicia. For example, the suture thread may be a suture half one color and half another color produced by any of the methods described herein. When loaded in the retainer-forming machine the imaging device 918 is used to locate the boundary between the two colors. The retainer-forming machine 900 then forms the retainers at positions relative to the boundary such that the transition section of the self-retaining suture is located at the boundary. This alternate process is useful, for example, where the indicia creating process is incompatible with integration into the retainer-forming machine or more efficiently utilized off-line from the retainer-forming process.

FIG. 9C, shows a flow chart of an example of a process 960 for creating a bidirectional self-retaining suture thread with retainers position at selected locations on the suture thread relative to a pre-marked indicia—for example, a transition from one color to anther color. In step 962, a suture thread having pre-marked indicia at the desired transition section is obtained and/or manufactured. In step 964, the suture thread is mounted in the retainer-forming machine and mounted to the chucks.

In step 966 the chucks translate and/or rotating the suture thread relative to the imaging device 918 until the pre-marked indicia is located. The computer system records the location of the pre-marked indicia.

In step 968, the chucks index the suture thread to a desired position by translating and/or rotating the suture thread relative to the retainer-forming head. The retainer-forming machine has a linear transport mechanism which includes the chucks for moving the self-retaining suture through the retainer-forming head and laser-marking head.

In step 970, the retainer forming head is actuated if the suture is correctly positioned relative to the pre-marked indicia for forming a retainer. The retainer-forming machine indexes the targeted sections of the self-retaining suture correctly with respect to the pre-marked without requiring additional re-indexing and identification of the section of the self-retaining suture thread.

In step 972 the step-wise process repeats, returning 974 to step 968 until all of the desired retainers have been formed. If all of the desired retainers have been formed, then, at step 976, the bidirectional self-retaining suture thread is complete. The suture thread may be unloaded from the chucks, have the retainer-less lead-in sections trimmed and have needles swaged on each end.

Non-Coherent Electromagnetic Radiation for Marking Sutures

In alternative embodiments, non-coherent light or other electromagnetic radiation is used in place of laser light to create a color change in desired regions of the suture thread to create indicia. The non-coherent light should be of high enough intensity to cause the color change desired. The non-coherent light should be controlled in intensity and/or pulse duration to prevent damage to the suture thread. The frequency spectrum of the non-coherent light can be selected so as to be effective at causing color change of the suture thread without causing damage to the suture thread. The frequency spectrum of the non-coherent light is selected by choice of the light source and/or the use of filters. As described above for laser light, the spectrum of light includes, in embodiments of the invention, wavelengths from ultraviolet to visible light to infrared.

The non-coherent light should also be controlled in location so as to produce the desired indicia in the correct locations along the suture thread. Non-coherent light can with adequate directional control be used to generate any of the shapes and distribution of indicia described above with respect to laser-marked indicia. The non-coherent light can be controlled with standard optical components including: collimators, mask, lenses, filters, and mirrors. The optical components are arranged to direct the non-coherent light to a particular region of the suture thread and not other regions of the suture thread in order to create the desired indicia. In one embodiment, for example, the non-coherent light is directed only to the transition section of a bidirectional self-retaining suture in order to generate indicia which mark the location of the transition section. A non-coherent light marking head may incorporated into a suture-forming machine in the same way as the laser-marking head 912 described with respect to FIG. 9A and utilized in the same process as described with respect to FIG. 9B. The non-coherent electromagnetic radiation can impart denaturating or discoloration to the suture dye, or pigment or blanch an area of the suture. The non-coherent electromagnetic radiation can be used to create self-retaining and ordinary sutures having indicia arranged in the patterns and distributions previously discussed with respect to laser-marked indicia. For example, non-coherent electromagnetic radiation can be used to create self-retaining and ordinary sutures having indicia arranged in the patterns shown in FIGS. 8A-8L.

Alternative Technologies for Marking Sutures

Indicia to allow identification of different sections of a self-retaining suture can be made using a variety of alternative technologies. For example, in one alternative embodiment, a supercritical fluid is used to extract colorant from selected areas of the suture thread in order to create indicia. The supercritical fluid extraction should be sufficient to cause the color change desired without damaging the suture thread. It is not necessary to remove all of the colorant from the transition zone as long as there is a visually distinguishable difference between the treated and non-treated areas. The supercritical fluid can be selected so as to be more effective at causing color change of the suture thread without causing damage to the suture thread.

In a preferred embodiment, carbon dioxide is used as the supercritical fluid. Supercritical carbon dioxide extraction is relatively rapid because of the low viscosity and high diffusivity of the supercritical carbon dioxide. The supercritical carbon dioxide can diffuse through solids like a gas and dissolve the colorants like a liquid. The application of the supercritical fluid should also be controlled in location so as to produce the desired indicia in the correct locations along the suture thread. For example, selective supercritical fluid extraction of colorants can be used to create self-retaining and ordinary sutures having indicia arranged in the patterns shown in FIGS. 8A-8L. In one embodiment, for example, the critical fluid is restricted to the transition zone to produce a result as illustrated in FIG. 8E. In another embodiment, for example, the entirety of one arm of the suture thread up to the middle of the transition zone is exposed to the critical fluid to produce a result as illustrated in FIG. 8F.

In alternative embodiments, a colorant is added to the suture to make indicia on desired positions along the suture thread. Conventional methods for applying a colorant include: dipping, spraying, painting, printing, applying and/or coating colorants on the selected suction of the suture—for example the transition section of a self-retaining suture. In one example, a layer of plastic such as an absorbable polyglycolide coating and/or a non-absorbable silicon coating which has a colorant is applied to the suture thread to mark the desired section. In another example a natural and/or modified natural material such as collagen or modified collagen and a colorant are used as the colored coating. Multiple colors can be applied in order to distinguish multiple sections. In another example, supercritical carbon dioxide is used to add a colorant to selected portions of a self-retaining suture. Again, the goal is to generate indicia that are visually distinguishable under the conditions of use. Thus, for example, fluorescent dyes and/or pigments are in some embodiments used to mark the center segment where the use of the self-retaining suture is under lighting conditions adapted to cause fluorescence of the pigments. The indicia are positioned to identify particular sections of a suture. For example a colorant application process can be used to create indicia on the transition section of a self-retaining suture. The selective addition of colorants can be used to create self-retaining and ordinary sutures having indicia arranged in the patterns shown, for example, in FIGS. 8A-8L.

In alternative embodiments, the selectable addition of a colorant to the suture thread (for example by dipping, spraying, painting, printing, applying and/or coating colorants on a selected suction of a suture thread) is performed in addition to a technique for selectively removing colorant from the suture thread as described above (for example, laser, non-coherent electromagnetic radiation or supercritical fluid). The selectable addition of colorant is in some embodiments performed before the removal step. In such embodiments, portions of the color selectively added can be selectively removed in the removal step. In alternative embodiments, the removal step is performed first to remove color from a colorant included in the suture thread. The later selectable addition of a colorant to the suture thread can be used to provide additional markings distinguishable from the markings produced by removal of colorant.

Figure 10A:
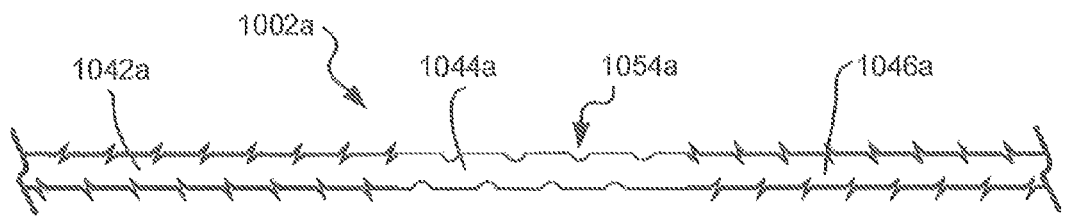
FIGS. 10A-10C show alternative configurations of indicia used to identify sections of a bidirectional self-retaining suture in accordance with embodiments of the present invention.

In alternative embodiments, indicia are created that are distinguishable not on the basis of a colorant but on another distinguishable characteristic. For example, the indicia can be topological features that are observed visually and/or by touch. In one embodiment for example, an indentation (or multiple indentations) is used to mark the transition section. The indentations appear as "dents", "grooves", "ridges" or the like. These indentations can be textured lines, bumps, or other geometric shapes. FIG. 10A shows, for example, a bidirectional self-retaining suture 1002a which has a first section 1042a having a plurality of retainers oriented in a first direction; a second section 1046a having a plurality of retainers oriented in a second direction; and a transition section 1044a having no retainers and positioned between the first section 1042a and the second section 1046a. Self-retaining suture 1002a has a plurality of indentations 1054a on the transition section 1044a indicating and identifying the location of the transition section 1044b. The indentations depicted in FIG. 10A are similar to the indentations depicted with respect to FIG. 11B described below. However, the indentations of FIG. 10A can be less shallow and less wide and can be provided in a set of many indentations to mark the transition, while the single indentation of FIG. 11B can be deeper and wider in order to mark the transition.

Figure 10B:
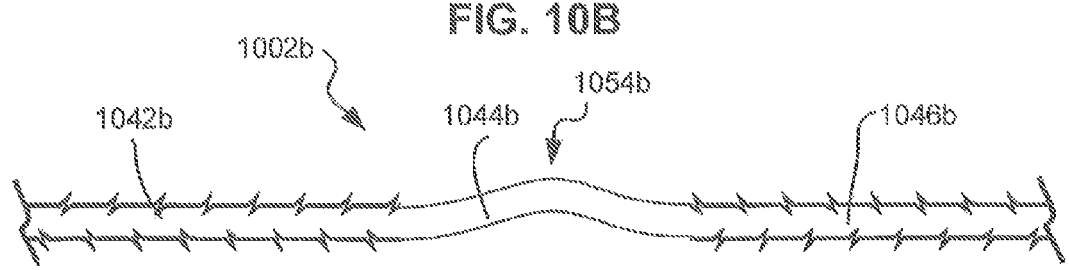

Another alternative embodiment is to fold the suture at (or near) the transition section to impart a deformation which can be easily tactilely and/or visually identified. For example, if the suture is folded or creased causing an indentation in the suture, this indentation can be used to mark the center suture segment. FIG. 10B shows, for example, a bidirectional self-retaining suture 1002*b* which has a first section 1042*b* having a plurality of retainers oriented in a first direction; a second section 1046*b* having a plurality of retainers oriented in a second direction; and a transition section 1044*b* having no retainers and positioned between the first section 1042*b* and the second section 1046*b*. Self-retaining suture 1002*b* has an indentation 1054*b* caused by, for example, folding transition section 1044*b*. Indentation 1054*b* indicates and identifies the location of the transition section 1044*b*. The deformation depicted in FIG. 10B is similar to that depicted with respect to FIG. 10D described below. However, indentation 1054*b* of FIG. 10B is a gradual indentation, while the deformation 1054*d* of FIG. 10D in this embodiment is more abrupt with cusps that define the boundaries of the deformation 1054*d*.

Figure 10C:
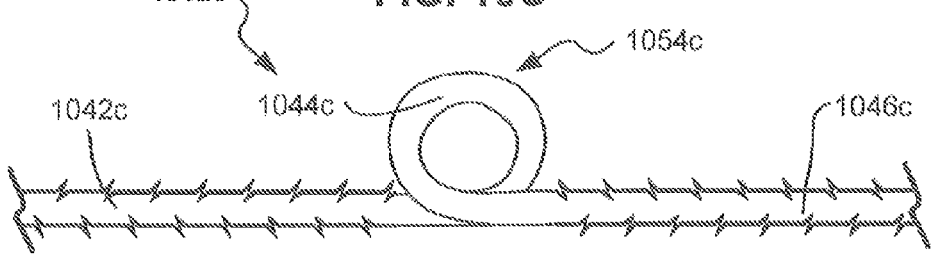
Figure 10D:
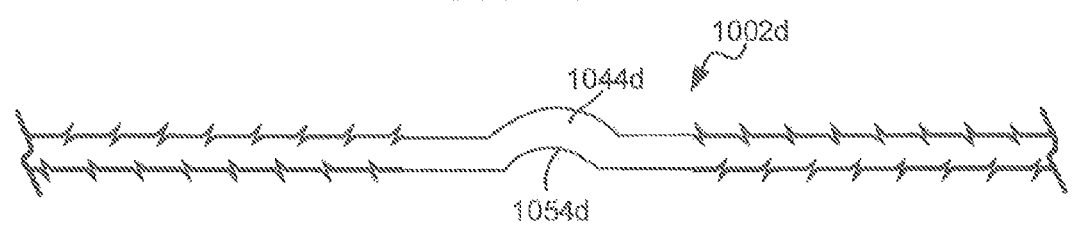
FIG. 10D shows a partial elevation view of a self-retaining suture according to an embodiment of the present invention having a transition segment deformation.

In another alternative embodiment, the self-retaining suture is heat-set into a particular configuration which identifies the transition section. For example, in one embodiment, the transition section is heat-set into a small loop allowing for easy recognition of the transition section. For example, if the suture is folded or creased causing an indentation in the suture, this indentation can be used to mark the center suture segment. FIG. 10C shows, for example, a bidirectional self-retaining suture 1002*c* which has a first section 1042*c* having a plurality of retainers oriented in a first direction; a second section 1046*c* having a plurality of retainers oriented in a second direction; and a transition section 1044*c* having no retainers and positioned between the first section 1042*c* and the second section 1046*c*. Self-retaining suture 1002*c* has a loop 1054*c* formed by, for example, heat setting transition section 1044*c* in a looped configuration. Loop 1054*c* indicates and identifies the location of the transition section 1044*c*. During use, the transition section 1044*c* is straightened out using tension to eliminate loop 1054*c* during implantation of the self-retaining suture 1002*c*.

Where a surgical procedure is being performed manually or by sufficiently sensitive robotically-assisted means, tactile markings may be provided; these may be particularly useful in sutures that are not self-retaining and in the retainer-free sections of self-retaining sutures. For example, in the case of self-retaining sutures, the doctor may wish to identify the transition segment; accordingly, the such as the transition segment may be provided with a configuration that is more easily detectably by touch than the simple absence of retainers, thereby obviating the surgeon's need to repeatedly and/or vigorously feel along the suture body to locate the transition segment. Such tactile markings may be provided in any section of interest of a suture, and may include a deformation in the section of interest, such as deformation 1054*d* of transition segment 1044*d* in suture 1002*d* shown in FIG. 10D. This may be effected by introducing a fold in the suture transition segment to impart a deformation which can be easily felt (and indeed may also be visible). Other types of tactilely-detectable suture deformations may similarly be provided.

Figure 11A:
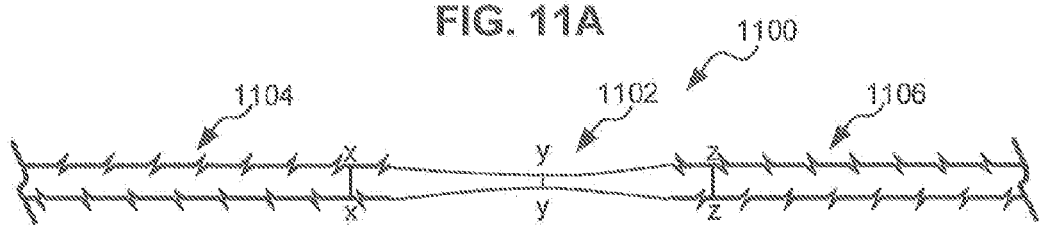
FIGS. 11A and 11B are partial elevation views of self-retaining sutures according to embodiments of the present invention having transition segment indentations.
Figure 11B:
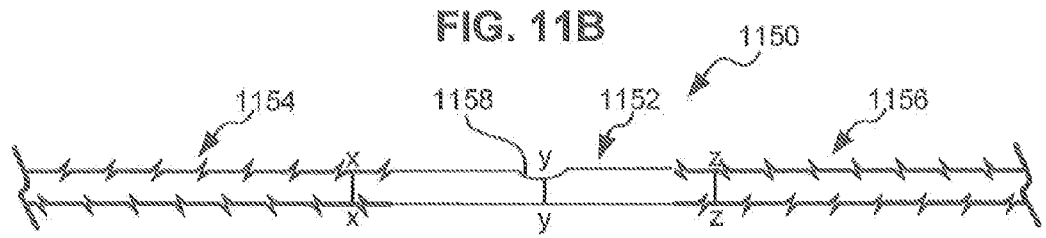

Easily detectable indentations in the section of interest may also be provided, such as by compression (e.g., stamping) of all or part of the section to deform the suture material therein, and by removal of suture material (e.g., cutting, etching, abrading, laser removal) from all or part of the suture section of interest to create an indentation. Indentations may take any form (such as, without limitation, grooves, wells, dents), as long as the diameter of the suture body at the indentation is less than the diameter of the suture body elsewhere, and as long as the diameter of suture body at the indentation remains sufficient to withstand breakage from forces normally exerted during suture deployment and engagement. For example, an indentation or narrowing of the suture diameter at the transition segment may assist a doctor in locating the transition segment. Referring to FIG. 11A, bidirectional self-retaining suture 1100 includes first plurality of retainers 1104, second plurality of retainers 1106, and transition segment 1102 (which may or may not correspond to the actual mid-point of the suture, depending on the arrangement of retainers). The diameter of suture of 1100 narrows gradually in transition segment 1102 so that at position y-y, the diameter is less than the diameter at either of positions x-x or/and z-z. In FIG. 11B, a more abrupt indention 1158 is provided in transition segment 1152 between retainer pluralities 1154 and 1156 of suture 1150. Again, the diameter of the suture at position y-y, where the depth of the indentation 1158 is at its greatest, is less than the diameter at either of position x-x or/and z-z.

Figure 12A:
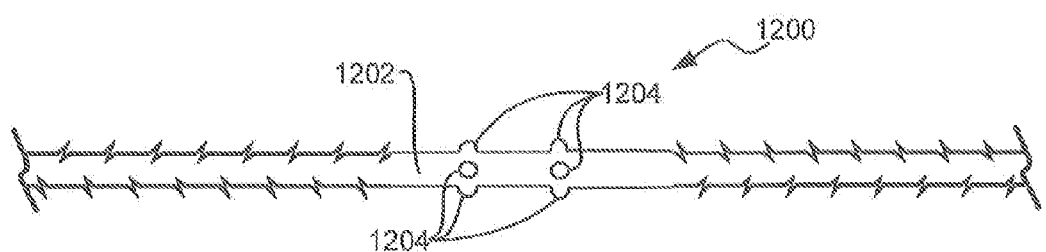
FIGS. 12A and 12B are partial elevation views of self-retaining sutures according to embodiments of the present invention having transition segment relief forms.
Figure 12B:
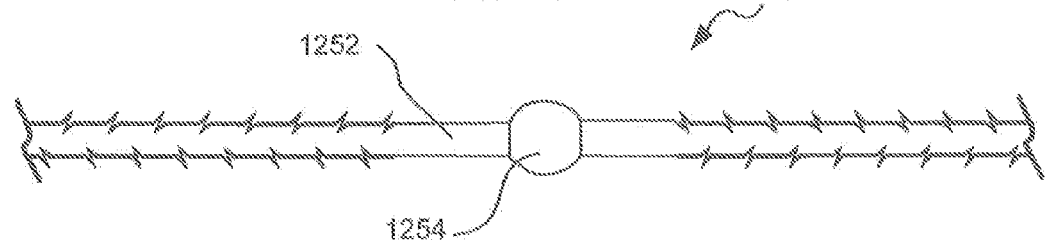

Other examples of tactile suture markings include a tactilely detectable increase in the diameter of the suture body at all or part of the section of interest. For example, protrusions on the surface of the section of interest that are easily detectable and distinguishable from tissue retainers may assist a surgeon in locating the section of interest, such as those protrusions 1204 in transition segment 1202 on suture 1200 in FIG. 12A. Alternatively, a ridge may be provided which runs continuously or discontinuously around the circumference of the suture along all or part of the section of interest, or such a ridge may run along only a portion of the circumference of the section of interest; see, for example, ridge 1254 in transition segment 1252 of suture 1250 in FIG. 12B. Similarly, other types of relief configurations or forms (such as filamentous projections, squares or other shapes) may be provided on the circumference of the section of interest. It should be noted that while such relief forms should be tactilely easily differentiable from tissue retainers, it is not necessary that they be configured to avoid inducing a fibrotic response in the tissue. Such increases in suture diameter at the section of interest can be created during manufacture of the suture thread (by, for example, extruding a larger amount of suture material for a particular length of a suture thread during an extrusion manufacturing process, cutting or stamping a suture thread with an expanded diameter portion, and so forth), or after the manufacture of the suture thread (by, for example, cutting material away from the ends of a suture thread, adding material to the desired portion of the thread by, for example, polymerization, and so forth) or otherwise adding or depositing material at a selected time during the manufacturing process.

Other forms of tactile demarcations include texture differences. Providing texture differences to all or part of the transition segment includes providing a plurality of areas of increased and/or decreased suture body diameter in the section of interest. For example, a plurality of indentation, a plurality of relief configurations, and any combinations thereof may be provided in the section of interest, by methods including, without limitation, compression, cutting, coating, application of agents such as abrasive, polymeriser, acid etchants, base etchants, and so forth.

The alternative technologies discussed in this section can be used to create self-retaining and ordinary sutures having indicia arranged in the patterns and distributions previously discussed with respect to laser-marked indicia. For example, the alternative technologies can be used to create self-retaining and ordinary sutures having indicia arranged in the patterns shown in FIGS. 8A-8L.

Materials

Suture threads described herein may be produced by any suitable method, including without limitation, injection molding, stamping, cutting, laser, extrusion, and so forth. The suture threads described herein may use any material conventionally used for the manufacture of sutures including for example, non-degradable polymers, biodegradable polymers and natural materials. With respect to cutting, polymeric suture threads/filaments may be manufactured or purchased for the suture body, and the retainers can be subsequently cut onto the suture body; the retainers may be hand-cut, laser-cut, or mechanically machine-cut using blades, cutting wheels, grinding wheels, and so forth. During cutting, either the cutting device or the suture thread may be moved relative to the other, or both may be moved, to control the size, shape and depth. Particular methods for cutting barbs on a filament are described in U.S. patent application Ser. No. 09/943,733 titled "Method Of Forming Barbs On A Suture And Apparatus For Performing Same" to Genova et al., and U.S. patent application Ser. No. 10/065,280 titled "Barbed Sutures" to Leung et al. both of which are incorporated herein by reference.

Clinical Uses

In addition to the general wound closure and soft tissue repair applications, self-retaining sutures can be used in a variety of other indications.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. The microsutures may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

It should be understood that the self-retaining sutures disclosed herein can be used in a variety of both human and veterinary applications for a wide number of surgical and traumatic purposes in human and animal healthcare, provide exemplary, and non-exclusive, statements of various aspects of the present invention, and should be read in conjunction with the optional embodiments of the invention as set forth herein.

A self-retaining suture thread comprising:

a suture thread having a colorant which has a color;

a first section of the suture thread bearing retainers oriented in a first direction;

a second section of the suture thread bearing retainers oriented in a second direction different than the first direction;

a transition section of the suture thread connecting the first section of suture thread and second section of suture thread;

a selected area within the transition region where the suture thread has been exposed to electromagnetic radiation adapted to change the color of the colorant;

wherein the colorant exposed to electromagnetic radiation within said selected area has a changed color which allows the selected area to be distinguished from portions of the suture thread outside the selected area;

whereby the changed color in the selected area is a distinguishable marking which allows the transition section to be recognized by a surgeon.

The self-retaining suture thread, wherein the colorant is a colorant selected from the group consisting of: titanium dioxide, D&C Violet No. 2; D&C Blue #6; D&C Blue #9; D&C Green #5; FD&C Blue #2; Logwood extract; [Phthalocyaninato(2-)]copper; and Chromium-cobalt-aluminum oxide.

The self-retaining suture, wherein the marking identifies at least one property of the suture thread.

The self-retaining suture, wherein the colorant is titanium dioxide, and the color is white and the changed color is black.

The self-retaining suture, wherein the colorant is [Phthalocyaninato(2-)]copper and the color is blue and the changed color is a reduction in blue color.

A heterofunctional suture thread comprising a plurality of sections wherein:

a first section has features different from the features of a second section; and said first section has optically-marked indicia which allow it to be distinguished from said second section.

The heterofunctional suture thread, wherein the heterofunctional suture thread is a self-retaining suture.

The heterofunctional suture thread, wherein the indicia identify at least one property of the suture thread.

The heterofunctional suture thread, wherein the heterofunctional suture thread is a bidirectional self-retaining suture.

The heterofunctional suture thread, wherein:

the heterofunctional suture thread is a bidirectional self-retaining suture; and the first section is a transition section positioned between the second section of the suture thread bearing retainers oriented in a first direction and a third section of the suture thread bearing retainers oriented in a second direction different than the first direction.

The heterofunctional suture thread, wherein:
the suture thread includes a colorant which has a first color;
said optically-marked indicia includes a marked area of suture thread wherein the colorant has been exposed to electromagnetic radiation adapted to change the color of the colorant; and
wherein the colorant exposed to electromagnetic radiation within said marked area of said optically-marked indicia has a second color distinguishable from the first color.

The heterofunctional suture thread, wherein the colorant is a colorant selected from the group consisting of: titanium dioxide, D&C Violet No. 2; D&C Blue #6; D&C Blue #9; D&C Green #5; FD&C Blue #2; Logwood extract; [Phthalocyaninato(2-)]copper; and Chromium-cobalt-aluminum oxide.

The heterofunctional suture thread, wherein the colorant is titanium dioxide, and the first color is white and the second color is black.

The heterofunctional suture thread, wherein the colorant is [Phthalocyaninato(2-)]copper and the first color is blue and the second color is a reduction in blue color.

The heterofunctional suture thread, wherein:
the heterofunctional suture thread is a bidirectional self-retaining suture;
the first section is a transition section positioned between the second section of the suture thread bearing retainers oriented in a first direction and a third section of the suture thread bearing retainers oriented in a second direction different than the first direction; and
wherein the optically-marked indicia is created on the suture thread after creation of the retainers of the first section.

The heterofunctional suture thread, wherein:
the heterofunctional suture thread is a bidirectional self-retaining suture;
the first one section is a transition section positioned between the second section of the suture thread bearing retainers oriented in a first direction and a third section of the suture thread bearing retainers oriented in a second direction different than the first direction; and
wherein the optically-marked indicia is created on the suture thread before creation of the retainers of the first section.

A bidirectional self-retaining suture thread having a transition section positioned between a first section of suture thread bearing retainers oriented in a first direction and a second section of suture thread bearing retainers oriented in a second direction different than the first direction wherein:
said transition section has a visible marking which allows the transition section to be recognized by a surgeon.

The bidirectional self-retaining suture thread wherein said visible marking is a deformation in the suture thread.

The bidirectional self-retaining suture thread wherein said visible marking is a discontinuity in the suture thread.

The bidirectional self-retaining suture thread wherein said visible marking is at least one of an indentation, a loop, a protrusion, a ridge, a discontinuity, a deformation and a reduced diameter in the suture thread.

The bidirectional self-retaining suture thread wherein the marking identifies characteristics of the suture thread.

The bidirectional self-retaining suture, wherein:
the suture thread includes a colorant which has a color;
said visible marking of the transition section occurs where the colorant has been exposed to electromagnetic radiation in order to change the color of the colorant; and
wherein the visible marking has a changed color which allows the visible marking to be distinguished from at least one of the first section of the suture thread and the second section of the suture thread.

The bidirectional self-retaining suture, wherein the suture thread is exposed to electromagnetic radiation in order to change the color of the colorant after creation of the retainers of the first section.

The bidirectional self-retaining suture, wherein the suture thread is exposed to electromagnetic radiation in order to change the color of the colorant before creation of the retainers of the first section.

The self-retaining suture thread, wherein the colorant is a colorant selected from the group consisting of: titanium dioxide, D&C Violet No. 2; D&C Blue #6; D&C Blue #9; D&C Green #5; FD&C Blue #2; Logwood extract; [Phthalocyaninato(2-)]copper; and Chromium-cobalt-aluminum oxide.

The self-retaining suture, wherein the colorant is [Phthalocyaninato(2-)]copper and the color is blue and the changed color is a reduction in blue color.

The bidirectional self-retaining suture, wherein:
the suture thread includes a colorant which has a color;
said visible marking of the transition section occurs where the colorant has been selectively exposed to a fluid in order to extract colorant from the suture thread; and
wherein the visible marking has a changed color which allows the visible marking to be distinguished from at least one of the first section of the suture thread and the second section of the suture thread.

The bidirectional self-retaining suture, wherein:
the suture thread includes a colorant which has a color;
said visible marking of the transition section occurs where the colorant has been selectively exposed to supercritical fluid in order to extract colorant from the suture thread; and
wherein the visible marking has a changed color which allows the visible marking to be distinguished from at least one of the first section of the suture thread and the second section of the suture thread.

A method of forming a marked heterofunctional suture thread comprising, in any order, the steps of:
forming a first section of the heterofunctional suture thread and a second section of the heterofunctional suture thread wherein the first section has features that are different from the features of the second section; and
optically-marking indicia on the first section which allows the first section to be distinguished from the second section.

The method including the steps of:
using an electromagnetic radiation source to optically mark the first section.

The method including the step of forming a third section of the heterofunctional suture thread with the first section between the second section and the third section, wherein the third section has features that are different from the first section and the second section.

The method including the step of forming tissue retainers on the second section and on the third section, wherein the tissue retainers on the second section point in a different direction than the tissue retainers on the third section, and wherein no tissue retainers are formed on the first section.

The method including the step of:
using a suture thread that has a colorant; and
causing the colorant to change color in order to provide the indicia.

The method wherein the using step includes using an electromagnetic radiation source to change the color of the colorant.

A method of forming a marked heterofunctional suture thread comprising, in any order, the steps of:
forming a first section of the heterofunctional suture thread and a second section of the heterofunctional suture thread wherein the first section has features that are different from the features of the second section and wherein the first section and the section each comprise a colorant;
selectively exposing a portion of the first section of the heterofunctional suture thread to a dye extraction agent to extract colorant from the portion thereby creating an indicia which allows the first section to be distinguished from the second section.

The method wherein the dye extraction agent is a supercritical fluid.

The method including the step of forming a third section of the heterofunctional suture thread with the first section between the second section and the third section, wherein the third section has features that are different from the first section and the second section.

The method including the step of forming tissue retainers on the second section and on the third section, wherein the tissue retainers on the second section point in a different direction than the tissue retainers on the third section, and wherein no tissue retainers are formed on the first section.

A bidirectional self-retaining suture thread having a transition section positioned between a first section of suture thread bearing retainers oriented in a first direction and a second section of suture thread bearing retainers oriented in a second direction different than the first direction wherein:
said transition section has a transition marking which allows the transition section to be recognized by a surgeon; and
the first section of suture thread has a first marking which allows the first section of suture thread to be distinguished from the second section of suture thread by a surgeon.

The bidirectional self-retaining suture thread wherein at least one of the transition marking and the first marking identifies at least one property of the suture thread.

The bidirectional self-retaining suture, wherein:
the suture thread includes a colorant which has a color;
said first marking and said transition marking comprise portions of the suture thread in which the colorant has been exposed to electromagnetic radiation causing a change in the color of the colorant.

The bidirectional self-retaining suture, wherein the suture thread is exposed to electromagnetic radiation in order to change the color of the colorant after creation of the retainers of the first section.

The bidirectional self-retaining suture, wherein the suture thread is exposed to electromagnetic radiation in order to change the color of the colorant before creation of the retainers of the first section.

The self-retaining suture thread, wherein the colorant is a colorant selected from the group consisting of: titanium dioxide, D&C Violet No. 2; D&C Blue #6; D&C Blue #9; D&C Green #5; FD&C Blue #2; Logwood extract; [Phthalocyaninato(2-)]copper; and Chromium-cobalt-aluminum oxide.

The bidirectional self-retaining suture, wherein:
the suture thread includes a colorant which has a color;
said first marking and said transition marking comprise portions of the suture thread in which the colorant has been selectively exposed to a fluid in order to extract colorant from the suture thread; and
wherein the transition marking has a changed color which allows the transition marking to be distinguished from the first section of the suture thread and the second section of the suture thread.

The bidirectional self-retaining suture, wherein:
the suture thread includes a colorant which has a color; and
said first marking and said transition marking comprise portions of the suture thread in which the colorant has been selectively exposed to a fluid in order to extract colorant from the suture thread.

The bidirectional self-retaining suture, wherein:
the transition marking is different from the first marking.

The bidirectional self-retaining suture, wherein:
the suture thread includes a colorant which has a color;
said first marking and said transition marking comprise portions of the suture thread in which the colorant has been selectively exposed to a supercritical fluid in order to extract colorant from the suture thread; and
wherein the transition marking has a changed color which allows the transition marking to be distinguished from the first section of the suture thread and the second section of the suture thread.

A method of forming a marked heterofunctional suture thread comprising, in any order, the steps of:
obtaining a suture thread comprising a colorant having a color;
forming first structural features on a first section of the suture thread;
forming second structural features on a second section of the suture thread;
the first section of suture thread being connected by a transition section of the suture thread to the second section of the suture thread; and
marking the transition section by changing the color of the colorant so that the transition section is distinguishable from the first section and the second section of the suture thread.

The method wherein step (e) comprises selectively exposing a portion of the transition section of the suture thread to a dye extraction agent to extract colorant from the portion thereby creating an indicia which allows the transition section to be distinguished from the first section and the second section of the suture thread.

The method wherein step (e) comprises selectively exposing a portion of the transition section of the suture thread to a supercritical fluid to extract colorant from the portion thereby creating an indicia which allows the transition section to be distinguished from the first section and the second section of the suture thread.

The method wherein step (e) comprises selectively exposing a portion of the transition section of the suture thread to electromagnetic radiation to change the color of the colorant in the portion thereby creating an indicia which allows the transition section to be distinguished from the first section and the second section of the suture thread.

The method wherein step (e) comprises selectively exposing a portion of the transition section of the suture thread to laser light to change the color of the colorant in the portion thereby creating an indicia which allows the transition section to be distinguished from the first section and the second section of the suture thread.

The method wherein: steps (b) and (c) comprise:
forming first structural features on a first section of the suture thread wherein the first structural features are tissue retainers having a first orientation; and
forming second structural features on a second section of the suture thread wherein the second structural features are tissue retainers having a second orientation different than the first orientation.

An apparatus for making a self-retaining suture thread having a transition section positioned between a first section of suture thread bearing retainers oriented in a first direction and a second section of suture thread bearing retainers oriented in a second direction different than the first direction wherein the apparatus comprises:

a frame;

a first chuck adapted to hold a first end of the suture thread wherein the first chuck is movably mounted on the frame;

a second chuck adapted to hold a second end of the suture thread wherein the second chuck is movably mounted on the frame;

a cutting head adapted to form retainer on the suture thread wherein the cutting head is provided in a position relative to the frame;

a marking head adapted to create visible indicia upon the suture thread wherein the marking head is provided in a position relative to the frame;

a transport mechanism adapted to move the first chuck and the second chuck along the axis of the suture thread relative to the frame such that different points along the suture thread are aligned with the cutting head and marking head;

whereby the first section of suture thread can be aligned with the cutting head to allow the cutting head to form retainers oriented in a first direction, the second section of suture thread can be aligned with the cutting head to form retainers oriented in a second direction, and the transition section can be aligned with the marking head to form indicia which allow the transition section to be distinguished from the first section and second section of the suture thread.

The apparatus wherein said marking head is adapted to expose the suture thread to a fluid in order to change a color of the suture thread.

The apparatus wherein said marking head is adapted to expose the suture thread to a supercritical fluid in order to change a color of the suture thread.

The apparatus wherein the marking head comprises:

a source of electromagnetic radiation; and an optical system which directs the electromagnetic radiation to a selected portion of the suture thread to create visible indicia upon the suture thread.

The apparatus wherein the source of electromagnetic radiation is adapted to change a color of a colorant in the suture thread without cutting the suture thread.

The apparatus wherein the source of electromagnetic radiation is a laser adapted to change a color of a colorant in the suture thread without cutting the suture thread.

A method for making a self-retaining suture on an apparatus having a cutting head, a marking head and a suture translation mechanism, the method comprising:

securing a suture thread in the apparatus, the suture thread including a colorant having a color;

translating the suture thread to align a first section of the suture thread with a cutting head, and forming retainers having a first orientation on the first section of suture thread;

translating the suture thread to align a second section of the suture thread with the cutting head, and forming retainers having a second orientation on the second section of suture thread;

translating the suture thread to align a transition section of the suture thread located between the first section of suture thread and the second section of suture thread with a marking head, and operating the marking head to change the color of the colorant in the transition section of the suture thread;

removing the suture thread from the apparatus; and wherein steps (b), (c) and (d) are performed in any order and each of steps (b), (c) and (d) are performed after step (a) and before step (e).

The method wherein said step of operating said marking head included operating said marking head to expose the suture thread to a fluid in order to change a color of the suture thread.

The method wherein said step of operating said marking head includes operating said marking head to expose the suture thread to supercritical fluid in order to change a color of the suture thread.

The method wherein the marking head comprises a source of electromagnetic radiation and wherein step (d) comprises:

translating the suture thread to align a transition section of the suture thread located between the first section of suture thread and the second section of suture thread with the marking head, and operating the marking head to expose a region of the suture thread in the transition head to electromagnetic radiation from the source of electromagnetic radiation to change the color of the colorant in the region of the transition section of the suture thread.

The method wherein the marking head comprises a laser and wherein step (d) comprises:

translating the suture thread to align a transition section of the suture thread located between the first section of suture thread and the second section of suture thread with the marking head, and operating the marking head to direct laser light from the laser at a region of the suture thread in the transition head to change the color of the colorant in the region of the transition section of the suture thread.

A method for making a self-retaining suture on an apparatus having a cutting head and a suture translation mechanism, the method comprising:

obtaining a suture thread having a visible indicia;

subsequent to step (a) securing the suture thread in the apparatus and identifying the position of the visible indicia relative to the cutting head;

translating the suture thread to align a first section of the suture thread on one side of the visible indicia with the cutting head, and forming retainers having a first orientation on the first section of suture thread;

translating the suture thread to align a second section of the suture thread on a second side of the visible indicia with the cutting head, and forming retainers having a second orientation on the second section of suture thread; and subsequent to steps (a), (b), (c) and (d) removing the suture thread from the apparatus.

The method wherein step (a) comprises:

(a1) obtaining a suture thread comprising a colorant having a color; and (a2) treating a region of the suture thread to change the color of the colorant thereby creating a visible indicia on the suture thread.

The method wherein step (a) comprises:

(a1) obtaining a suture thread comprising a colorant having a color; and (a2) treating a region of the suture thread with a dye extraction agent to remove colorant from the region thereby creating a visible indicia on the suture thread.

The method wherein step (a) comprises:

(a1) obtaining a suture thread comprising a colorant having a color; and (a2) treating a region of the suture thread with a supercritical fluid to remove colorant from the region thereby creating a visible indicia on the suture thread.

The method wherein step (a) comprises:
(a1) obtaining a suture thread comprising a colorant having a color; and
(a2) treating a region of the suture thread with a laser to denature the colorant in the region thereby creating a visible indicia on the suture thread.

A self-retaining suture comprising:
a suture thread having a first section marked with a first indicia and a second section marked with a second indicia and a boundary where the first indicia end and the second indicia begin;
a first region of the first section of the suture thread bearing retainers oriented in a first direction;
a second region of the second section of the suture thread bearing retainers oriented in a second direction different than the first direction;
a transition region of suture thread between the first region and the second region; and
whereby the first region is identified by the first indicia, the second region is identified by the second indicia, and the transition region is identified by the boundary.

The self-retaining suture wherein at least one of the first indicia, the second indicia and the boundary identify at least one property of the suture thread.

The self-retaining suture, wherein:
the suture thread comprises a colorant which imparts a color to the suture thread; and
the second section of suture thread has been treated to modify the colorant and thereby impart a changed color to the suture thread; and
wherein the first indicia is the color of the suture thread and the second indicia is the changed color of the suture thread.

The self-retaining suture, wherein the colorant is a colorant selected from the group consisting of: titanium dioxide, D&C Violet No. 2; D&C Blue #6; D&C Blue #9; D&C Green #5; FD&C Blue #2; Logwood extract; [Phthalocyaninato(2-)]copper; and Chromium-cobalt-aluminum oxide.

The self-retaining suture, wherein the colorant is titanium dioxide, and the color is white and the changed color is black.

The self-retaining suture, wherein the colorant is [Phthalocyaninato(2-)]copper; and the color is blue and the changed color is a reduction in blue color.

An apparatus for making a self-retaining suture thread having a transition section positioned between a first section of suture thread bearing retainers oriented in a first direction and a second section of suture thread bearing retainers oriented in a second direction different than the first direction wherein the apparatus comprises:
a frame;
a first chuck adapted to hold a first end of the suture thread wherein the first chuck is movably mounted on the frame;
a second chuck adapted to hold a second end of the suture thread wherein the second chuck is movably mounted on the frame;
a cutting head adapted to form retainer on the suture thread wherein the cutting head is secured in a fixed position relative to the frame;
a marking head adapted to create visible indicia upon the suture thread wherein the cutting head is secured in a fixed position relative to the frame;
a transport mechanism adapted to move the first chuck and the second chuck along the axis of the suture thread relative to the frame such that different points along the suture thread are aligned with the cutting head and marking head;
whereby the first section of suture thread can be aligned with the cutting head to allow the cutting head to form retainers oriented in a first direction, the second section of suture thread can be aligned with the cutting head to form retainers oriented in a second direction, and the transition section can be aligned with the marking head to form indicia which allow the transition section to be distinguished from the first section and second section of the suture thread.

A system for performing surgical procedures comprising:
a tool system adapted to assist a physician to perform a surgical procedure with the hands of the physician located externally to the patient;
a suture with a marker on the suture that indicate information that includes at least one of suture type, suture material, suture dimensions, position on the suture, suture tension, suture drug load, suture condition, suture characteristics or suture properties; and
said tool system including a device that can assist the physician with the information on the marker.

The system wherein:
said marker is one of a visible marker or a non-visible marker.

The system wherein the marker is at least one of a color, a bar code, a code, or an RFID tag.

The system wherein the marker is at least one of human readable or machine readable.

The system wherein the tool system can at least one of read the marker or decode the marker.

The system wherein the tool system can read the marker and take an action.

The system wherein the tool system is an endoscopic system.

The system wherein the tool system is a robotic surgical assistance tool.

The system wherein the tool system can read the marker and display the information about the suture.

The system wherein the tool system can read the marker and provide the information to the physician over at least one of a visual mechanism, an aural mechanism, or a haptic mechanism.

The system wherein said surgical procedure is a microsurgical procedure.

A system for performing surgical procedures comprising:
a tool system adapted to assist a physician to perform a surgical procedure with the hands of the physician located externally to the patient;
a suture with a marker on the suture that indicate at least one of suture type, suture material, suture dimensions, position on the suture, suture tension, suture drug load, suture condition, suture characteristics or suture properties;
said tool system including a device that can assist the physician with the information on the marker;
wherein the marker is at least machine readable;
wherein the tool system can at least one of read the marker or decode the marker; and
wherein the tool system can display the information about the suture.

The system wherein the marker is at least one of a color, a bar code, a code, or an RFID tag.

The system wherein the tool system can take an action after reading the marker.

The system wherein the tool system is an endoscopic system.

The system wherein the tool system is a robotic surgical assistance tool.

The system wherein the tool system can provide the information to the physician over at least one of a visual mechanism, an aural mechanism, or a haptic mechanism.

A method of performing a surgical procedure comprising the steps of:

using a tool system adapted to assist a physician to perform a surgical procedure with the hands of the physician located externally to the patient;

using a suture with a marker on the suture that indicate information that includes at least one of suture type, suture material, suture dimensions, position on the suture, suture tension, suture drug load, suture condition, suture characteristics or suture properties; and wherein said tool system using step includes using said tool system that includes a device that can assist the physician with the information on the marker.

The method wherein:

said marker using step includes using a marker is one of a visible marker or a non-visible marker.

The method wherein:

said marker using step includes using a marker that is at least one of a color, a bar code, a code, or an RFID tag.

The method wherein:

said marker using step includes using a marker that is at least one of human readable or machine readable.

The method wherein the tool system using step includes using a tool system that can at least one of read the marker or decode the marker.

The method wherein:

the tool using step includes using a tool system can read the marker and take an action.

The method wherein:

the tool system using step includes using a tool system that is an endoscopic system.

The method wherein:

the tool system using step includes using a tool system that is a robotic surgical assistance tool.

The method wherein:

the tool system using step includes using the tool system to display the information about the suture.

The system wherein:

the tool system using step included using a tool system that can read the marker and provide the information to the physician over at least one of a visual mechanism, an aural mechanism, or a haptic mechanism.

A method for performing surgical procedures comprising:

using a tool system adapted to assist a physician to perform a surgical procedure with the hands of the physician located externally to the patient;

using a suture with a marker on the suture that indicate at least one of suture type, suture material, suture dimensions, position on the suture, suture tension, suture drug load, suture condition, suture characteristics or suture properties, which marker is machine readable; and wherein said tool system using step includes using a tool system that includes a device that can assist the physician with the information on the marker by at least one of reading the marker or decoding the marker, and by displaying the information about the suture.

In accordance with particular embodiments the self-retaining sutures are bidirectional self-retaining sutures.

In accordance with particular embodiments, the present invention further provides methods and devices for providing one or more visible/recognizable indicia on a section of a self-retaining suture.

In accordance with particular embodiments, the present invention further provides a bidirectional self-retaining suture thread including a first section of the suture thread having retainers oriented in a first direction, a second section of the suture thread having retainers oriented in a second direction that is different from said first direction, and a transition section of the suture thread located between the first section and the second section, wherein at least one of the aforementioned sections includes within it a region which has been treated to create a marker indicative of one of: presence of retainers, absence of retainers, and orientation of retainers.

In some of these particular embodiments, the suture thread has a colorant and at least one of these sections has been treated to create the marker by exposing the region of the suture thread to a fluid in order to extract the colorant from the suture thread within said region. In some other of these particular embodiments, at least one of these sections has been treated to create the marker which may be an indentation, a loop, a protrusion, a ridge, a discontinuity, a deformation, or a reduced diameter, in the suture thread.

In yet others of these particular embodiments, at least one of the sections includes a region which has been treated with electromagnetic radiation to create a marker indicative of the presence of retainers, the absence of retainers, or the orientation of retainers within at least one of the sections. In yet further of these embodiments, each of the sections includes a region which has been treated with electromagnetic radiation to create a marker indicative of the presence of retainers, the absence of retainers, or the orientation of retainers.

In some of the embodiments incorporating at least one region in at least one section that has been treated with electromagnetic radiation to create a marker, the transition section includes such a region and the marker is a visible marker adapted to allow said transition section to be recognized by a surgeon.

In some of the embodiments incorporating at least one region in at least one section that has been treated with electromagnetic radiation to create a marker, the transition section includes a first region which has been treated with electromagnetic radiation to create a first marker adapted to be recognized by a surgeon; and the second section includes a second region which has been treated with electromagnetic radiation to create a second marker different than the first marker and adapted to be recognized by a surgeon.

In some of the embodiments incorporating at least one region in at least one section that has been treated with electromagnetic radiation to create a marker, the first section includes a first region which has been treated with electromagnetic radiation to create a first marker, the second section includes a second region which has been treated with electromagnetic radiation to create a second marker, the transition section includes a third region which has been treated with electromagnetic radiation to create a third marker. In such embodiments, the first marker is different than the second marker, and the third marker is different than the first second markers.

In some of the embodiments incorporating at least one region in at least one section that has been treated with electromagnetic radiation to create a marker, the marker is an optically-marked marker.

In some of the embodiments incorporating at least one region in at least one section that has been treated with electromagnetic radiation to create a marker, the marker is visible.

In some of the embodiments incorporating at least one region in at least one section that has been treated with electromagnetic radiation to create a marker, the suture thread includes a colorant and the electromagnetic radiation has changed the color to create said marker.

In some of the embodiments incorporating at least one region in at least one section that has been treated with electromagnetic radiation to create a marker, the suture thread includes a colorant selected from the group consisting of:

titanium dioxide, D&C Violet No. 2; D&C Blue #6; D&C Blue #9; D&C Green #5; FD&C Blue #2; Logwood extract; [Phthalocyaninato(2-)]copper; and Chromium-cobalt-aluminum oxide; and the colorant in the region which has been treated with electromagnetic radiation has changed color to create said marker.

In some of the embodiments incorporating at least one region in at least one section that has been treated with electromagnetic radiation to create a marker, the suture thread includes a colorant which has a first color and the colorant in the region which has been treated with electromagnetic radiation has a second color distinguishable from the first color.

In some of the embodiments in which the suture thread includes a colorant which has a first color and the colorant in the region which has been treated with electromagnetic radiation has a second color distinguishable from the first color, the colorant is titanium dioxide and the first and second colors are white and black, respectively.

In some of the embodiments in which the suture thread includes a colorant which has a first color and the colorant in the region which has been treated with electromagnetic radiation has a second color distinguishable from the first color, the colorant is [Phthalocyaninato(2-)]copper and the first color is blue while the second color is less blue.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A bidirectional self-retaining suture thread comprising:
    a first section of the suture thread having retainers oriented in a first direction;
    a second section of the suture thread having retainers oriented in a second direction that is different from said first direction;
    a transition section of the suture thread located between the first section and the second section; and
    at least one of said first section, said second section and said transition section includes a mixture of a first colorant and a second colorant different from said first colorant in a region of said suture thread, and wherein at least a portion of said first colorant has been treated with electromagnetic radiation in the form of a laser to bleach the colorant, wherein said laser treatment creates a bleached section, leaving said second colorant, wherein said second colorant serves as a marker indicative of one of: presence of retainers, absence of retainers, and orientation of retainers within said at least one of said first section, said second section and said transition section.

2. The bidirectional self-retaining suture thread of claim 1, wherein each of said first section, said second section and said transition includes a region of said suture thread which has been treated with electromagnetic radiation in the form of a laser to create a bleached section that serves as a marker indicative of one of: presence of retainers, absence of retainers, and orientation of retainers.

3. The bidirectional self-retaining suture thread of claim 1, wherein:
    said transition section includes a first region of said suture thread which has been treated with electromagnetic radiation in the form of a laser to create a first bleached section that serves as a marker adapted to be recognized by a surgeon; and
    said second section includes a second region of said suture thread which has been treated with electromagnetic radiation in the form of a laser to create a second bleached section that serves as a marker different than the first marker and adapted to be recognized by a surgeon.

4. The bidirectional self-retaining suture thread of claim 1, wherein:
    said first section includes a first region of said suture thread which has been treated with electromagnetic radiation in the form of a laser to create a first bleached section that serves as a marker;
    said second section includes a second region of said suture thread which has been treated with electromagnetic radiation in the form of a laser to create a second bleached section that serves as a marker;
    said transition section includes a third region of said suture thread which has been treated with electromagnetic radiation in the form of a laser to create a third bleached section that serves as a marker; and
    wherein said first marker is different than said second bleached section that serves as a marker, and said third bleached section that serves as a marker is different than said first bleached section that serves as a marker and said second bleached section that serves as a marker.

5. The bidirectional self-retaining suture thread of claim 1, wherein:
    the first colorant is [Phthalocyaninato(2-)] copper.

6. The bidirectional self-retaining suture thread of claim 5, wherein:
    said second colorant provides a different color than the first colorant.

7. A bidirectional self-retaining suture thread comprising:
    a first section of the suture thread having retainers oriented in a first direction; a second section of the suture thread having retainers oriented in a second direction that is different from said first direction; a transition section of the suture thread located between the first section and the second section; and at least one of said first section, said second section and said transition section includes a region of said suture thread which has been treated to create a marker indicative of one of: presence of retainers, absence of retainers, and orientation of retainers within said at least one of said first section, said second section and said transition section, wherein:
    the suture thread has a mixture of a first colorant and a second colorant, the second colorant being different than the first colorant;
    the at least one of said first section, said second section and said transition section has been treated to create the marker by exposing the region of the suture thread to a fluid in order to extract the first colorant from the suture thread within said region, leaving the second colorant within the suture thread.

* * * * *